US012427326B2

(12) United States Patent
Mar et al.

(10) Patent No.: US 12,427,326 B2
(45) Date of Patent: Sep. 30, 2025

(54) BIOSTIMULATOR HAVING FIXATION ELEMENT

(71) Applicant: Pacesetter, Inc., Sylmar, CA (US)

(72) Inventors: Craig E. Mar, Fremont, CA (US); Thomas B. Eby, Mountain View, CA (US); Paul Paspa, Los Gatos, CA (US); Sondra Orts, Sunnyvale, CA (US); Matthew G. Fishler, Scotts Valley, CA (US); Stephen Lee, San Jose, CA (US); Carl Lance Boling, San Jose, CA (US); Thomas Robert Luhrs, Santa Rosa, CA (US)

(73) Assignee: PACESETTER, INC., Sylmar, CA (US)

( * ) Notice: Subject to any disclaimer, the term of this patent is extended or adjusted under 35 U.S.C. 154(b) by 0 days.

(21) Appl. No.: 18/393,654

(22) Filed: Dec. 21, 2023

(65) Prior Publication Data

US 2024/0123240 A1    Apr. 18, 2024

Related U.S. Application Data

(63) Continuation of application No. 17/513,794, filed on Oct. 28, 2021, now Pat. No. 11,850,435, which is a
(Continued)

(51) Int. Cl.
*A61N 1/375* (2006.01)
*A61N 1/372* (2006.01)
*A61N 1/05* (2006.01)

(52) U.S. Cl.
CPC ..... *A61N 1/37518* (2017.08); *A61N 1/37205* (2013.01); *A61N 1/375* (2013.01);
(Continued)

(58) Field of Classification Search
CPC ................ A61N 1/0573; A61N 1/3756; A61N 1/37518; A61N 1/37512; A61N 1/37205;
(Continued)

(56) References Cited

U.S. PATENT DOCUMENTS

| 3,943,936 | A | 3/1976 | Rasor et al. |
| 3,974,834 | A | 8/1976 | Kane |

(Continued)

FOREIGN PATENT DOCUMENTS

| EP | 1835962 A1 | 9/2007 |
| EP | 3106201 A1 | 12/2016 |

(Continued)

OTHER PUBLICATIONS

First Office Action from related Chinese Patent Application No. 201880085098.1 mailed on Mar. 6, 2023 (28 pages including translation).
(Continued)

*Primary Examiner* — Jon Eric C Morales
(74) *Attorney, Agent, or Firm* — WOMBLE BOND DICKINSON (US) LLP

(57) ABSTRACT

A biostimulator, such as a leadless cardiac pacemaker, including a fixation element to engage tissue and one or more backstop elements to resist back-out from the tissue, is described. The fixation element can be mounted on a housing of the biostimulator such that a helix of the fixation element extends distally to a leading point. The leading point can be located on a distal face of the helix at a position that is proximal from a center of the distal face. The backstop elements can include non-metallic filaments, such as sutures, or can include a pinch point of the biostimulator. The backstop features can grip the tissue to prevent unscrewing of the fixation element. Other embodiments are also described and claimed.

19 Claims, 31 Drawing Sheets

Related U.S. Application Data continuation of application No. 16/181,154, filed on Nov. 5, 2018, now Pat. No. 11,185,704.

(60) Provisional application No. 62/750,034, filed on Oct. 24, 2018, provisional application No. 62/700,112, filed on Jul. 18, 2018, provisional application No. 62/646,247, filed on Mar. 21, 2018, provisional application No. 62/637,257, filed on Mar. 1, 2018, provisional application No. 62/582,125, filed on Nov. 6, 2017.

(52) U.S. Cl.
CPC ....... *A61N 1/37512* (2017.08); *A61N 1/3756* (2013.01); *A61N 1/057* (2013.01)

(58) Field of Classification Search
CPC ........ A61N 1/057; A61N 1/375; A61N 1/056; A61N 2001/0578; A61N 1/362; A61N 1/3621; A61N 1/3624; A61N 1/37229; A61N 1/37282; A61B 2090/3966
See application file for complete search history.

(56) References Cited

U.S. PATENT DOCUMENTS

| | | |
|---|---|---|
| 4,106,512 A | 8/1978 | Bisping |
| 4,311,153 A | 1/1982 | Smits |
| 4,972,848 A | 11/1990 | Di et al. |
| 5,003,992 A | 4/1991 | Holleman et al. |
| 5,076,285 A | 12/1991 | Hess et al. |
| 5,575,814 A | 11/1996 | Giele et al. |
| 5,702,437 A | 12/1997 | Baudino |
| 5,716,391 A | 2/1998 | Grandjean |
| 5,741,321 A | 4/1998 | Brennen |
| 5,776,178 A | 7/1998 | Pohndorf et al. |
| 5,837,006 A | 11/1998 | Ocel et al. |
| 5,948,015 A | 9/1999 | Hess et al. |
| 6,428,368 B1 | 8/2002 | Hawkins et al. |
| 6,489,562 B1 | 12/2002 | Hess et al. |
| 6,556,874 B2 | 4/2003 | Audoglio |
| 6,907,298 B2 | 6/2005 | Smits et al. |
| 6,909,920 B2 | 6/2005 | Lokhoff et al. |
| 6,931,285 B2 | 8/2005 | Bischoff |
| 6,931,286 B2 | 8/2005 | Sigg et al. |
| 7,027,876 B2 | 4/2006 | Casavant et al. |
| 7,082,335 B2 | 7/2006 | Klein et al. |
| 7,103,418 B2 | 9/2006 | Laske et al. |
| 7,127,302 B2 | 10/2006 | Palm |
| 7,158,838 B2 | 1/2007 | Seifert et al. |
| 7,187,971 B2 | 3/2007 | Sommer et al. |
| 7,274,966 B2 | 9/2007 | Sommer et al. |
| 7,313,445 B2 | 12/2007 | McVenes et al. |
| 7,532,939 B2 | 5/2009 | Sommer et al. |
| 7,580,758 B2 | 8/2009 | Junge et al. |
| 7,599,747 B2 | 10/2009 | Feldmann et al. |
| 7,657,325 B2 | 2/2010 | Williams |
| 7,657,326 B2 | 2/2010 | Bodner et al. |
| 7,720,550 B2 | 5/2010 | Sommer et al. |
| 7,751,905 B2 | 7/2010 | Feldmann et al. |
| 7,844,348 B2 | 11/2010 | Swoyer et al. |
| 7,860,580 B2 | 12/2010 | Falk et al. |
| 7,937,148 B2 | 5/2011 | Jacobson |
| 7,937,161 B2 | 5/2011 | Hastings et al. |
| 7,942,917 B2 | 5/2011 | Nowak, Jr. |
| 7,945,333 B2 | 5/2011 | Jacobson |
| 7,967,857 B2 | 6/2011 | Lane |
| 8,010,209 B2 | 8/2011 | Jacobson |
| 8,057,459 B2 | 11/2011 | Rioux et al. |
| 8,135,467 B2 | 3/2012 | Markowitz et al. |
| 8,211,169 B2 | 7/2012 | Lane et al. |
| 8,219,209 B2 | 7/2012 | Arnholt et al. |
| 8,219,213 B2 | 7/2012 | Sommer et al. |
| 8,239,039 B2 | 8/2012 | Zarembo et al. |
| 8,313,621 B2 | 11/2012 | Goad et al. |
| 8,346,374 B2 | 1/2013 | Foster et al. |
| 8,352,025 B2 | 1/2013 | Jacobson |
| 8,412,351 B2 | 4/2013 | Zeijlemaker et al. |
| 8,457,742 B2 | 6/2013 | Jacobson |
| 8,478,429 B2 | 7/2013 | Walker et al. |
| 8,478,430 B2 | 7/2013 | Sommer et al. |
| 8,489,205 B2 | 7/2013 | Stotts et al. |
| 8,500,757 B2 | 8/2013 | Miraki et al. |
| 8,527,068 B2 | 9/2013 | Ostroff |
| 8,543,224 B2 | 9/2013 | Foster et al. |
| 8,560,087 B2 | 10/2013 | Foster |
| 8,694,128 B2 | 4/2014 | Seifert et al. |
| 8,755,909 B2 | 6/2014 | Sommer et al. |
| 8,812,134 B2 | 8/2014 | Foster et al. |
| 8,874,232 B2 | 10/2014 | Chen |
| 8,923,985 B2 | 12/2014 | Clark et al. |
| 8,948,883 B2 | 2/2015 | Eggen et al. |
| 8,954,168 B2 | 2/2015 | Foster |
| 9,020,611 B2 | 4/2015 | Khairkhahan et al. |
| 9,056,180 B2 | 6/2015 | Powell et al. |
| 9,089,695 B2 | 7/2015 | Seifert et al. |
| 9,186,209 B2 | 11/2015 | Weber et al. |
| 9,216,298 B2 | 12/2015 | Jacobson |
| 9,242,102 B2 | 1/2016 | Khairkhahan et al. |
| 9,272,155 B2 | 3/2016 | Ostroff |
| 9,333,342 B2 | 5/2016 | Haasl et al. |
| 9,333,344 B2 | 5/2016 | Foster |
| 9,358,387 B2 | 6/2016 | Suwito et al. |
| 9,358,400 B2 | 6/2016 | Jacobson |
| 9,421,384 B2 | 8/2016 | Taff et al. |
| 9,517,336 B2 | 12/2016 | Eggen et al. |
| 9,579,500 B2 | 2/2017 | Rys et al. |
| 9,682,230 B2 | 6/2017 | Zhang et al. |
| 9,694,172 B2 | 7/2017 | Foster et al. |
| 9,724,126 B2 | 8/2017 | Gerber et al. |
| 9,770,586 B2 | 9/2017 | Doerr et al. |
| 9,775,982 B2 | 10/2017 | Grubac et al. |
| 9,808,617 B2 | 11/2017 | Ostroff et al. |
| 9,827,414 B2 | 11/2017 | Doerr et al. |
| 9,867,964 B2 | 1/2018 | Drake et al. |
| 9,899,778 B2 | 2/2018 | Hanson et al. |
| 9,907,952 B2 | 3/2018 | Sommer et al. |
| 9,907,953 B2 | 3/2018 | Orts et al. |
| 9,943,682 B2 | 4/2018 | Eggen et al. |
| 10,028,832 B2 | 7/2018 | Quill et al. |
| 10,046,167 B2 | 8/2018 | Schmidt et al. |
| 10,071,243 B2 | 9/2018 | Kuhn et al. |
| 10,080,887 B2 | 9/2018 | Schmidt et al. |
| 10,092,744 B2 | 10/2018 | Sommer et al. |
| 10,099,050 B2 | 10/2018 | Chen et al. |
| 10,105,535 B2 | 10/2018 | Regnier |
| 11,185,704 B2 | 11/2021 | Mar et al. |
| 2003/0065374 A1 | 4/2003 | Honeck |
| 2003/0114908 A1 | 6/2003 | Flach |
| 2004/0102830 A1 | 5/2004 | Williams |
| 2004/0127967 A1 | 7/2004 | Osypka |
| 2009/0118776 A1 | 5/2009 | Kelsch et al. |
| 2009/0234368 A1 | 9/2009 | Gore |
| 2010/0211149 A1 | 8/2010 | Morgan et al. |
| 2012/0116489 A1 | 5/2012 | Khairkhahan et al. |
| 2012/0158111 A1 | 6/2012 | Khairkhahan et al. |
| 2013/0331920 A1 | 12/2013 | Osypka |
| 2015/0025350 A1 | 1/2015 | Schnittker |
| 2015/0051612 A1 | 2/2015 | Schmidt et al. |
| 2015/0051614 A1 | 2/2015 | Schmidt et al. |
| 2016/0331325 A1 | 11/2016 | Munsinger et al. |
| 2016/0354600 A1 | 12/2016 | Kolberg et al. |
| 2017/0043155 A1 | 2/2017 | Marshall et al. |
| 2017/0072191 A1* | 3/2017 | Ma ................. A61N 1/3756 |
| 2017/0106185 A1 | 4/2017 | Orts et al. |
| 2017/0119555 A1 | 5/2017 | Bayer |
| 2017/0120042 A1 | 5/2017 | Becker et al. |
| 2017/0165454 A1 | 6/2017 | Tuohy et al. |
| 2017/0189669 A1 | 7/2017 | Kamarajugadda et al. |
| 2017/0239464 A1 | 8/2017 | Taeubert et al. |
| 2017/0252035 A1 | 9/2017 | Miraki |
| 2018/0071543 A1 | 3/2018 | Taff et al. |
| 2018/0133464 A1 | 5/2018 | Taeubert et al. |

(56) References Cited

U.S. PATENT DOCUMENTS

| | | |
|---|---|---|
| 2018/0207434 A1 | 7/2018 | Webb et al. |
| 2018/0221014 A1 | 8/2018 | Darabian |
| 2018/0236244 A1 | 8/2018 | Stevenson et al. |

FOREIGN PATENT DOCUMENTS

| | | |
|---|---|---|
| JP | 2013-540022 A | 10/2013 |
| JP | 2014-501584 A | 1/2014 |
| WO | 2006/045073 A1 | 4/2006 |
| WO | 2007/047681 A2 | 4/2007 |
| WO | 2012/051235 A1 | 4/2012 |

OTHER PUBLICATIONS

Office Action from related European Application No. 21195646.1, mailed on Oct. 5, 2022, 4 pages.

Notification of Grounds for Rejection (Office Action) from related Japanese Patent Application No. 2020-526292 mailed on Jun. 15, 2021 (8 pages including translation).

PCT International Search Report and Written Opinion from related PCT Patent Application No. PCT/US2018/059263, mailed on Jan. 31, 2019, 11 pages.

PCT International Preliminary Report on Patentability from related PCT Patent Application No. PCT/US2018/059263, mailed on May 22, 2020, 8 pages.

Extended European Search Report from related EP Application No. 21195646.1 mailed on Jan. 10, 2022 (5 pages).

Extended European Search Report from related EP Application No. 23180009.5 mailed on Oct. 4, 2023 (7 pages).

Extended European Search Report from related European Patent Application No. 24204366.9, mailed on Jan. 23, 2025, 5 pages.

Li, Jun et al. "Study on Application of Spiral Electrodes in Right Ventricular Outflow Tract Septal Pacing", Practical Journal of Cardiac Cerebral Pneumal and Vascular Disease (PJCCPVD), May 25, 2011, vol. 19, No. 5, pp. 728-730 (7 total pages including translation).

Notification of Decision to Grant and Supplementary Search Report from related Chinese Patent Application No. 201880085098.1, mailed on Jan. 29, 2024, 9 pages including translation.

Poon, A. S. Y. "Future implantable systems," 2011 IEEE Technology Time Machine Symposium on Technologies Beyond 2020, Hong Kong, China, 2011, pp. 1-1, doi: 10.1109/TTM.2011.6005173.

* cited by examiner

BIOSTIMULATOR HAVING FIXATION ELEMENT

This application is a continuation of co-pending U.S. patent application Ser. No. 17/513,794, filed on Oct. 28, 2021, which is a continuation of U.S. patent application Ser. No. 16/181,154, filed on Nov. 5, 2018, now issued as U.S. Pat. No. 11,185,704, which claims the benefit of priority of U.S. Provisional Patent Application No. 62/582,125, filed on Nov. 6, 2017, U.S. Provisional Patent Application No. 62/637,257, filed on Mar. 1, 2018, U.S. Provisional Patent Application No. 62/646,247, filed on Mar. 21, 2018, U.S. Provisional Patent Application No. 62/700,112, filed on Jul. 18, 2018, and U.S. Provisional Patent Application No. 62/750,034, filed on Oct. 24, 2018, each of which is incorporated herein by reference in its entirety to provide continuity of disclosure.

BACKGROUND

Field

The present disclosure relates to biostimulators. More specifically, the present disclosure relates to leadless biostimulators having tissue anchors.

Background Information

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. Pulse generator parameters are usually interrogated and modified by a programming device outside the body, via a loosely-coupled transformer with one inductance within the body and another outside, or via electromagnetic radiation with one antenna within the body and another outside. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Pacemaker leads can be fixed to an intracardial implant site by an engaging mechanism such as an anchor. For example, the anchor can screw into the myocardium.

SUMMARY

Although more than one hundred thousand conventional cardiac pacing systems are implanted annually, various well-known difficulties exist, of which a few will be cited. For example, a pulse generator, when located subcutaneously, presents a bulge in the skin that patients can find unsightly, unpleasant, or irritating, and which patients can subconsciously or obsessively manipulate or "twiddle." Even without persistent manipulation, subcutaneous pulse generators can exhibit erosion, extrusion, infection, disconnection, insulation damage, or conductor breakage at the wire leads. Although sub-muscular or abdominal placement can address some concerns, such placement involves a more difficult surgical procedure for implantation and adjustment, which can prolong patient recovery.

A conventional pulse generator, whether pectoral or abdominal, has an interface for connection to and disconnection from the electrode leads that carry signals to and from the heart. Usually at least one male connector molding has at least one terminal pin at the proximal end of the electrode lead. The male connector mates with a corresponding female connector molding and terminal block within the connector molding at the pulse generator. Usually a setscrew is threaded in at least one terminal block per electrode lead to secure the connection electrically and mechanically. One or more O-rings usually are also supplied to help maintain electrical isolation between the connector moldings. A setscrew cap or slotted cover can be included to provide electrical insulation of the setscrew. This briefly described complex connection between connectors and leads provides multiple opportunities for malfunction.

Other problematic aspects of conventional pacing systems relate to the separately implanted pulse generator and pacing leads. By way of another example, the pacing leads, in particular, can become a site of infection and morbidity. Many of the issues associated with conventional biostimulators, such as cardiac pacemakers, are resolved by the development of a self-contained and self-sustainable biostimulator, or so-called leadless biostimulator. The leadless biostimulator can be attached to tissue within a dynamic environment, e.g., within a chamber of a beating heart.

According to a first aspect of the invention a biostimulator comprises a housing having a longitudinal axis and containing an electronics compartment; and a fixation element mounted on the housing, wherein the fixation element includes a helix extending along a helical axis about the longitudinal axis to a distal edge, wherein the distal edge extends around the helical axis and defines one or more helix faces on the helical axis, wherein a transverse plane orthogonal to the longitudinal axis intersects a center of the one or more helix faces, and wherein the helix includes a leading point on the helix face proximal to the transverse plane.

Advantageously, the helix can include an ellipsoidal outer surface extending around the helical axis. Moreover, the distal edge can be at an intersection between the ellipsoidal outer surface and the one or more helix faces. Further, the leading point can be on the distal edge.

Furthermore, it can be intended that a longitudinal plane can intersect and be orthogonal to the transverse plane at the center of the one or more helix faces. Further, the leading point can be at a six o'clock position on the longitudinal plane.

In another advantageous embodiment of the invention the six o'clock position can be on the distal edge.

Advantageously, the one or more helix faces can include a plurality of bevel faces converging at the leading point. Moreover, the plurality of bevel faces can intersect along a leading edge extending from the leading point along the one or more helix faces to a base on the distal edge. Further, the base can be on an opposite side of the transverse plane from the housing.

It can be further intended that the biostimulator can further comprise a helix mount having a helix mount flange, wherein the helix mount flange can include one or more marks defining an alignment range. Moreover, the helix can extend distally from a distal end of the helix mount flange to the leading point. Further, the leading point can be aligned with the alignment range.

In another advantageous embodiment of the invention the one or more marks can be radiopaque such that the one or more marks are visible under fluoroscopy.

Furthermore, it is thereby possible that the alignment range can be between a leftward boundary and a rightward boundary of the one or more marks. Moreover, the helix can extend to the leading point that is vertically aligned with the alignment range.

Advantageously, the biostimulator can further comprise a plurality of backstop elements to resist backward movement of the housing when the fixation element is engaged in tissue.

It can be further intended that the plurality of backstop elements can include a non-metallic filament extending through a bore in a sidewall of the helix mount along a filament axis to a filament tip.

Advantageously, the filament tip can have a filament face on the filament axis. Moreover, the filament face can be at an angle to the filament axis.

Furthermore, it can be intended that the plurality of backstop elements can include a plurality of non-metallic filaments extending through respective bores in the sidewall. Further, each bore can be at a different longitudinal position relative to the longitudinal axis.

Advantageously, the non-metallic filament can include a natural fiber.

It can be further intended that the plurality of backstop elements can include a pinch point between the helix and the distal end of the helix mount flange.

Advantageously, the biostimulator can have a first removal torque when the fixation element is engaged in tissue and the tissue is not at the pinch point. Moreover, the biostimulator can have a second removal torque when the fixation element is engaged in the tissue and the tissue is at the pinch point. Further, the second removal torque can be at least 10% higher than the first removal torque.

Furthermore, it can be intended that the biostimulator can be a leadless cardiac pacemaker.

Advantageously, the biostimulator can further comprise an active helical electrode mounted on the housing. Moreover, the active helical electrode can include an electrode helix extending along an electrode helical axis about the longitudinal axis radially inward of the helical axis. Further, the electrode helical axis and the helical axis can revolve about the longitudinal axis in a same rotational direction.

According to a further aspect of the present invention a method is made available, which comprises mounting a helix mount on a housing, wherein the helix mount includes a helix mount flange, wherein the helix mount flange includes one or more marks defining an alignment range; and screwing a fixation element onto the helix mount, wherein the fixation element includes a helix extending along a helical axis, and wherein the helix is screwed onto the helix mount flange until a leading point of the helix is aligned with the alignment range.

Moreover, it is possible according to the present invention that the one or more marks can be radiopaque such that the one or more marks are visible under fluoroscopy.

Advantageously, the alignment range can be between a leftward boundary and a rightward boundary of the one or more marks. Moreover, the helix can extend over about 1.4 to about 1.6 turns of the helical axis to the leading point when the leading point is vertically aligned with the alignment range.

Furthermore, it is thereby possible that the method can further comprise inserting a non-metallic filament through a bore in a sidewall of the helix mount.

Advantageously, the helix mount can include a cap mounted distally on the helix mount, and the bore can be in the cap.

Moreover, it is possible according to the present invention that the helix can extend along the helical axis about a longitudinal axis of the housing to a distal edge. Moreover, the distal edge can extend around the helical axis and defines one or more helix faces on the helical axis. Further, a transverse plane orthogonal to the longitudinal axis can intersect a center of the one or more helix faces. Beyond that, the leading point can be proximal to the transverse plane.

Furthermore, it can be intended that the helix can include an ellipsoidal outer surface extending around the helical axis. Further, the distal edge can be at an intersection between the ellipsoidal outer surface and the helix face. Beyond that, the leading point can be on the distal edge.

Beyond that the method according to the invention can further comprise advancing a biostimulator to a target tissue, wherein the biostimulator can include a housing having a longitudinal axis and containing an electronics compartment, and a fixation element can be mounted on a helix mount flange of the housing, wherein the fixation element can include a helix extending from a distal end of the helix mount flange to a leading point, wherein the helix mount flange can include one or more radiopaque marks defining an alignment range, and wherein the leading point can be aligned with the alignment range, viewing the one or more radiopaque marks under fluoroscopy and rotating the biostimulator until the fluoroscopically viewed one or more radiopaque marks complete a predetermined number of turns.

Advantageously, the predetermined number of turns can be about 1.5 turns.

In the following, the invention is described in more detail, whereby all features of the following description may refer to the previously listed explanations.

A biostimulator for implantation within a heart of a patient can be provided. Preferably, the biostimulator is a leadless biostimulator. In an embodiment, the biostimulator can comprise an electronics compartment. Additionally or alternatively the biostimulator can include a housing containing an energy source, e.g., a battery, an ultracapacitor, or an energy harvester, and the housing can have a longitudinal axis. Additionally or alternatively the biostimulator can include a housing comprising electronic circuitry and an energy source. The biostimulator can include a fixation element mounted on the housing. For example, the fixation element can be a helix, formed from a wire, that extends about the longitudinal axis to a leading point. The leading point can penetrate tissue to anchor the biostimulator within the heart. Additionally or alternatively the leading point can be on a helix face that intersects an outer surface of the wire along a distal edge. Additionally or alternatively the leading point can be on the wire face at a location that controls a depth of penetration of the wire when the fixation element is screwed into target tissue. For example, the leading point can be on the wire face between a center of the wire face and the housing, e.g., proximally located at a six o'clock position on the distal edge. When the leading point is at the six o'clock position, the fixation element may penetrate more shallowly than when the leading point is at a twelve o'clock position diametrically opposite the six o'clock position on the distal edge. It has been discovered that shallow penetration can be useful when anchoring in tissue substrates, and more particularly, when anchoring in anatomical structures that are layered. For example, when several tissue substrates are immediately adjacent, such as in the case of the atrium covered by the pericardial sac, limiting penetration depth of the leading point can reduce a likelihood of injury and can improve device performance. The leading point can be between a transverse plane and the housing to cause fixation element to penetrate less deeply into target tissue. More particularly, leading point can be proximal to the transverse plane. By contrast, leading point can be on an opposite side of transverse plane from housing, e.g., distal to the transverse plane, to cause fixation element to penetrate more deeply into the target tissue. Transverse plane can be orthogonal to longitudinal axis (or helix axis) and may extend along a median line of wire face. More particularly, transverse plane can intersect a center of wire face. Accordingly, transverse plane can define a longitudinally located separator between a portion of wire face that is proximal-most (the surface area that is between transverse plane and housing) and a portion of wire face that is distalmost (the surface area that is on an opposite side of transverse plane from housing). The fixation element can include a helix extending along a helical axis to a helix face.

The biostimulator can optionally include several backstop elements to resist backward movement of the housing when the fixation element is engaged in tissue. For example, the backstop elements can include non-metallic filaments that extend outward from a helix mount that holds the fixation element. The filaments can be sutures, natural fibers, etc., which engage the tissue in an opposite direction from the fixation element, and thus, increase a back-out torque required to dislodge the biostimulator from the tissue.

The backstop elements can include a pinch point between the wire and the helix mount. More particularly, when the fixation element is screwed into the tissue by a predetermined amount, e.g., 1.5 turns, the tissue can be clamped between the wire and the helix mount at the pinch point. The clamping and/or scarring caused by the pinch point can further secure the biostimulator within the dynamic operating environment.

The biostimulator can include one or more marks that facilitate proper assembly of the fixation element. More particularly, the one or more marks can have boundaries that define an alignment range, and placement of the leading point within the alignment range during assembly can ensure that tissue is captured at the pinch point when the fixation element is screwed into the tissue by the predetermined amount, e.g., 1.5 turns. In an aspect, the marks can be used during manufacturing by screwing the fixation element onto the helix mount until the leading point is vertically aligned between a leftward boundary and a rightward boundary. The mark(s) can also enable accurate implantation in a clinical setting.

For example, one or more of the mark(s) may be radiopaque, and thus, can be visible under fluoroscopy or using another imaging modality. The radiopaque mark(s) can be viewed during a clinical implantation of the biostimulator to assess a degree of rotation of the fixation element into the target tissue. For example, an operator can advance the biostimulator to the target tissue, view the radiopaque mark(s) under fluoroscopy, and rotate the biostimulator until the fluoroscopically viewed mark(s) complete a predetermined number of turns. The number of turns can be a nominally recommended number, e.g., 1.5 turns. Alternatively, the number of turns can be fewer than the nominally recommended number, e.g., 1 turn, when the tissue strength is known or expected to be degraded such as when the tissue is friable, the tissue is in a diseased state, or the patient has had prior cardiac surgeries or procedures. Under-rotation (as compared to a nominal recommended rotation) may be beneficial in tissue that is not able to withstand the increase in torque that occurs as a device is rotated toward and beyond the pinch point.

In an embodiment, the biostimulator can comprise an active helical electrode nestled within a helical fixation element. Both helices may provide active fixation for the biostimulator. In certain embodiments, the wind direction can be the same for both helices.

The above summary does not include an exhaustive list of all aspects of the present invention. It is contemplated that the invention includes all devices, in particular the biostimulator, systems and methods, in particular the method comprising mounting a helix mount on a housing, that can be practiced from all suitable combinations of the various aspects summarized above, as well as those disclosed in the Detailed Description below and particularly pointed out in the claims filed with the application. Such combinations have particular advantages not specifically recited in the above summary. Here, features, which are described in conjunction with the biostimulator, apply, of course also in conjunction with the method according to the invention, and vice versa, so that, with respect to the disclosure, reference is or can mutually be made to the individual aspects of the invention.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
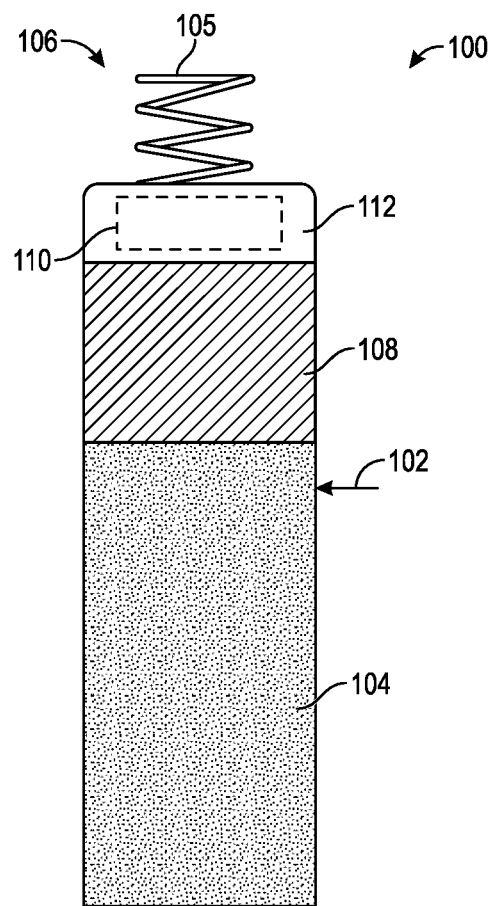
FIG. 1 illustrates a biostimulator in accordance with the present disclosure.

Embodiments describe a biostimulator, e.g., a leadless cardiac pacemaker, having a fixation element that is mounted on a housing and includes a helix extending to a leading point for piercing tissue. More particularly, the wire can extend along a helical axis to a distal edge defining a helix face. The leading point can be on the wire face between a center of the wire face and the housing. The biostimulator may be used to pace cardiac tissue as described below. The biostimulator may be used in other applications, such as deep brain stimulation, and thus, reference to the biostimulator as being a cardiac pacemaker is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a longitudinal axis of a biostimulator housing. Similarly, "proximal" may indicate a second direction opposite to the first direction. Such terms are provided to establish relative frames of reference, however, and are not intended to limit the use or orientation of a biostimulator to a specific configuration described in the various embodiments below.

In an aspect, a biostimulator is provided. The biostimulator includes a fixation element to engage tissue for anchoring the biostimulator within a patient anatomy. The fixation element can include a helix extending along a helical axis to a helix face. A leading point of the wire can be on the wire face between a center of the wire face and a housing of biostimulator. Accordingly, the leading point can be within a proximal portion of the wire face. The proximally located leading point may pierce tissue more shallowly than a comparative leading point located distal to the center of the wire face. As a result, the fixation element may be less likely to extend fully through a target tissue.

In an aspect, a biostimulator optionally includes backstop elements to resist backward movement of the fixation element and/or housing of the biostimulator when the fixation element is engaged in tissue. The backstop elements can include non-metallic filaments extending outward from a mounting helix on the housing. The non-metallic filaments can resist back-out of the fixation element by grabbing tissue when the helical wire of the fixation element unscrews from the target tissue. Furthermore, the backstop elements can include a pinch point between the wire of the fixation element and a distal end of the helix mount. When the fixation element is screwed into the target tissue, the tissue can wedge between the fixation element and the helix mount at the pinch point, causing the biostimulator to clamp onto the tissue. The clamping force can resist back-out of the fixation element.

In an embodiment, the biostimulator includes one or more marks on the helix mount that define an alignment range for the leading point of the fixation element. More particularly, the fixation element can be screwed onto the helical helix mount until the leading point is aligned with the alignment range between the one or more marks. When so aligned, the wire can extend over about 1.5 turns to the leading point. Set in such a fashion, the fixation element provides anchoring in the target tissue, and the tissue can be clamped by the pinch point to resist back-out.

Various embodiments of a system including one or more leadless biostimulators, e.g., leadless cardiac pacemakers, are described. For example, the system can be a cardiac pacing system having a leadless cardiac pacemaker. The leadless pacemaker can be substantially enclosed in a hermetic housing suitable for placement on or attachment to the inside or outside of a cardiac chamber. The pacemaker can have two or more electrodes located within, on, or near the housing, for delivering pacing pulses to muscle of the cardiac chamber and optionally for sensing electrical activity from the muscle, and for bidirectional communication with at least one other device within or outside the body. The housing can contain a primary energy source, e.g., a battery, to provide power for pacing, sensing, and communication (for example, bidirectional communication). The housing can optionally contain electric circuits. For example, the housed electric circuits can be for sensing cardiac activity from the electrodes. The housing can contain circuits for receiving information from at least one other device via the electrodes and contains circuits for generating pacing pulses for delivery via the electrodes. For example, a pulse generator can be hermetically contained within the housing of the leadless pacemaker and electrically connected to at least first and second electrodes of the leadless pacemaker. The pulse generator can be configured to generate and deliver electrical pulses via at least the first and second electrodes to cause cardiac contractions. The housing can optionally contain circuits for transmitting information to at least one other device via the electrodes and can optionally contain circuits for monitoring device health. The housing contains circuits for controlling these operations in a predetermined manner.

In some embodiments, a cardiac pacemaker can be adapted for implantation into tissue in the human body. In a particular embodiment, a leadless cardiac pacemaker can be adapted or configured for implantation in at least one cardiac chamber of a patient, e.g., adjacent to heart tissue on the inside or outside wall of the cardiac chamber. The leadless cardiac pacemaker can be configured for leadless cardiac pacing, e.g., the leadless pacemaker can use two or more electrodes located on or within the housing of the pacemaker to pace the cardiac chamber upon receiving a triggering signal from at least one other device within the body. Self-contained or leadless pacemakers or other biostimulators can be fixed to an intracardial implant site by an actively engaging mechanism such as a screw or helical member that screws into the myocardium.

FIG. 1 shows a biostimulator 100. The biostimulator 100 can be a leadless biostimulator, e.g., a leadless cardiac pacemaker, for example. The biostimulators can include a hermetic housing 102 with electrodes 104 and 106 disposed thereon. The electrodes can be integral to the housing 102, or connected to the housing at a maximum distance of 2 centimeters from the housing. Housing 102 can optionally contain an energy source (not shown) to provide power to the pacing electrodes 104, 106. The energy source can be a battery, such as a lithium carbon monofluoride (CFx) cell, or a hybrid battery, such as a combined CFx and silver vanadium oxide (SVO/CFx) mixed-chemistry cell. Similarly, the energy source can be an ultracapacitor. In an embodiment, the energy source can be an energy harvesting device, such as a piezoelectric device that converts mechanical strain into electrical current or voltage.

In certain embodiments, the energy source can be located outside of the housing. For example, the energy needed to power the electrical circuits could come from an ultrasound transducer and receiver, which receive ultrasound energy from an ultrasound transmitter located outside of the housing.

As shown, electrode 106 can be disposed on or integrated within a fixation element 105, and the electrode 104 can be disposed on the housing 102. The fixation element 105 can be mounted on housing 102, as described below. Fixation element 105 can be a fixation helix or other flexible or rigid structure suitable for attaching the housing 102 to tissue, such as heart tissue. Fixation element 105 may alternately be referred to as a primary fixation element, a primary fixation helix, a fixation helix, a primary helix, or similar. Such terminology may serve to distinguish from other, secondary, fixation elements that resist dislodgement of primary fixation element 105 after it has attached the housing 102 to tissue. In other embodiments, the electrode 106 may be independent from the fixation element in various forms and sizes. The housing can also include an electronics compartment 110 within the housing that contains the electronic components necessary for operation of the biostimulator. By co-locating the stimulation electrode with the pacing generator, and by reducing the pulse generator size to fit within the heart, the biostimulator can be leadless. The hermetic housing can be adapted to be implanted on or in a human heart, and can be cylindrically shaped, rectangular, spherical, or any other appropriate shapes, for example.

The housing can include a conductive, biocompatible, inert, and anodically safe material such as titanium, 316L stainless steel, or other similar materials. The housing can further include an insulator 108 disposed on the conductive material to separate electrodes 104 and 106. The insulator can be an insulative coating on a portion of the housing between the electrodes, and can include materials such as silicone, polyurethane, parylene, or another biocompatible electrical insulator commonly used for implantable medical devices. In the embodiment of FIG. 1, a single insulator 108 is disposed along the portion of the housing between electrodes 104 and 106. In some embodiments, the housing itself can include an insulator instead of a conductor, such as an alumina ceramic or other similar materials, and the electrodes can be disposed upon the housing.

As shown in FIG. 1, the biostimulator can further include a header assembly 112 to isolate electrode 104 from electrode 106. The header assembly 112 can be made from tecothane or another biocompatible plastic, and can contain a ceramic to metal feedthrough, a glass to metal feedthrough, or other appropriate feedthrough insulator.

The electrodes 104 and 106 can include pace/sense electrodes, or return electrodes. A low-polarization coating can be applied to the electrodes, such as platinum, platinum-iridium, iridium, iridium-oxide, titanium-nitride, carbon, or other materials commonly used to reduce polarization effects, for example. In FIG. 1, electrode 106 can be a pace/sense electrode and electrode 104 can be a return electrode. The electrode 104 can be a portion of the conductive housing 102 that does not include an insulator 108.

Several techniques and structures can be used for attaching the housing 102 to the interior or exterior wall of the heart. A fixation element 105, which can be a helical fixation element, can enable insertion of the device endocardially or epicardially through a guiding catheter. A torqueable catheter can be used to rotate the housing and force the fixation element into heart tissue, thus affixing the fixation element (and also the electrode 106 in FIG. 1) into contact with stimulable tissue. Electrode 104 can serve as an indifferent electrode for sensing and pacing. The fixation element may be coated partially or in full for electrical insulation, and a steroid-eluting matrix may be included on or near the device to minimize fibrotic reaction.

Biostimulator 100 may be used in a dynamic environment. For example, biostimulator 100 can be a leadless cardiac pacemaker placed within the dynamic environment of a beating heart, e.g., within an atrium or a ventricle of the heart. When fixation element 105 is engaged with the contracting and relaxing heart tissue, forces can be applied to biostimulator 100 that may promote dislodgement, e.g., unscrewing, of the fixation element 105. Accordingly, in certain embodiments, a likelihood of dislodgement of biostimulator 100 may be reduced by incorporating anti-unscrewing features in biostimulator 100 that resist dislodgement.

Biostimulator 100 can include one or more backstop elements (FIG. 2), which can include various anti-unscrewing features on the biostimulator. The backstop elements are optional, e.g., biostimulator 100 can have fixation element 105 in accordance with this description without having backstop elements. The backstop elements can require that the torque necessary to unscrew the biostimulator from tissue is greater than the torque necessary to unscrew the biostimulator without such a feature. The backstop elements may also be referred to as secondary fixation elements because the backstop elements grab tissue to provide resistance to back-out or rotation in an opposite direction to the rotation required to engage tissue with fixation element 105. Backstop elements, anti-unscrewing features, or secondary fixation elements, as alternately referred to below, can include sutures, whiskers, or other means of resisting, preventing, or stopping backward movement of housing 102 when fixation element 105 is engaged in tissue. For example, a backstop element can include a functional interaction between several components of biostimulator 100, e.g., between fixation element 105 and housing 102, that pinches or clamps heart tissue to resist dislodgement of biostimulator 100 under dynamic conditions.

In some embodiments, the torque necessary to unscrew the biostimulator from tissue is greater than the torque necessary to further screw, engage, or re-engage the fixation element 105 of the biostimulator 100 into tissue. When a backstop element provides this function, the chances of a biostimulator accidentally unscrewing or disengaging itself from the tissue is reduced. It should be noted that the torque necessary to initially insert a biostimulator into tissue is greater due to the puncturing or piercing of tissue and the formation of a helical cavity. Thus, in some embodiments, the anti-unscrewing features need only provide that the torque necessary to unscrew the biostimulator from tissue be greater than the torque necessary to unscrew the biostimulator from tissue after the biostimulator has already been implanted in tissue (i.e., after the tissue has been pierced).

The effectiveness of biostimulator anti-unscrewing features may vary depending on the fixation location of the biostimulator within the heart and, more specifically, the shape of the tissue surrounding the fixation location. For example, each of the ventricular walls tends to define a generally conical volume with the septum that tapers from the atrioventricular valve to the apex of the heart. During beating of the heart, contraction of the ventricular walls causes the distance between the walls and the septum to narrow, particularly in the region closest to the apex. Such narrowing may result in the ventricular walls and/or the septum laterally contacting a biostimulator fixed near the apex. As a result, anti-unscrewing features extending laterally from the biostimulator can provide sufficient anti-unscrewing performance to maintain fixation of biostimulators within the apical region of the ventricles.

In comparison to the generally conical/tapering shape of the ventricles, the atrial walls tend to define substantially rounder cavities such that an atrial region in which a similar narrowing effect observed between the ventricular walls and the septum is not generally present. Rather, the surface of the atrial walls remains substantially flat throughout contraction of the atria. As a result, biostimulators fixed within the atria are essentially flush mounted with the atrial wall such that laterally extending anti-unscrewing features may not engage the atrial wall and may not resist unscrewing of the biostimulator.

In light of the foregoing, biostimulators in accordance with this disclosure can include lateral or forward facing backstop elements that provide anti-unscrewing functionality even when the biostimulator is substantially flush mounted with cardiac tissue. More specifically, biostimulators in accordance with this disclosure can include one or more backstop elements disposed on a forward face of the biostimulator adjacent a primary fixation element, such as a helical screw. For example, the backstop element(s) can include a non-metallic filament, such as a suture, extending in a lateral or forward direction from a distal region of biostimulator 100. The sutures are oriented in a direction at least partly opposite the primary fixation mechanism such that after fixation of the biostimulator by rotation in a first direction, counter rotation causes the sutures to engage tissue adjacent the primary fixation mechanism, thereby resisting further counter rotation.

In certain embodiments, such as for the atrium, the biostimulator only includes lateral or forward-facing back-up elements.

In certain embodiments, the biostimulator includes both side and forward-facing back-up elements, in order to configure the biostimulator to be implanted in either an atrium or ventricle.

In certain implementations, the sutures are formed of a flexible material such that sufficient counter rotational force applied to the biostimulator may cause the sutures to bend and disengage from the tissue adjacent the primary fixation. As a result, the biostimulator may be removed or repositioned from the fixation site with minimal damage to tissue at the fixation site. Disengagement of one or more of the sutures may also be controlled by positioning the sutures such that bending of the sutures during counter rotation is obstructed by the primary fixation mechanism/helical screw. Other aspects of the present disclosure are directed to specific arrangements of sutures and methods of coupling the sutures to the biostimulator housing.

It will be appreciated by one skilled in the art that pacemaker helices can be terminated in a sharpened tip to facilitate initial puncturing and subsequent penetration into cardiac tissue. The sharpened tip can be formed at the distal extent of the helix with the sharpened tip forming a leading portion of the helix. Such tip arrangements may have good tissue engagement and fixation characteristics, however, placement of the sharpened tip on the distalmost edge of the helix may increase the likelihood that the helix will penetrate through the heart wall, particularly in thinner walled portions of the heart such as the atrium. In certain cases, penetration by the helix may result in unfavorable interaction with the pericardium and complications such as cardiac tamponade. In certain cases, for example, the helix may be screwed through the pericardium to the extent that it pierces the aorta.

Figure 27A:
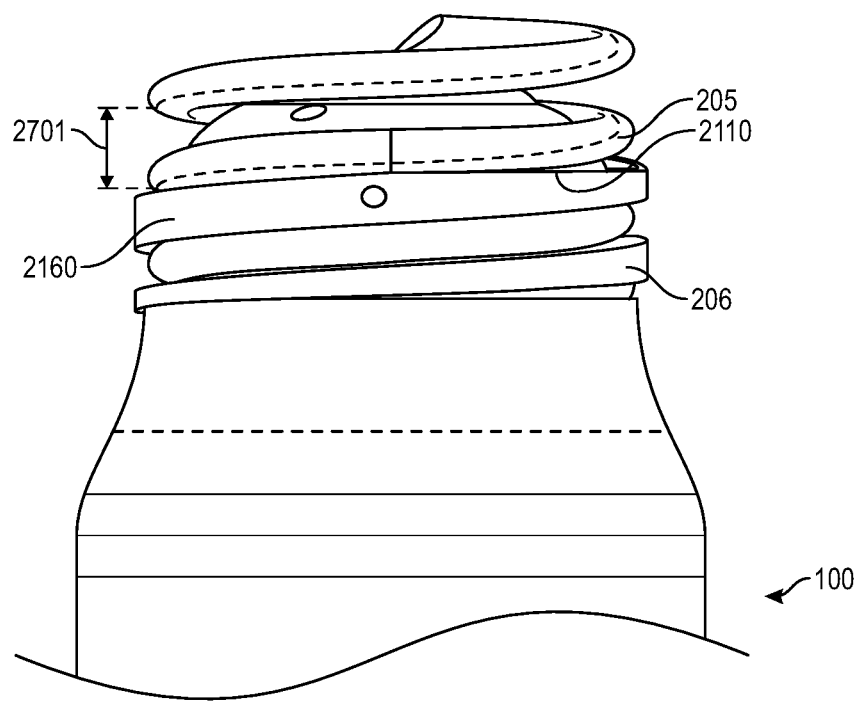
FIGS. 27A and B are pictorial views of biostimulator features that have an effect on penetration depth in accordance with the present disclosure.

Referring to FIG. 27A, biostimulator 100 can have several features that affect anchoring of the device in the target tissue. For example, a pitch 2701 defines a gap between helical turns within which tissue can be captured during implantation. The gap can affect the anchoring, e.g., by controlling a surface area to tissue ratio, and can also be a variable in determining how deep the anchor penetrates.

Figure 27B:
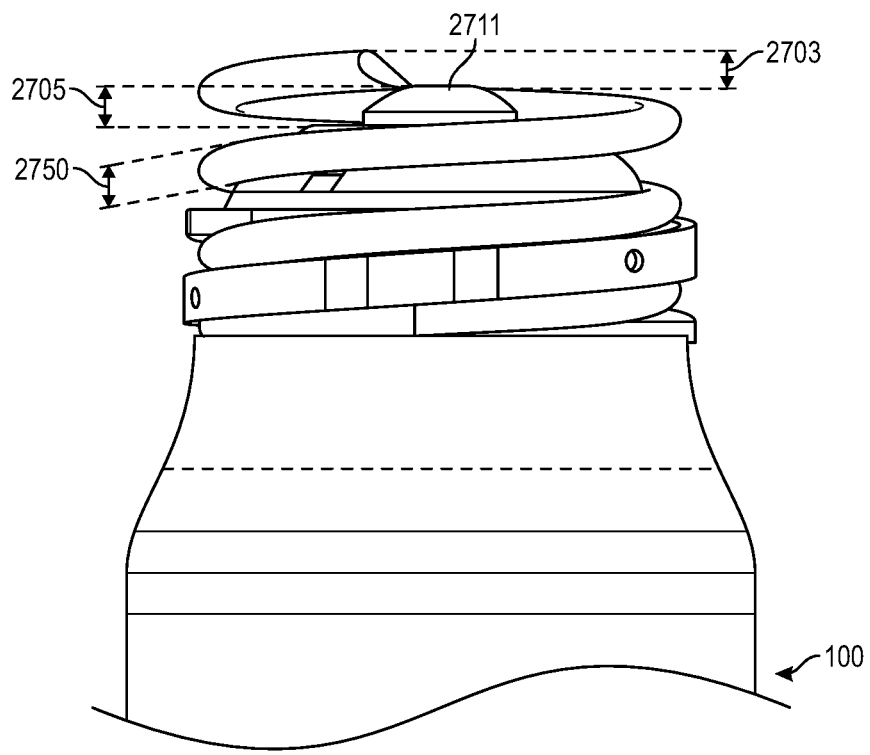

Referring to FIG. 27B, similarly, a projection 2703 of the leading point of the anchor beyond a distal end of the biostimulator 100 can affect anchoring by determining how deep the helix will penetrate during implantation. In certain embodiments, the tip does not stand proud of the helix mount greater than tissue. In certain embodiment, the maximum projection 2703 is 1.5 mm. An interference 2705 between the distal end of the biostimulator, e.g., the distal end of an electrode 2711, and the helix proximal to the electrode can affect how much back pressure is placed on the device by the target tissue, and thus, how well the device anchors. This is the distance between the distal end of the electrode and the distal end of the helix mount.

Referring again to FIG. 27A, as described below, a placement of a tissue pinch point 2110 can affect how well tissue is gripped by the pinch point, and thus, how well the device is anchored to the tissue. Several or all of these variables can be codependent, and can be affected by a number of turns of the helical anchor beyond the pinch point. More particularly, the number of turns can be a variable, which in combination with the other codependent variables, determines how well the device anchors to target tissue and a degree of injury to the target tissue. Accordingly, the number of turns correlates to a degree of clinical risk, e.g., how likely the implanted device is to dislodge from the target tissue and how likely the implanted device is to cause injury to the target tissue.

Referring again to FIG. 27B, in an embodiment, the primary helix 205 can have a wire diameter 2750 from and including 0.003 inches to and including 0.03 inches. The primary helix 205 can have a pitch diameter from and including 0.06 inches to and including 0.3 inches. Pitch 2701 can be from and including 0.01 inches to and including 0.05 inches. The projection 2703 of the leading point of the anchor beyond a distal end of the biostimulator 100 can be 0-1.5 mm. The interference 2705 between the distal end of electrode 2711 and the helix proximal to the electrode can be 0-1.5 mm.

In certain embodiments, the tissue pinch point 2110 tissue is wedged at the pinch point 2110 during implant, as described herein by turning the helix 1.5 turns. As described herein, the operator may, however, turn biostimulator 100 to a more or lesser degree depending on the particular patient. For example, when the patient has friable tissue, the operator may choose to rotate biostimulator 200 by 1.25 turns instead of 1.5 turns.

Figure 28:
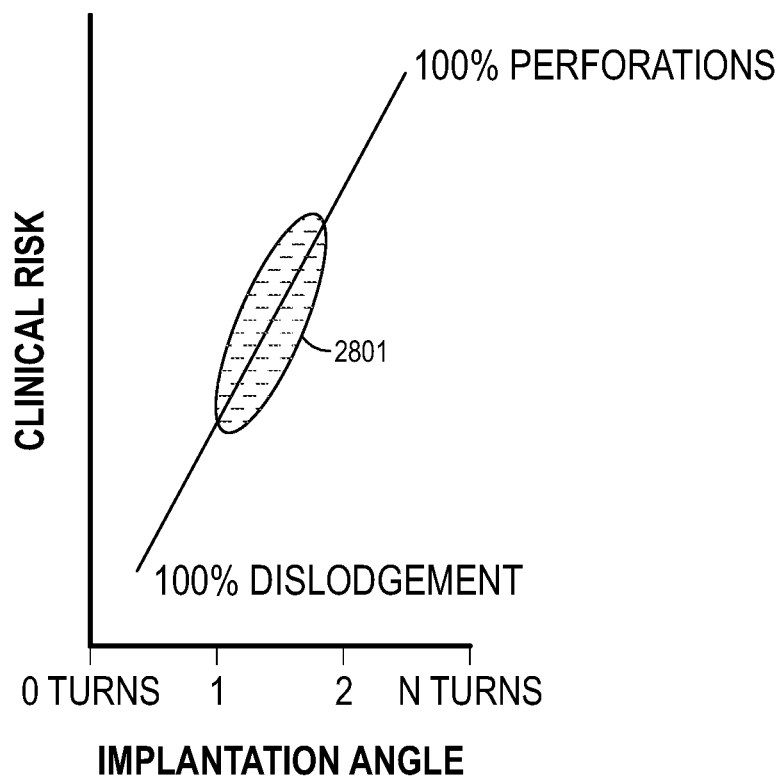
FIG. 28 is a graphical view of implantation angle versus implantation risks in accordance with the present disclosure.

Referring to FIG. 28, a graph of device implantation angle versus clinical risk is shown. A range 2801 is shown which balances a risk of dislodgement of a device after implantation against a risk of perforating tissue, e.g., the pericardial sac. In an embodiment, the range 2801 is a range of turns in which a balance between the risks is effectively minimized. For example, when an implantation angle is between 1-2 turns of the device during implantation, an acceptable level of risk of dislodgement and injury may be achieved. Accordingly, rotating the fixation element 1.5 turns into the target tissue can provide acceptable anchoring and an acceptably low risk of perforation. The implantation angle can depend on the multiple, codependent variables described above, as well as additional variables such as a placement of a leading point of the fixation element, as described below.

Figure 33:
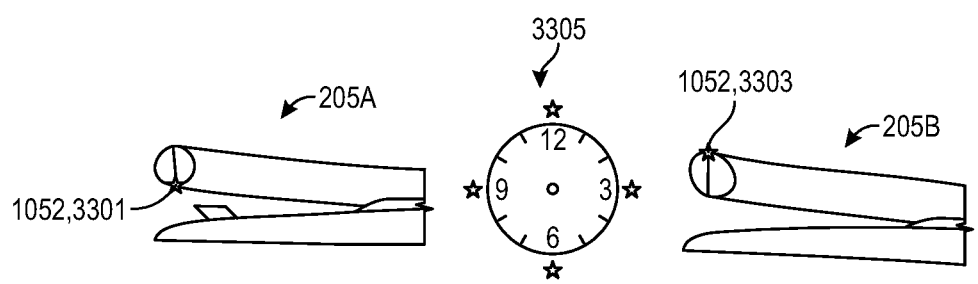
FIG. 33 is a pictorial view of a primary helix having a leading point at six o'clock position, and a primary helix having a leading point at a twelve o'clock position, in accordance with the present disclosure.

In an embodiment, the tips of biostimulators in accordance with this disclosure may be oriented to facilitate engagement and retention of the biostimulators within cardiac tissue while reducing the likelihood of excessive trauma to the heart. As described above, shallow penetration of the fixation element 105 can be advantageous in certain anatomical environments. Furthermore, the depth of penetration can depend on a clocking of a leading tip of the fixation element 105. The clocking concept is referred to throughout the following description, and thus, an introduction to the concept is provided here. Referring to FIG. 33, a pictorial view of a primary helix 205A having a leading point 1052 at six o'clock position 3301, and a primary helix 205B having a leading point 1052 at a twelve o'clock position 3303, are shown side by side for comparison purposes. The positions of the leading point 1052 can be understood with reference to a clock 3305. The clock 3305 can have a twelve o'clock location at the top of the clock, which can correspond to a distalmost location in relation to the longitudinal axis 304. Similarly, the six o'clock location at the bottom of the clock can correspond to a proximalmost location in relation to the longitudinal axis 304. Accordingly, the six o'clock position 3301 can be longitudinally proximal to the twelve o'clock position 3303. Following along with the concept, the leading point 1052 may alternatively be at a nine o'clock position (FIG. 12A) corresponding to a nine o'clock location at the left of the clock, or the leading point 1052 may be at a three o'clock position (not shown) corresponding to a three o'clock location at the right of the clock.

Figure 29:
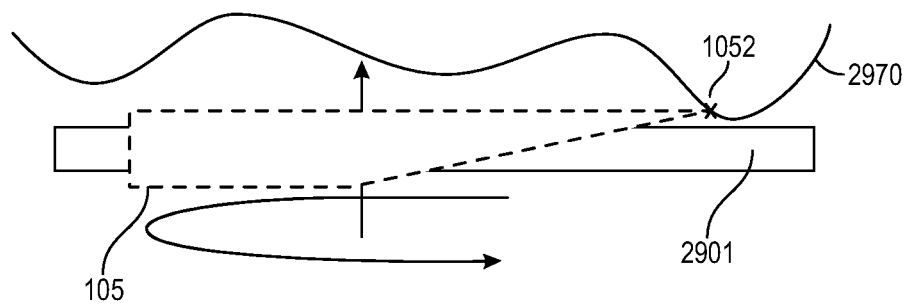
FIG. 29 is a pictorial view of a fixation element having a leading point in a twelve o'clock position penetrating tissue in a layered tissue environment, in accordance with the present disclosure.

Referring to FIG. 29, a pictorial view of a fixation element penetrating tissue in a layered tissue environment is shown in accordance with the present disclosure. The layered tissue environment can include a myocardium 2901, e.g., the tissue wall of a right atrial appendage, and a pericardium 2970, e.g., the tissue of a pericardial sac covering the right atrial appendage. In such case, the myocardium 2901 may be 1-2 mm thick, and thus, the leading point 1052 of the fixation element 105 can penetrate the myocardium 2901 and puncture entirely through the thin wall, as shown.

It has been discovered that the leading point 1052 in the twelve o'clock position may actually exit the myocardium and grip the pericardium 2970. In some cases, the leading point 1052 can puncture the pericardial sac, or pull the pericardial sac against the myocardium, i.e., pin the pericardial sac to the myocardium. In either case, damage to the pericardium and injury to the patient can result.

Figure 30:
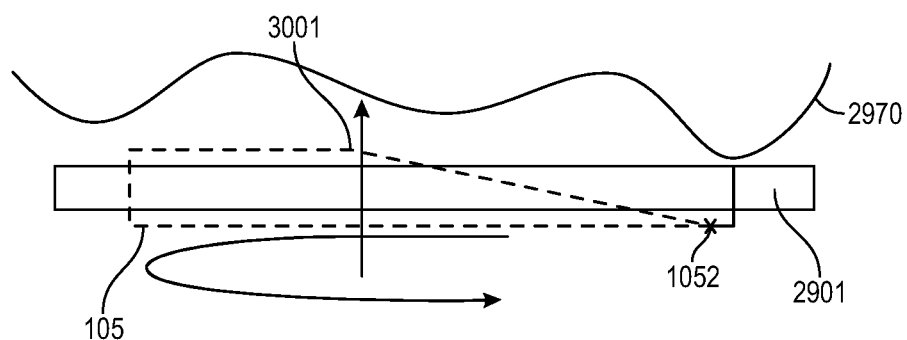
FIG. 30 is a pictorial view of a fixation element having a leading point in a six o'clock position penetrating tissue in a layered tissue environment, in accordance with the present disclosure.

Referring to FIG. 30, a pictorial view of a fixation element having a leading point 1052 in a six o'clock position penetrating tissue in a layered tissue environment is shown in accordance with the present disclosure. The fixation element 105 can have the leading point 1052 at the six o'clock position, which can reduce a risk of pinning the pericardial sac. More particularly, the leading point 1052 can penetrate more shallowly, and thus, may not penetrate fully through the myocardium 2901. Even if the leading point 1052 does pass through the myocardium 2901, a distal trailing edge 3001 of the fixation element 105, which is distal to the leading point 1052, in the twelve o'clock position can shield the leading point 1052 from the pericardium 2970. For example, in contrast to the leading point 1052, the trailing edge 3001 may not grip the pericardial sac even when exposed to the pericardium. Accordingly, placement of the leading point 1052 at the six o'clock position can avoid contact between the leading point 1052 and the pericardium 2970 and can reduce a likelihood of pericardial pinning and patient injury. Device performance can be therefore be improved by locating the leading point at the six o'clock position.

To address the foregoing issues regarding penetration of the primary fixation helix, implementations of the present disclosure include primary fixation helices in which the sharpened tip is disposed away from the distalmost edge of the helix. For example, in certain implementations, the sharpened tip may be disposed opposite the distalmost edge at the end of the helix (at the six o'clock position). By doing so, the likelihood of overpenetration by the helix through a cardiac is wall reduced. However, should the helix penetrate through the cardiac wall, the sharpened tip is biased away from the adjacent pericardium because the trailing edge rides over the pericardium 2970, thereby reducing the likelihood that the helix will engage and perforate the pericardial tissue.

Figure 2:
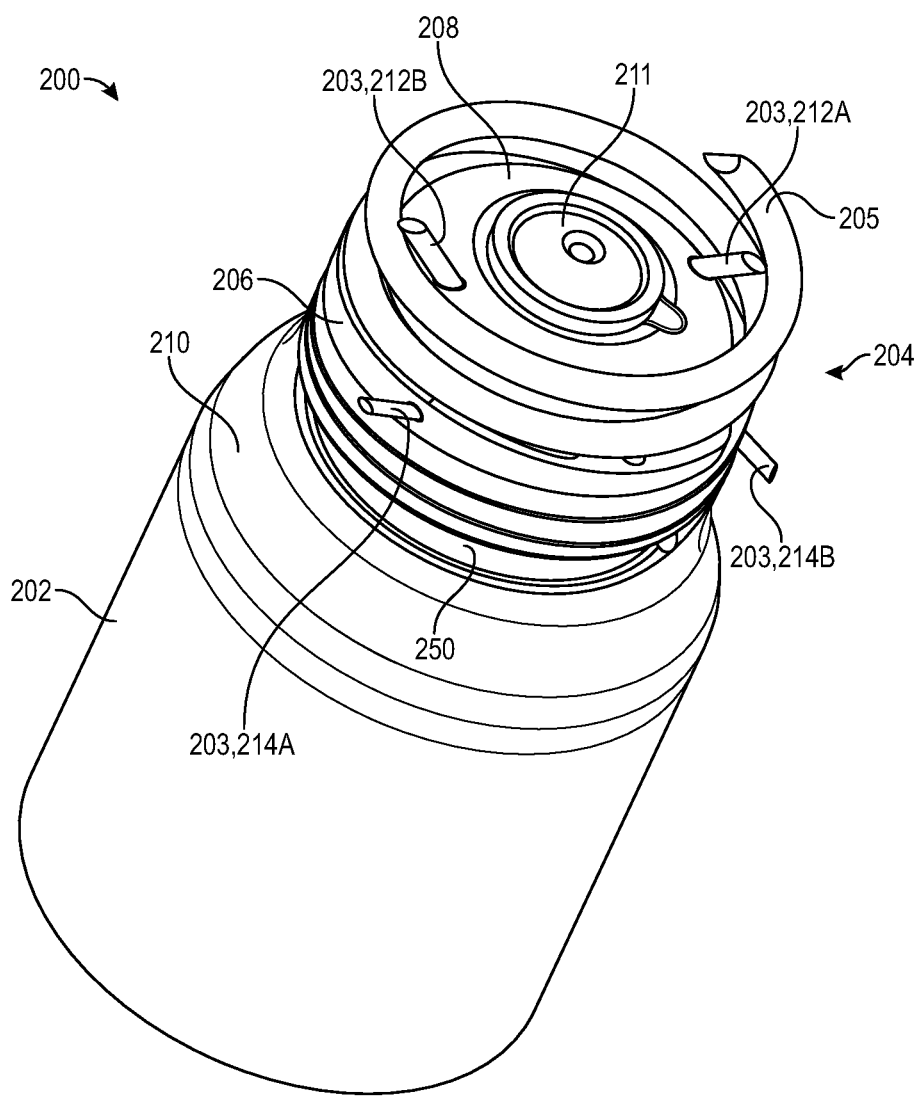
FIG. 2 is an isometric view of a biostimulator in accordance with the present disclosure.

FIG. 2 is an isometric view of a biostimulator 200 in accordance with the present disclosure. The biostimulator 200 includes a housing 202 and a header assembly 204 coupled thereto. Coupling of the housing 202 to the header assembly 204 may be accomplished in various ways including, without limitation, one or more of a biocompatible adhesive, a threaded connection, or ultrasonic welding.

The header assembly 204 generally includes a primary fixation element 205 and one or more backstop elements 203. There may be several backstop elements 203, including forward facing and side facing or laterally extending backstop elements 203, which provide anti-unscrewing features. More specifically, the primary fixation element 205 is a primary helix pointing in a first direction and the backstop elements 203 can include forward facing anti-unscrewing features 212A, 212B. The forward facing anti-unscrewing features can include several forward facing sutures extending from a forward face of the biostimulator 200 in a second direction opposite the first direction.

The primary helix 205 may be substantially formed of any suitable biocompatible material including, without limitation, one or more of stainless steel, nickel-titanium alloys (such as Nitinol), nickel-chromium alloys (such as Incoloy®), titanium, and multiphase nickel alloys (such as MP35N® or 35N LT®). In certain implementations, the substrate material of the primary helix 205 may also be conductive such that the primary helix 205 may be used as an electrode for sensing and/or pacing of cardiac tissue.

The primary helix 205 is preferably sized to couple the biostimulator 200 to cardiac tissue while minimizing damage to the cardiac tissue. The primary helix 205 can extend over any number of turns about a helical axis to a leading point. In certain implementations, for example, the primary helix 205 extends from and including 0.25 turns to and including 3 turns from the helix mount 206. The primary helix 205 can have a wire diameter from and including 0.003 inches to and including 0.03 inches. The primary helix 205 can have a pitch diameter from and including 0.06 inches to and including 0.3 inches. The primary helix 205 can have a pitch from and including 0.01 inches to and including 0.05 inches. Other implementations of the present disclosure may include multiple fixation helices in addition to primary helix 205, wherein each helix extends in the same direction and each helix is adapted to engage cardiac tissue in response to rotation of the biostimulator 200. Such multi-helix implementations may include biostimulators with multifilar helices in which multiple wires are conjointly wound or biostimulators including multiple offset helices.

Functionality of the sutures 212A, 212B depends, at least in part, on their flexibility. Suture flexibility may be controlled by, among other things, material selection, and suture dimensions while the overall counter rotational resistance provided by the forward facing sutures may be further modified by, among other things, the quantity of sutures employed and the relative positioning of the sutures. Regarding materials, the sutures 212A, 212B may be formed of various flexible biocompatible materials including, without limitation, one or more of polypropylene, polyethylene, polyester, nylon, polyurethane, silicone, poly(lactic acid) (PLA), poly(glycolic acid) (PGA), polyimide, polyether ether ketone (PEEK), and polycarbonate. Other biocompatible materials that may be used to form the non-metallic filaments 212A, 212B include natural materials. For example, the sutures 212A, 212B can include natural fibers such as one or more of hair, horse hair, nail, hide, horn, or plant fibers, such as horsetail or thistle. The natural materials can also include sharkskin, which is microporous and has a rough surface similar to sandpaper. The rough surface can promote fixation of the secondary fixation element to heart tissue, however, sharkskin may have material characteristics that discourage ingrowth of cardiac tissue into the secondary fixation element. It is contemplated that such anti-ingrowth characteristics can be beneficial in certain circumstances.

Dimensionally, the length and diameter of the sutures 212A, 212B may vary depending on the specific configuration of the biostimulator 200, however, in certain implementations the sutures 212A, 212B have a length from and including 0.003 inches to and including 0.2 inches and a diameter from and including 0.003 inches to and including 0.03 inches. In certain implementations, the flexibility of the sutures 212A, 212B is sufficiently high to resist counter rotation caused by general cardiac activity and movement of the patient but low enough such that removal and/or repositioning of the biostimulator 200 is possible without significant damage to the cardiac tissue. For example, each of the sutures 212A, 212B may have a stiffness (Young's Modulus) from and including 0.5 gigapascals (GPa) to and including 10 GPa. In certain implementations, the sutures 212A, 212B may include tips that are configured to improve engagement with cardiac tissue. For example, the suture 212A, 212B may be trimmed or otherwise formed to have sharpened tips.

The header assembly 204 may include multiple components including a helix mount 206, a cap 208, and a flange 210. Generally, the helix mount 206 couples to and retains the primary helix 205 while the cap 208 retains each of the several forward facing sutures. The flange 210 couples the header assembly 204 to the housing 202 and provides a central structure to which each of the helix mount 206 and the cap 208 are mounted. The flange 210 may further include an electrode 211 that contacts tissue when the biostimulator is implanted and through which electrical stimulation may be delivered. The example biostimulator 200 further includes several laterally extending backstop elements 203. For example, backstop elements 203 can include laterally extending non-metallic filaments 214A-214C. The laterally extending backstop elements can be lateral sutures 214A-214C (lateral suture 214C being hidden in FIG. 2). As illustrated in FIG. 2, such lateral sutures may be coupled to and extend from the helix mount 206.

Portions of the header assembly 204 may be coated or filled with a biocompatible epoxy or similar material. For example, in certain implementations, a gap 250 may be present between the flange 210 and the helix mount 206 and may be filled with a biocompatible adhesive or epoxy such as one of NuSil™ medical adhesive 6219 and Hysol® M31-CL. Such adhesives and epoxies may be used to reinforce coupling between components of the header assembly 204 and protect the components from wear and corrosion.

One or more surface modification technologies may also be applied to contact surfaces of the biostimulator 200. In general, such contact surfaces may correspond to any component of the biostimulator 200 that contacts or otherwise interacts with tissue of the heart when the biostimulator 200 is implanted. Examples of contact surfaces of the biostimulator 200 include, without limitation, the face of the cap 208 and the exterior surface of the primary helix 205. For example, a surface modification treatment may be applied to the cap 208, in whole or in part (e.g., only a specific portion of the face 208), to modify the properties of the cap 208 as compared to the substrate from which the cap 208 is substantially formed.

Such technologies may include technologies to, among other things, change one or more of the surface energy, the surface charge, the surface chemistry, or the surface morphology of the contact surface. Such modifications may be applied to promote a more organized, thinner fibrous capsule forming about the contact surface when the biostimulator 200 is implanted, thereby reducing the effects of such a capsule on pacing thresholds. For example, implantation of the biostimulator 200 into the heart may cause the body's natural foreign body response (FBR) to form thick scar tissue around or near a distal end of the biostimulator 200 or around specific components of the biostimulator 200, such as the cap 208 and the primary helix 205. This scar tissue may ultimately impede pacing by the biostimulator 200. By altering the properties of the contact surface between the biostimulator 200 (or a specific component thereof) and the heart through the application of surface modification technologies, the FBR may be controlled or directed to promote a more predictable tissue reaction. For example, surface modification technologies may be applied to promote the formation of a relatively thin and even tissue capsule around the biostimulator 200. Surface modification may also be used to promote improved substrate-to-tissue adhesion, thereby improving fixation of the biostimulator 200 within the heart tissue.

Various surface modification technologies may be applied to the contact surface using different techniques. For example, surface energy of the contact surface may be modified by, among other things, glow discharge or plasma treatment of the contact surface. As another example, surface charge may be modified by material selection or deposition of polymers or other materials that may be electrically charged or conductive onto the contact surface. Examples of such materials include, without limitation, piezoelectric polymer films and polyvinylidene fluoride (PVDF) films. Surface chemistry may be modified by, among other techniques, one or more of radiation grafting, protein patterning with soft lithography or micro-contact printing, and immobilization of peptides or proteins in specific micro patterns on the material surface. As yet another example, surface morphology may be modified by topographical patterning of the contact surface. Such patterning techniques may include, without limitation, one or more of laser micromachining and micromolding, such as micromolding using polydimethylsiloxane (PDMS).

Figure 3:
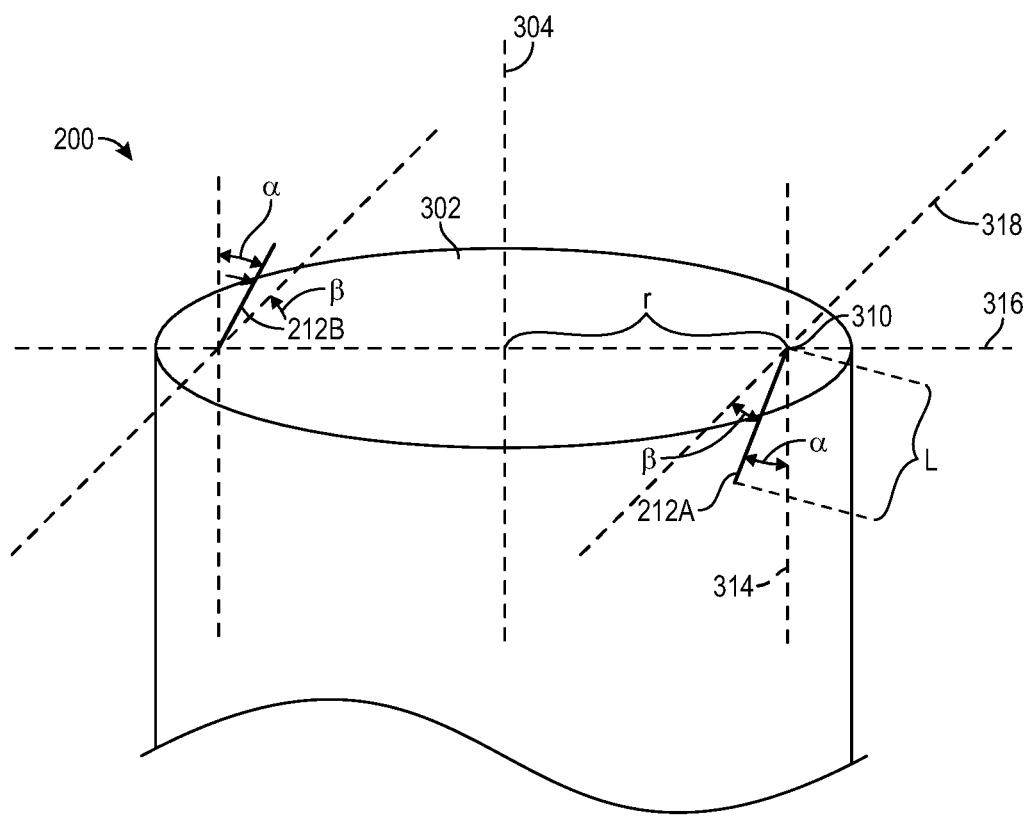
FIG. 3 is a pictorial illustration of a distal face of a biostimulator in accordance with the present disclosure.

FIG. 3 is a schematic illustration of a distal face 302 of the biostimulator 200. For clarity, the biostimulator 200 is illustrated in FIG. 3 as a simple cylinder including the distal face 302 and various features and components of the biostimulator 200 have been omitted.

The biostimulator 200 defines a longitudinal axis 304 extending through the distal face 302. Distributed about the longitudinal axis are forward facing sutures 212A, 212B. The remainder of the foregoing discussion will describe aspects of the suture 212A in detail; however, the foregoing discussion is similarly applicable to the suture 212B. Moreover, while the biostimulator 200 includes two forward facing sutures 212A, 212B, the biostimulator 200 is intended only as an example of one implementation of the present disclosure. In other implementations, one or greater than two sutures may extend from the forward face 302 of the biostimulator 200. In implementations in which more than one sutures extends from the forward face, the multiple sutures may be distributed evenly or unevenly about the forward face 302.

The suture 212A extends from a suture origin 310 at a radius r from the longitudinal axis 304. In certain implementations, r is a distance from and including 0.03 inches to and including 0.3 inches. For purposes of establishing a frame of reference, a first axis 314 extends through the suture origin 310 parallel to the longitudinal axis 304. A second axis 316 extends through the origin perpendicular to the first axis 314 and extends towards the longitudinal axis 304. Finally, a third axis 318 extends perpendicular to each of the first axis 314 and the second axis 316. The specific location and the orientation of the first axis 314, the second axis 316, and the third axis 318 are intentionally defined relative to the suture 212A. Accordingly, to the extent a biostimulator in accordance with this disclosure includes additional sutures, each suture of the biostimulator will similarly define a respective frame of reference.

Forward facing sutures of biostimulators in accordance with this disclosure are generally directed in a direction opposite that of a primary helix (not shown) of the biostimulator 200. In certain implementations, the sutures may extend from the forward face 302 at a predetermined orientation and have a predetermined length. For example, the suture 212A may extend for a length L from its origin 310 at both of a first angle $\alpha$ relative to the first axis 314 and a second angle $\beta$ relative to the third axis 316. In certain implementations, L is from and including 0.01 inches to and including 0.3 inches, $\alpha$ is from and including 10 degrees to and including 50 degrees, and $\beta$ is from and including 15 degrees to and including 75 degrees.

FIGS. 4A-4D illustrate interaction of the biostimulator 200 and, more specifically the suture 212A, with a portion of cardiac tissue 402.

Figure 4A:
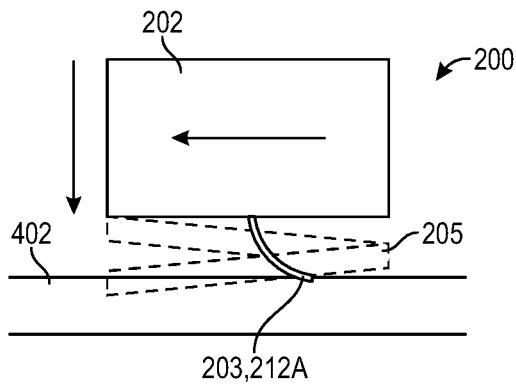
FIGS. 4A-4E are schematic illustrations of interactions between a biostimulator and a target tissue in accordance with the present disclosure.

FIG. 4A illustrates fixation of the biostimulator 200 to the portion of cardiac tissue 402. As shown in FIG. 4A, the primary helix 205 is affixed to the cardiac tissue 402 by rotating the biostimulator in a clockwise direction. As the primary helix 205 engages the cardiac tissue 402 and the biostimulator 205 advances, the backstop element 203 contacts the tissue. For example, backstop element 203 can be the suture 212A, which bends and travels along the cardiac tissue 402 without engaging the cardiac tissue 402.

Figure 4B:
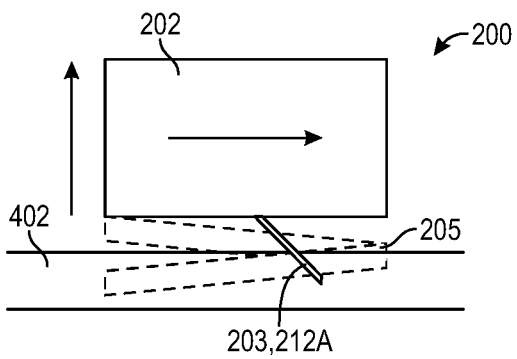

FIG. 4B illustrates anti-rotation behavior of the suture 212A. After fixation of the primary helix 205, counter rotation of the biostimulator 200 (i.e., rotation in a counter clockwise direction) causes the suture 212A to engage the cardiac tissue 402 and, by doing so, the suture 212A resists further counter rotation and dislodgment of the primary helix 205 from the cardiac tissue 402.

Figure 4C:
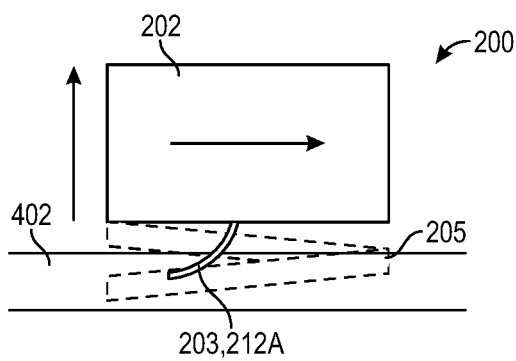

The counter rotational resistance provided by the suture 212A is generally intended to maintain fixation of the biostimulator 200 to the cardiac tissue 402 during regular cardiac activity. However, in certain instances, removal and replacement and/or relocation of the biostimulator 200 may be required. In such instances, the counter rotational resistance provided by the suture 212A may be overcome by applying additional counter rotational force to the biostimulator 200. As illustrated in FIG. 4C, such counter rotational force may cause the suture 212A to bend such that the suture 212A is temporarily oriented in the same direction as the primary helix 205.

Figure 4D:
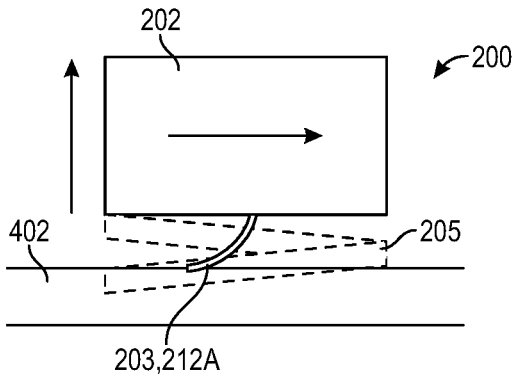
Figure 4E:
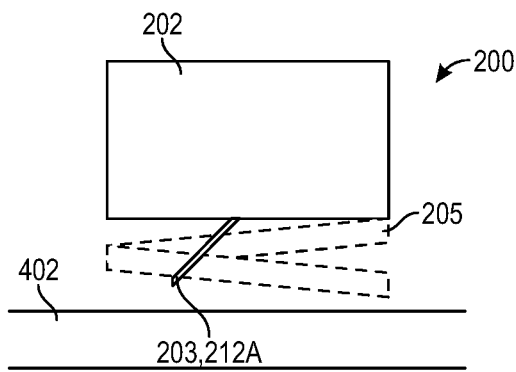

As further illustrated in FIG. 4D further counter rotation of the suture 212A after the bending illustrated in FIG. 4C causes the suture 212A to disengage from the cardiac tissue 402, allowing the primary helix 205 to be unscrewed from the cardiac tissue 402. During unscrewing, the sutures 212A generally will remain bent until the biostimulator 200 is sufficiently detached from the cardiac tissue 402 to allow the suture 212A to return to its starting position, as illustrated in FIG. 4E.

Figure 5:
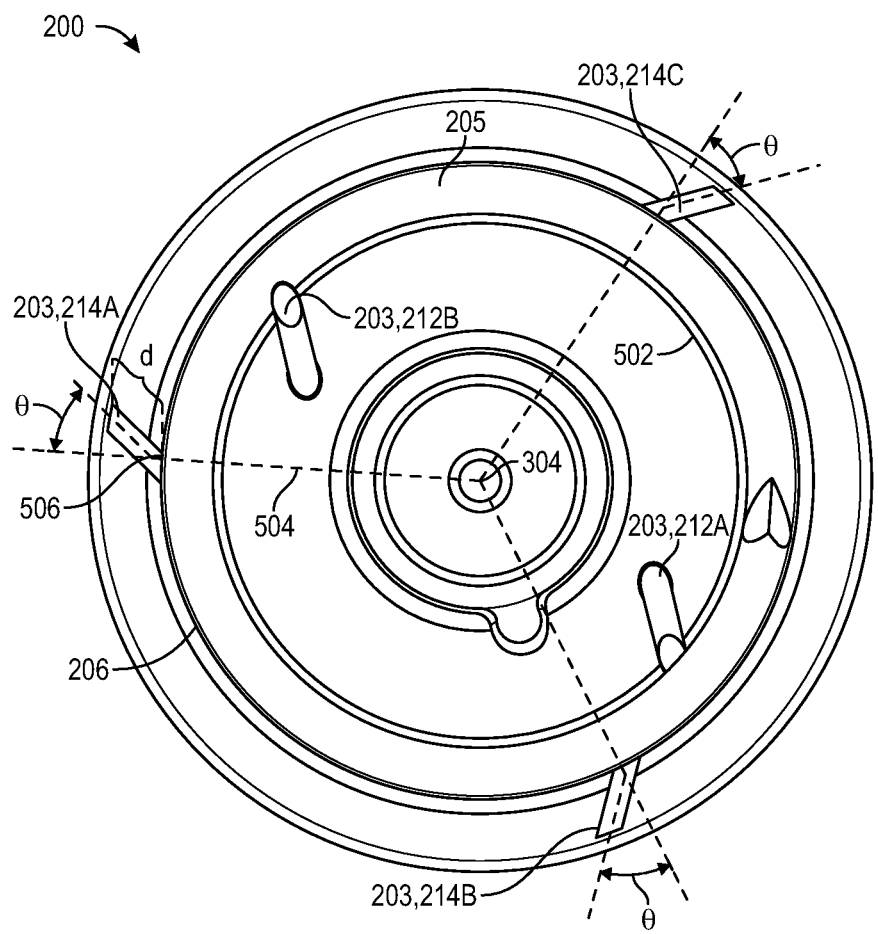
FIG. 5 is a distal view of a biostimulator in accordance with the present disclosure.

FIG. 5 is a top view of the biostimulator 200 of FIG. 2. As shown in FIG. 5, the forward facing backstop elements 203, e.g., sutures 212A, 212B, may extend, at least in part, beyond an inner diameter 502 of the primary helix 205. Such extension may result in sutures extending between adjacent coils of the primary helix 205. For example, the suture 212A is shown extending between distal coils of the primary helix 205. Overlap of the sutures 212A, 212B may be used to further modify the anti-rotational resistance provided by the sutures 212A, 212B. More specifically, as the biostimulator 200 experiences anti-rotational force and the sutures 212A, 212B begin to bend, one or more of the sutures 212A, 212B may contact the primary helix 205. Such contact may prevent additional bending of the sutures 212A, 212B unless additional counter rotational force is applied.

The lateral backstop features 203, e.g., sutures 214A-214C, are also illustrated in FIG. 5. In certain implementations, the lateral sutures 214A-214C are side-facing sutures distributed about the helix mount 206 and are adapted to resist counter rotational force by engaging tissue adjacent the biostimulator 200. Similar to the forward facing sutures 212A, 212B, the lateral sutures 214A-214C may be composed of a flexible biocompatible material and may be designed to have a stiffness that resists unscrewing caused by cardiac and patient activity while facilitating removal of the biostimulator 200 without significant tissue damage. For example, each of the lateral sutures 214A-214C may be composed of a flexible biocompatible and/or polymeric material such as polypropylene, polyethylene, polyester, nylon, polyurethane, silicone, PLA, PGA, polyimide, PEEK, and polycarbonate. Other biocompatible materials that may be used to form the sutures 214A-214C include natural materials, e.g., natural fibers including one or more of hair, horse hair, nail, hide, horn, or plant fibers, such as horsetail or thistle. The natural materials may include sharkskin. The lateral sutures 214A-214C may have a stiffness value (Young's Modulus) from and including 0.5 GPa to and including 10 GPa. In certain implementations, the biostimulator 200 may include from and including one to and including eight lateral sutures, which may be distributed evenly or unevenly about the helix mount 206. With specific reference to lateral suture 214A, each of the lateral sutures may be configured to extend from the helix mount 206 a predetermined distance d at a predetermined angle θ relative to a normal 504 extending between the longitudinal axis 304 of the biostimulator 200 and an origin 506 of the lateral suture 214A. In certain implementations d may be from and including 0.003 inches to and including 0.05 inches and θ may be from and including 15 degrees to and including 75 degrees. Each of the lateral sutures 214A-214 C may also have a diameter from and including 0.003 inches to and including 0.03 inches.

Figure 6A:
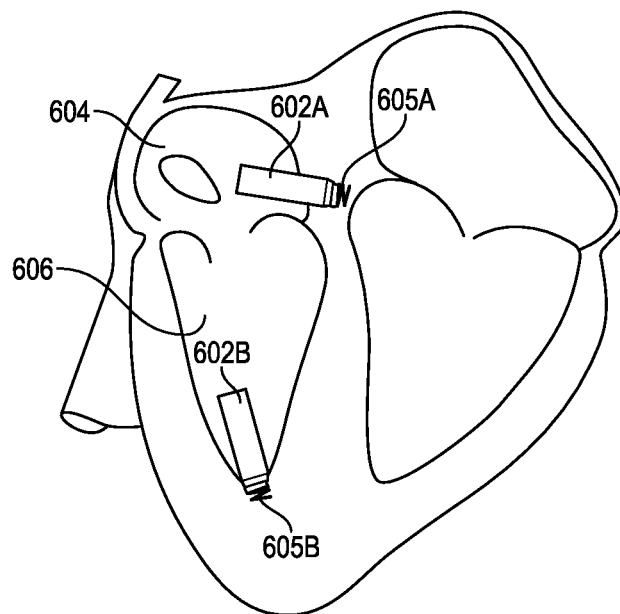
FIGS. 6A-6B are schematic illustrations of delivery of biostimulators into a patient heart in which the biostimulators are to be implanted in accordance with the present disclosure.
Figure 6B:
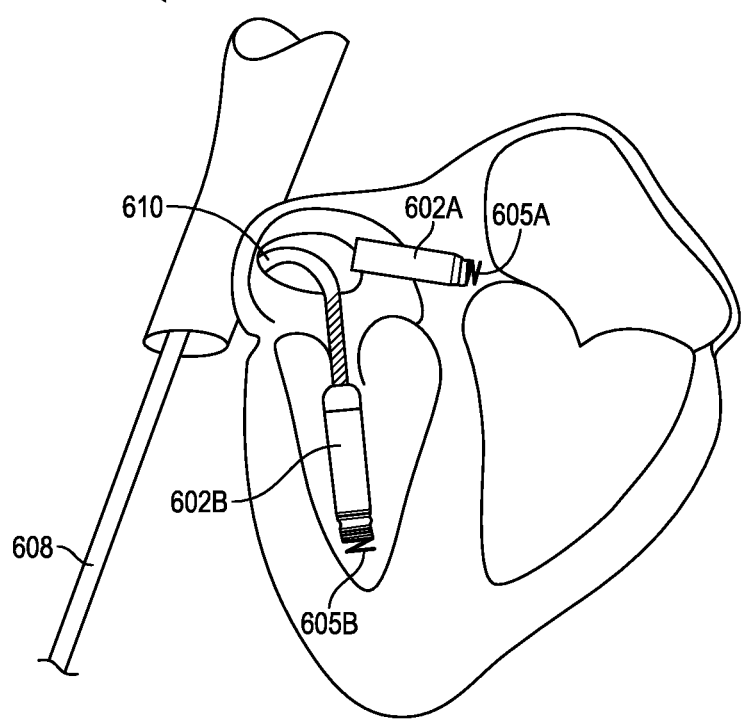

FIGS. 6A-6B illustrate endocardial implantation of biostimulators 602A, 602B in chambers of a patient heart 600. As shown in FIG. 6A, a first biostimulator 602A is implanted within an atrium 604 of the heart 600 while a second biostimulator 602B is implanted within a ventricle of the heart 606. Implantation of each of the first and second biostimulators 602A, 602B may be achieved, in part, by insertion of the biostimulators 602A, 602B endocardially through a guiding catheter. A torqueable catheter can be used to rotate the respective housings of the biostimulators 602A, 602B and force the respective primary helices 605A, 605B of the biostimulators 602A, 602B into corresponding heart tissue, affixing the primary helices 605A, 605B and corresponding electrodes into contact with stimulable tissue. Similarly, and as illustrated in FIG. 6B, removal and retrieval of the biostimulators 602A, 602B may also be accomplished endocardially through a guiding catheter 608. In the example of FIG. 6B, the second biostimulator 602B is in the process of being removed from the heart 600. To remove the second biostimulator 602B, a torqueable catheter 610 may be inserted into the heart 600 through the guiding catheter 608 and coupled to the biostimulator 602B. The torqueable catheter 610 may then be counter rotated to disengage the biostimulator 602B as described above. A similar process of inserting guide and torque catheters may also be used for epicardial fixation and removal of biostimulators in accordance with this disclosure.

Figure 7:
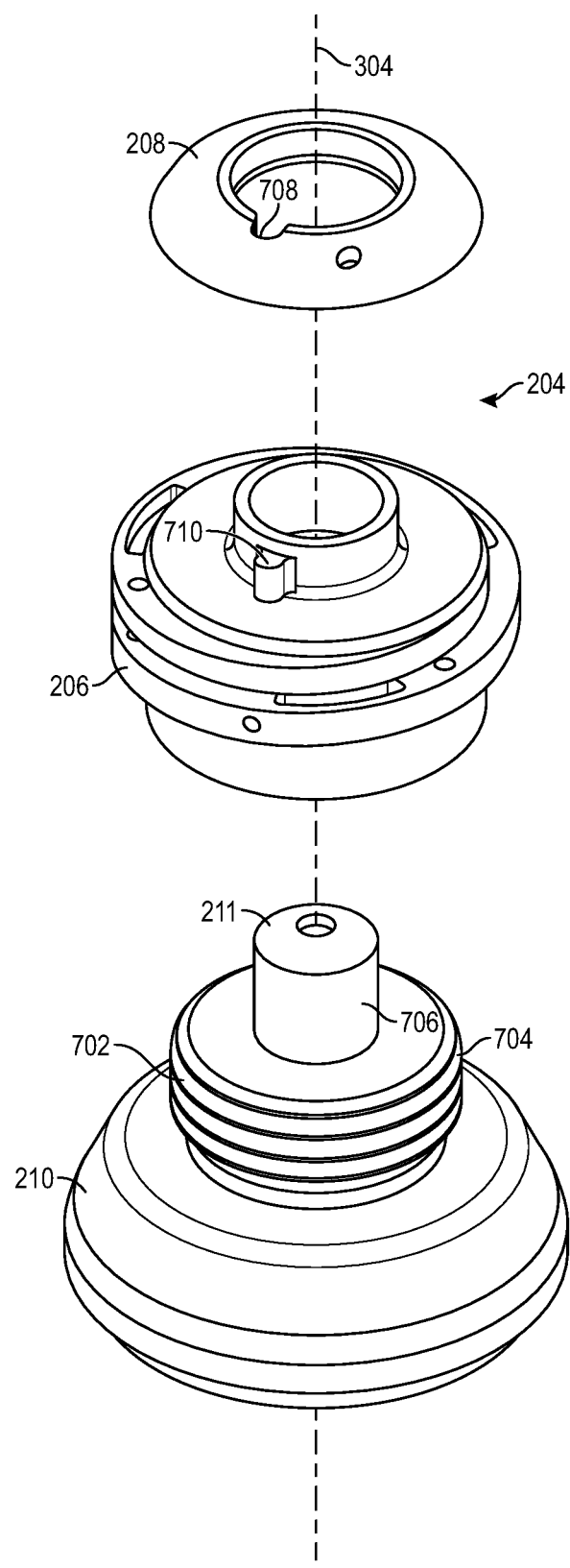
FIG. 7 is an exploded view of a header assembly of a biostimulator in accordance with the present disclosure.

FIG. 7 is an exploded view of the header assembly 204 of FIG. 2 with the primary helix 205, forward facing sutures 212, and lateral sutures 214 removed for clarity. As illustrated in FIG. 7, the flange 210 may include a central post 702 that extends through each of the helix mount 206 and the cap 208 and to which each of the helix mount 206 and the cap 208 may be coupled. In certain implementations, the central post 702 may include a threaded section 704 adapted to mate with corresponding threads of the helix mount 206 to form a threaded connection. In other implementations, coupling between the helix mount 206 and the flange 210, may be achieved by other methods including, without limitation, adhesives and ultrasonic welding. Accordingly, helix mount 206 can be mounted on housing 102 by attaching helix mount 206 to central post 702 and/or flange 210 that is likewise mounted on housing 102. The central post 702 may further includes a smooth section 706 capped with the electrode 211 that is inserted through the helix mount 206.

The cap 208 may be coupled to the helix mount 206 such that the position and orientation of the forward-facing sutures 212A, 212B (shown in FIG. 2) are maintained relative to the helix mount 206 and the primary helix 205 (shown in FIG. 2). As shown in FIG. 7, for example, the cap 208 defines a keyway 708 into which a corresponding key 710 of the helix mount 206 may be inserted to establish a specific orientation of the cap 208 relative to the helix mount 206. Other implementations may include alternative mating features of the cap 208 and the helix mount 206 that similarly insure that the cap 208 is mounted with a particular orientation relative to the helix mount 206. For example, in certain implementations, the helix mount 206 and the cap 208 may include matching threads, such as single-start threads, adapted to dispose the cap 208 in a predetermined orientation when tightened onto the helix mount 206. The predetermined orientation can include a relative location between a tip of the fixation element 105 and a tip of the one or more backstop elements 203. For example, the tips of forward-facing sutures 212A, 212B can be clear of the leading edge of the primary fixation element 105 so as to not interfere with the leading edge when it penetrates tissue. More particularly, the tip of the backstop elements 203 can trail the tip of the fixation element 205 by an amount that ensures that, when the distal end of biostimulator 100 is being rotated against tissue, the backstop element 203 does not bend into the pathway of the fixation element 105 advancement. An example of this is shown in FIG. 2, in which the tip of the forward-facing suture 212A trails the leading edge of fixation element 205 by at least 15 degrees about the longitudinal axis. For example, the tip of the forward-facing suture 212A can trail the leading edge of the fixation element 205 by 30 degrees in the counterclockwise direction.

Figure 8A:
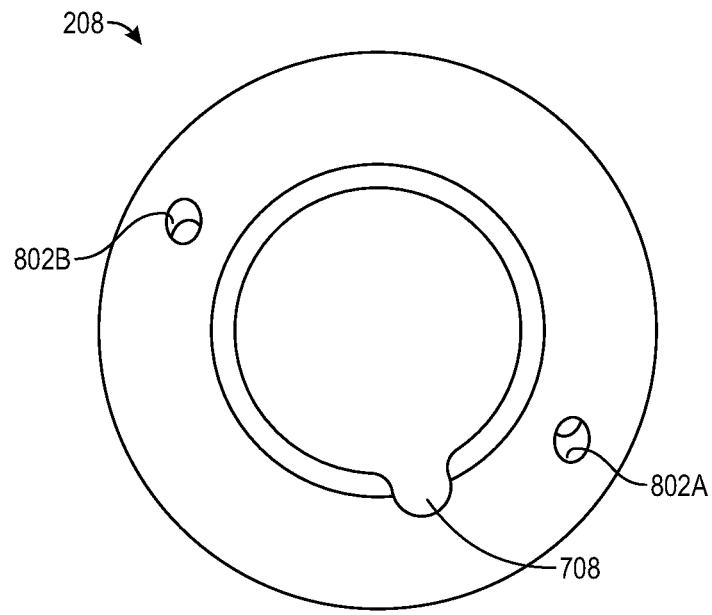
FIGS. 8A-8B are top and bottom views, respectively, of a cap of a header assembly of a biostimulator in accordance with the present disclosure.
Figure 8B:
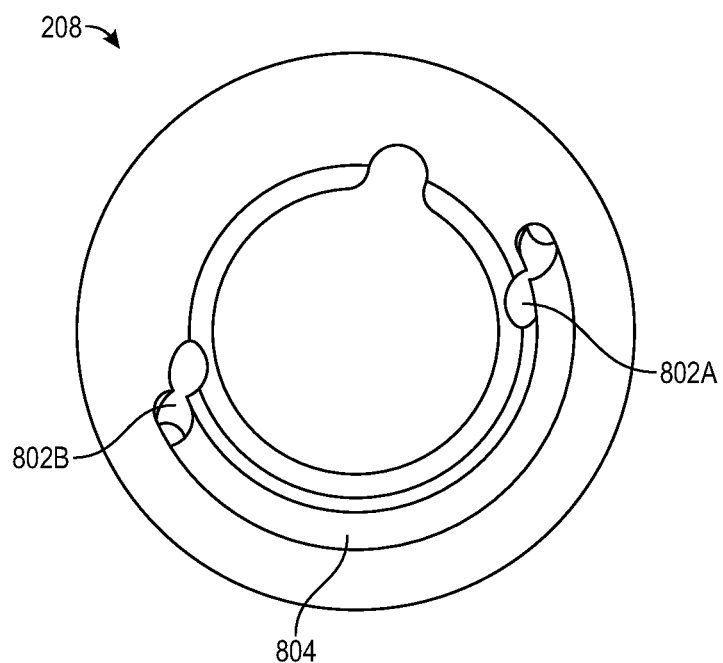

FIGS. 8A-8B are top and bottom views of the cap 208. The cap 208 is generally adapted to receive and retain forward facing sutures, such as the sutures 212A, 212B shown in FIG. 2. To do so, the cap 208 may define several suture bores 802A, 802B within which the sutures 212A, 212B may be retained and through which the sutures 212A, 212B may extend. More particularly, the non-metallic filaments 203 of biostimulator 100 can be inserted through bores 802A, 802B, or any other bores in cap 208. Each suture bore 802A, 802B may be angled to maintain a suture extending therethrough at a particular angle. For example, the suture bores 802A, 802B may be oriented at the angles α and β previously discussed in the context of FIG. 3 such that sutures extending through the sutures bores 802A, 802B are maintained at the angles α and β.

In certain implementations, each suture is formed separately and individually installed in the cap 208. Installation may include, among other things, applying an adhesive or otherwise fixing the sutures to an underside of the cap 208 or within a cavity defined by the cap 208. In other implementations pairs of sutures, such as the sutures 212A and 212B of FIG. 2, may also be formed from a single length of suture material that is trimmed to length. For example, the cap 208 may include a suture groove 804 extending between suture bores 802A, 802B. During manufacturing, a length of suture material may be inserted into a first of the suture bores 802A, 802B, run through the suture groove 804 and out a second of the suture bores 802A, 802B. The portion of the thread extending from each of the suture bores 802A, 802B may then be trimmed to length as required. In implementations including additional pairs of sutures and suture bores, each pair of sutures may similarly be formed from a single length of suture material. A single length of suture material may also be threaded through multiple pairs of suture bores and run along corresponding suture grooves such that more than two sutures are formed from the same length of suture material.

Figure 9A:
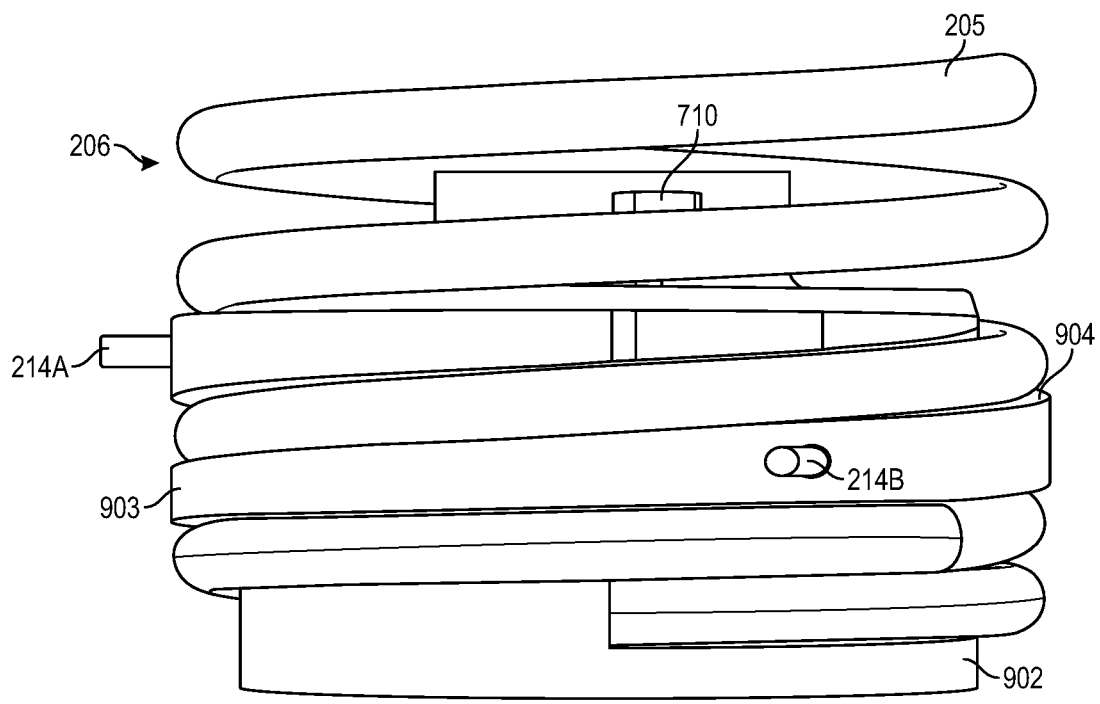
FIGS. 9A-9B are side elevation and cross-sectional side views, respectively, of a fixation element of a header assembly in accordance with the present disclosure.
Figure 9B:
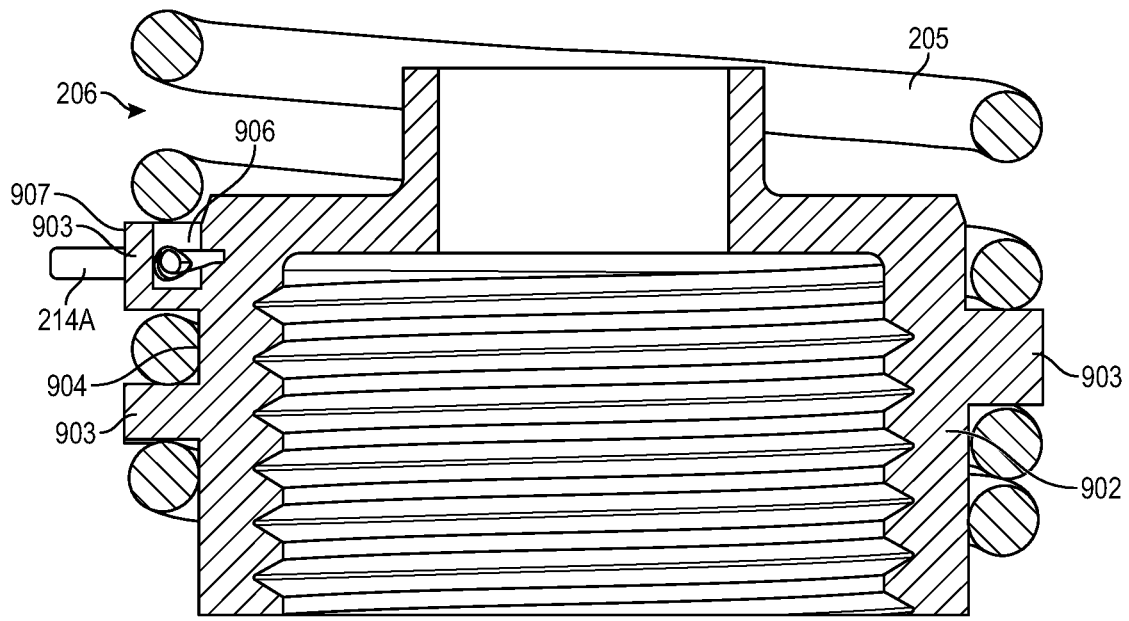

FIGS. 9A and 9B are a side elevation view and a cross sectional side view of the helix mount 206. Helix mount 206 can be mounted on housing 102. The helix mount 206 includes a helix mount body 902 defining a helical groove 904 shaped to receive the primary helix 205. More particularly, helix mount 206 may have a helix mount flange 903 that extends around the helix mount body 902 in a helical fashion to form a threaded flange form onto which fixation element 205 can be mounted. For example, fixation element 205 can include a coiled wire that can be screwed onto helix mount 206 to secure the fixation element 205 to helix mount 206 and housing 102. Fixation element 205 can be fixed onto helix mount 206 during manufacturing, e.g., by welding, gluing, or otherwise bonding the components together, such that fixation element 205 does not rotate relative to helix mount 206 during operation.

The helix mount 206 may further define several holes or similar cavities 906 into which each of the lateral sutures 214A-214C (lateral suture 214C is shown in FIG. 5) may be inserted and fixed. For example, a first end of backstop elements 214A-214C can be positioned within cavities 906 and the backstop elements can extend through helix mount flange 904 to a second end. For example, backstop elements can be non-metallic filaments that extend through respective bores in a sidewall 907 of helix mount flange 904 from the first end to the second end. Cavities 906 can be filled with an adhesive or other filler to secure the first end of the non-metallic filaments within the cavities and fix the backstop elements to helix mount 206.

Features such as cavities and through-holes that promote tissue in-growth into and through the biostimulator can increase fixation of the device to tissue and prevent anti-unscrewing and disengagement of the biostimulator from tissue. It should be understood that many of the anti-unscrewing features described herein are configured to prevent unintentional detachment of the biostimulator from tissue immediately after implant, but before tissue has had time to grow into the device. In one implementation, the through-holes are angled with an orifice on a distal face of the biostimulator.

The through-holes described herein can be open and free of any obstructing material, or alternatively, can be filled with a fast-dissolving substance, such as mannitol, or with a slowly bioabsorbable material. The advantage of filling the through-holes or cavities prior to implantation of the biostimulator is that it eliminates the risk of trapped air embolism and cavities that can serve as a nidus for bacterial growth.

The anti-unscrewing features described herein are intended to prevent a biostimulator from unintentionally unscrewing or disengaging from tissue. These features are most critical at the time shortly following implantation of the biostimulator (e.g., within 1-3 months of implantation). After 1-3 months post-implantation, endothelialization will have had sufficient time to occur such that the biostimulator is fully encapsulated by tissue. It may be unlikely that a fully encapsulated biostimulator will inadvertently unscrew itself from tissue.

Features to prevent unscrewing may be designed to be most effective in the short time period post-implant (e.g., within the first 1-3 months after implantation). These anti-unscrewing features can therefore be manufactured out of a bio-absorbable material. Once they are no longer needed to prevent unscrewing of the biostimulator, they can bioabsorb and disappear. Thus, the anti-unscrewing features described herein, e.g., forward facing sutures, may be manufactured out of bioabsorbable materials to be absorbed by the body after the initial 1-3 month time period post-implant.

A fixation element, such as the primary helix 205 shown in FIG. 2, can include cut-outs or indentations along the length of the fixation element. The cut-outs can include semi-circular cutouts into the fixation element. These cut-outs allow for tissue ingrowth after the fixation element has been inserted into tissue. Although not shown, the cut-outs can include other shapes, including triangular, square, rectangular, etc. shaped cut-outs.

In some implementations of the present disclosure, the electrode may be separate from the fixation element. In such implementations, an electrode may be mounted on a flexible arm which extends outwardly from the body or housing of the biostimulator. The flexible arm can extend radially outwards from the biostimulator body or housing to provide additional resistance against tissue in the event that the biostimulator begins to unscrew or become dislodged from tissue. The arm may include additional anti-unscrewing features, such as through-holes, barbs, teeth, sutures etc., to further prevent anti-unscrewing. In some implementations, the flexible arm is flexible in only one direction of rotation (e.g., the direction of rotation that would allow for the leadless biostimulator to unscrew from tissue), and is stiff or non-flexible in the other direction of rotation.

Figure 32A:
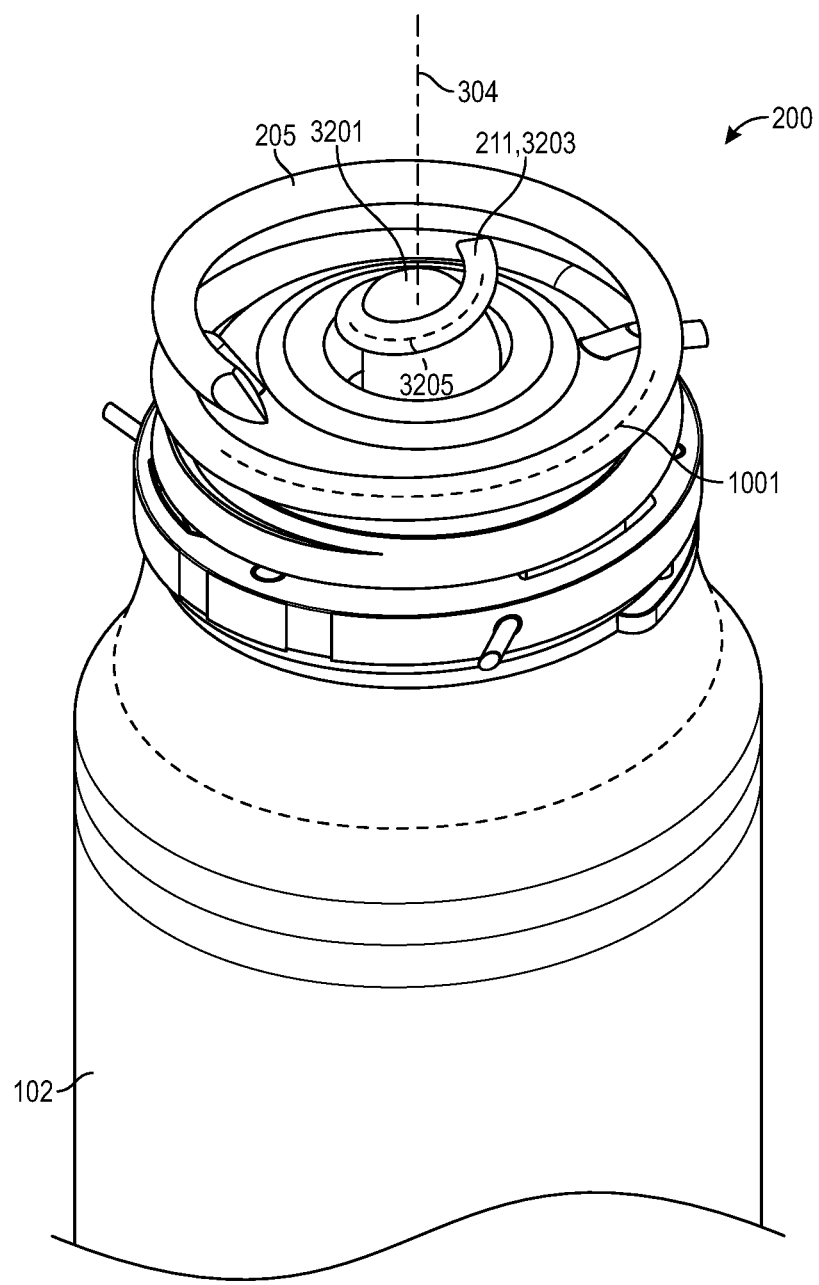
FIGS. 32A and B are perspective views of a biostimulator having an active helical electrode, in accordance with the present disclosure.

Referring to FIG. 32A, in an alternative implementation, a perspective view of a biostimulator 200 is shown, that includes an active helical electrode 211 nestled within the fixation element 205. More particularly, the helices 211 and 205 can both revolve about the longitudinal axis, however, a helix radius of the fixation element 205 may be greater than the helix radius of electrode 211. More particularly, the electrode 211 can be an active helical electrode 211 mounted on the housing 102 of biostimulator 200, and the active helical electrode 211 can perform a dual pacing and fixation function. For example, electrode 211 may include a secondary helix, e.g., an electrode helix 3203, that extends along an electrode helical axis 3205 about the longitudinal axis 304. The electrode helical axis 3205 of the active helical electrode 211 may be radially inward of the helical axis 1001 of fixation element 205. In an aspect, the helical axis 1001 of the fixation element 205 and the electrode helical axis 3205 of the active helical electrode 211 can revolve about the longitudinal axis 304 in a same rotational direction. For example, both helices can revolve in a counterclockwise direction about the longitudinal axis 304.

Active helical electrode 211 may be formed of metallic biocompatible materials including, without limitation, platinum iridium. Active helical electrode 211 may be coated, e.g., with titanium nitride. The coating may also include low-polarization coatings, such as such as platinum, platinum-iridium, iridium, iridium-oxide, titanium-nitride, carbon. Portions of the active helical electrode 211 may be masked to achieve an optimized electrode surface area.

Figure 32B:
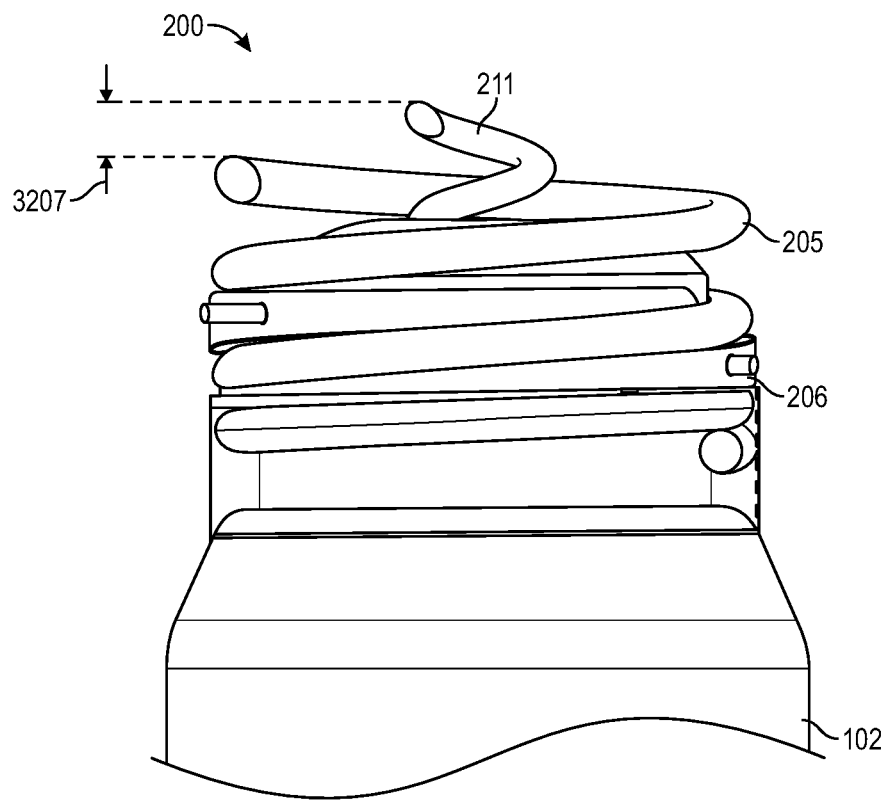

Referring to FIG. 32B, dimensionally, the active helical electrode 211 can extend from and including 0.25 turns to and including 3 turns from the housing. A wire diameter of the active helical electrode 211 can be from and including 0.003 inches to and including 0.03 inches, a pitch diameter from and including 0.02 inches to and including 0.3 inches, and a pitch from and including 0.01 inches to and including 0.1 inches. Active electrode helix 211 may have a different pitch than fixation element 205, allowing for differing grips on tissue passing through 205 during fixation. For example, if active helical electrode 211 pitch was 0.1 mm larger than the pitch of fixation element 205, fixation element 205 would be compressed by 0.1 mm during the course of fixation, causing 205 to compress (or grip) the tissue it has fixated, making dislodgement of the leadless pacemaker 200 less likely, and reducing signal noise.

Referring again to FIG. 32A, the active electrode helix 211 may revolve around an active agent-eluting payload 3201. For example, the payload may be a steroidal plug of material that elutes into the target tissue when helix 211 is secured within the target tissue.

Referring again to FIG. 32B, active helical electrode 211 may extend 0-2.5 turns, e.g., 2.5 turns beyond the helix mount 206. Active helical electrode 211 may be proud of fixation element 205. More particularly, a distal tip of active helical electrode 211 may be distal to a distal tip of fixation element 205. An active helical electrode 211 that is proud of fixation element 205 may allow for sensing of thresholds prior to fixation, reducing the need for repositioning. An example protrusion 3207 is shown. The protrusion 3207 may be 0.020 inch, by way of example, which may allow for one full turn of helical electrode 211. A helical electrode 211 proud of fixation element 205 may also act as a pilot hole for fixation element 205, allowing the fixation of 205 to remain centered while the heart is beating. Furthermore, the helical electrode 211 proud of fixation element 205 may reduce a likelihood of walking of fixation element 205. More particularly, the helical electrode 211 can stabilize fixation element 205 to provide predictable anchoring within the target tissue.

In an embodiment, active helical electrode 211 is the same height or lower than fixation element 205 (not shown). A shorter active helical electrode 211 may reduce electrode surface area which could prolong a battery life of the biostimulator. A height of active helical electrode 211 that is similar or lower than a height of fixation element 205 may help minimize damage to cardiac tissue and the pericardium because the active helical electrode 211 may fixate to a shallower depth.

The helix of the active electrode may have similar structural features as described herein for fixation element 205, for example, both helices are wound in the same direction so that torsional force on the leadless pacemaker into tissue will activate both fixation mechanisms at the same time, thereby adding redundant fixation features and making dislodgement of the leadless pacemaker less likely, and reducing signal noise.

In another embodiment, a leading point of the electrode 211 may be at a six o'clock position to promote shallow penetration of the helix into the target tissue. By contrast to fixation element 205, however, the electrode helix 211 may function to deliver electrical impulses to the target tissue as described above with respect to electrode 211. The biostimulator can be attached to tissue by screwing the fixation element 205 and the electrode 211 into the tissue. When the helices are engaged with the tissue, the electrode 211 is placed in contact with the tissue. Additional anchoring is provided by the increased helical surface area engaged with the tissue by the helical electrode 211. As described herein, anti-unscrewing features can be added to prevent the biostimulator from accidentally dislodging or unscrewing itself from tissue.

Figure 10A:
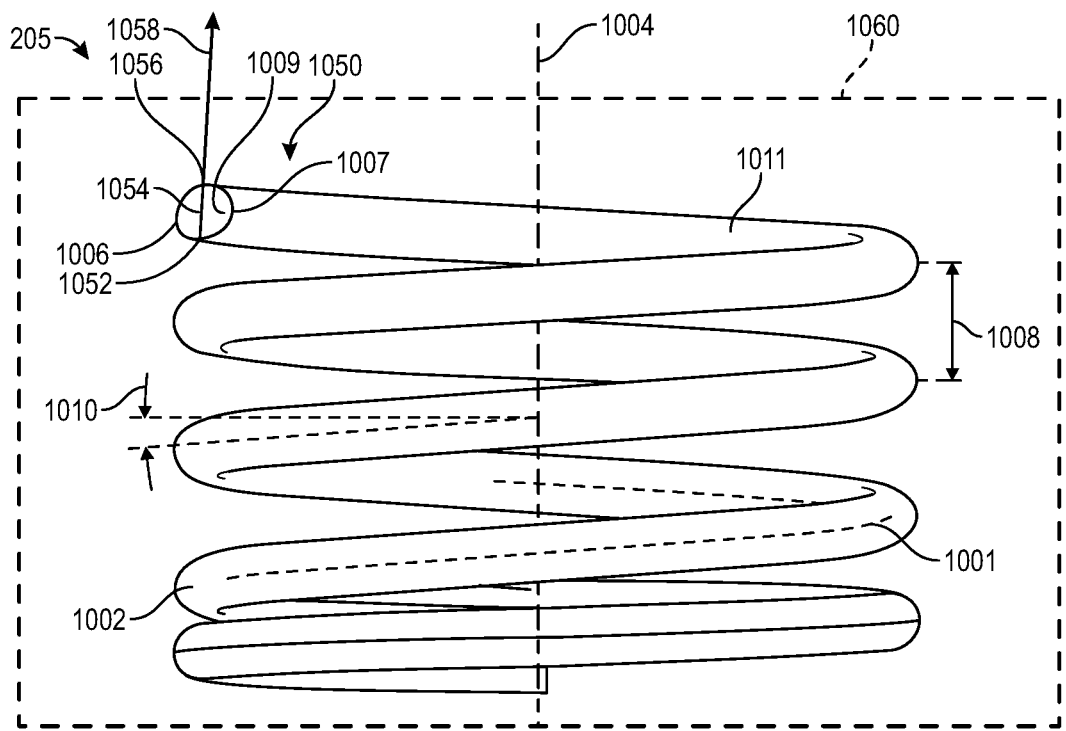
FIGS. 10A-DID are side elevation views of a fixation element in accordance with the present disclosure.
Figure 10B:
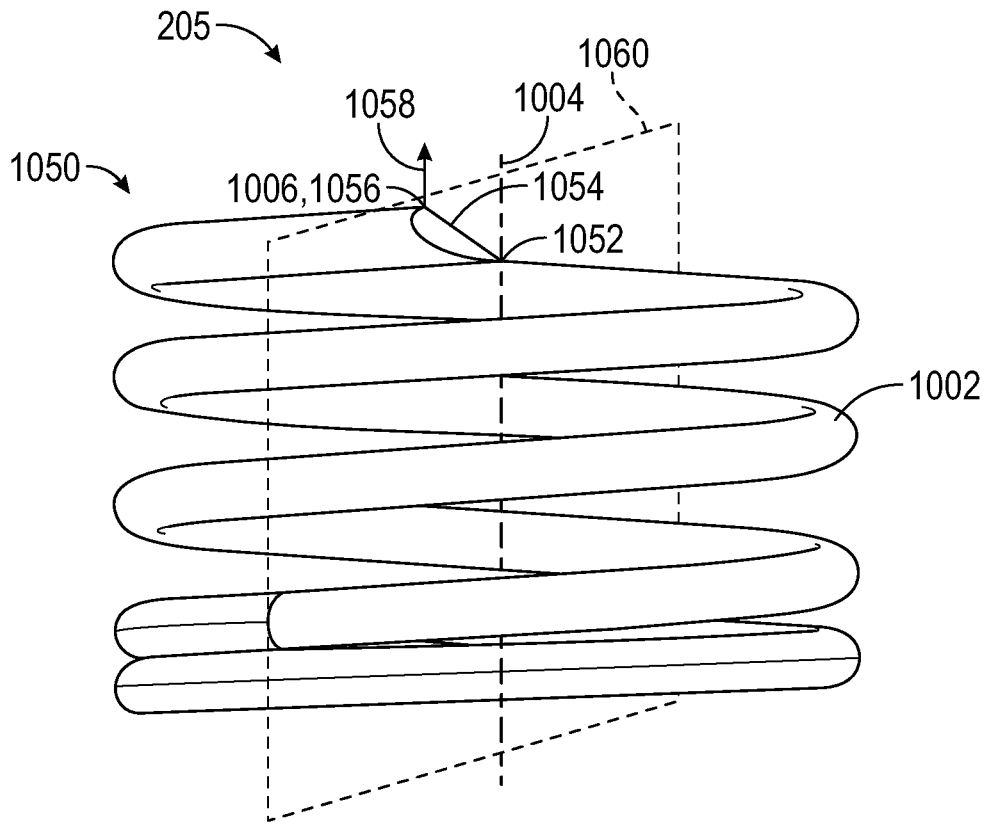
FIG. 10E is a top view of a fixation element in accordance with the present disclosure.
Figure 10C:
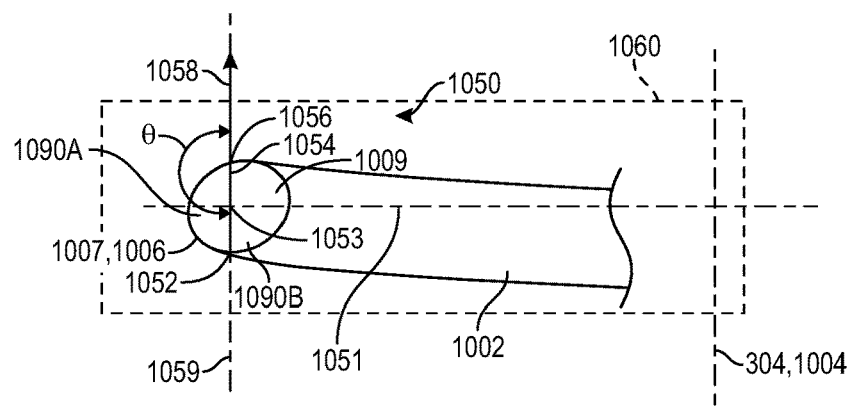
Figure 10D:
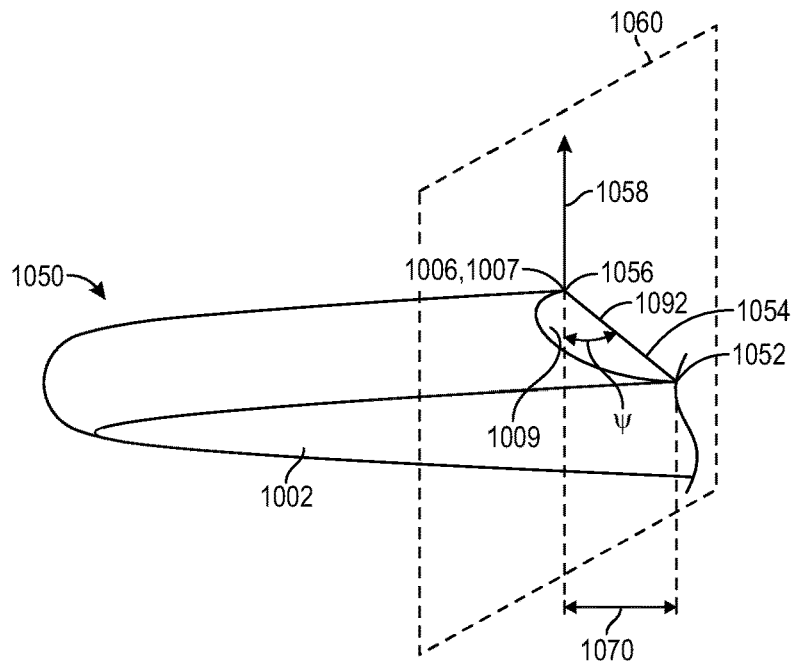
Figure 10E:
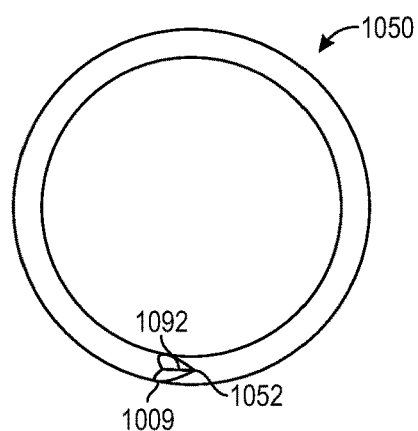

FIGS. 10A-10E illustrate the fixation element 205 of FIG. 2 in further detail. Specifically, FIGS. 10A-10B are side views of the primary helix 205 from different angles, FIGS. 10C-10D are detail views of a distal helix end 1050 of the primary helix 205, and FIG. 10E illustrates a top view of the distal helix end 1050. As shown in FIG. 2, the primary helix 205 is generally disposed on a distal end of a biostimulator, such as the biostimulator 200 of FIG. 2, and is adapted to attach the biostimulator 200 to a wall of the heart by rotating the biostimulator 200 in a screwing direction.

Referring now to FIGS. 10A-10B, fixation element 205 can include a helix extending along a helical axis 1001. For example, the primary helix 205 may be a helical spring formed from a wire coil 1002 and extend about a helix axis 1004, which is generally collinear with a longitudinal axis of the biostimulator 200 (such as longitudinal axis 304, as shown in FIG. 3). In an aspect, the helix is a helical wire, which may be a solid wire or a cut tubing. More particularly, the term wire as used herein refers to an elongated element, e.g., a strand, filament, etc., that has an outer surface extending around helical axis 1001. The outer surface, however, may be formed by cutting, e.g., laser cutting, a spiral cut in a wall of a hypotube to generate a spiral coil. Post-processing, such as electropolishing, sand blasting, etc., can be used to remove burrs and otherwise smooth the cut edges of the tube-formed helical spring. The tube-formed helical spring, like the solid wire coil, can have a leading point that may be further processed by grinding and polishing operations to generate the point morphology described herein. The helical spring can be metallic. Helical axis 1001 of the wire may extend about longitudinal axis 304. The wire coil 1002 can form at least a portion of the fixation element 205, which has a cross-section defining an outer perimeter 1006.

In an embodiment, the wire of fixation element 205 extends along helical axis to a distal edge 1007. Distal edge 1007 can extend around helical axis 1001 to define a helix face 1009 on helical axis 1001. For example, when viewed on end, as in the example of FIGS. 10A-10E, the wire face 1009 can be substantially circular. Such may be the case when the wire is a round wire having an outer surface 1011 that is ellipsoidal. More particularly, when the outer surface 1011 extending along helical axis 1001 from a proximal end to distal edge 1007 has a circular cross-section, the wire face 1009 has a circular area (when the face plane is orthogonal to helical axis 1001). By contrast, when the ellipsoidal outer surface 1011 is non-circular, e.g., when the wire is an elliptical wire, the distal edge 1007 may be elliptical. Accordingly, the circular perimeter of the wire coil 1002 is merely an example of a perimeter shape that may be used in implementations of the present disclosure and primary helices having other shapes and wire coil types may be made that conform to the present disclosure. For example, the wire coil 1002 may be generally formed of a biocompatible material formed into, without limitation, one of a round wire, a flattened or square wire, or hypodermic tubing. The wire coil 1002 can be fabricated from metallic biocompatible materials, such as a nickel-cobalt-chromium-molybdenum alloy, e.g., MP35N® or 35N LT®, medical grade stainless steel, nitinol or similar metal-based derivatives having fatigue resistance. The wire coil 1002 can similarly be formed from machined, cast, or molded plastic.

The distal edge 1007 can be an intersection between the outer surface 1011 and the wire face 1009. Accordingly, the distal edge 1007 can be a transition between a wire surface, e.g., a cylindrical surface, and a leading point 1052 of the fixation element 205. The transitional edge can be angular or rounded. For example, the outer surface of the wire can be gradually rounded toward the leading point 1052 such that the outer surface transitions continuously to leading point 1052 with no identifiable angle of the transitioned surface. In such case, the distal face 1009 may be considered any portion of the wire that is radially offset from a center of the wire by a distance that is less than a distance from the center to the outer surface 1009.

In certain implementations, the primary helix 205 may conform to predetermined parameters regarding the shape of the primary helix 205. For example, as shown in FIG. 10A, the primary helix 205 may be formed to have a predetermined pitch 1008 and a predetermined pitch angle 1010. In certain implementations, the pitch 1008 may be from and including 0.007 inches to and including 0.060 inches and the pitch angle 1010 may be from and including 2.5 degrees to and including 20 degrees.

As shown in each of FIGS. 10A-10E, the distal helix tip 1050 may terminate in the leading point, which may be alternately referred to as a sharpened tip or a tip 1052. The leading point 1052 can be formed by a multi-bevel, e.g., a double-bevel or a triple-bevel, or the outer surface 1009 can be gradually reduced to the leading point 1052 without the use of bevel surfaces.

Figure 11A:
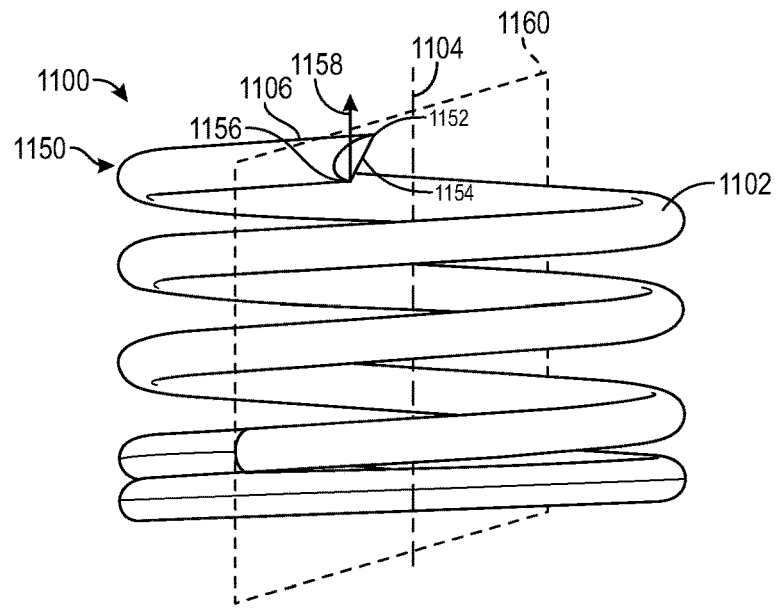
FIG. 11A-11C are side elevation views of a fixation element in accordance with the present disclosure.

Leading point 1052 can be a distalmost point on the wire in the direction of helical axis 1001. Accordingly, the leading point 1052 can be on distal face 1009. It has been discovered that a location of the leading point 1052 on distal face 1009 can affect a penetrating ability of fixation element 205. More particularly, when deployed into tissue, fixation element 205 may dig more shallowly into the tissue when leading point 1052 is more proximal relative to housing 102. By way of example, when deployed into heart tissue, a leading point 1052 positioned at a six o'clock position (most proximal relative to housing 102 and on distal edge 1007 as shown in FIG. 10C) may tend to penetrate less deeply than a leading point 1052 positioned at a twelve o'clock position (most distal relative to housing 102 as shown in FIG. 11A). Accordingly, when deployed into thinner tissue walls, such as atrial walls, the "six o'clock" point configuration may reduce a likelihood of penetrating fully through the tissue wall and pinning external structures, such as the pericardium.

In an aspect, leading point 1052 can be located at a more or less distal location to control a depth of penetration. For example, referring to FIG. 10C, leading point 1052 can be between a transverse plane 1051 and the housing 102 to cause fixation element 105 to penetrate less deeply into target tissue. More particularly, leading point 1052 can be proximal to the transverse plane 1051. By contrast, leading point 1052 can be on an opposite side of transverse plane 1051 from housing 102, e.g., distal to the transverse plane, to cause fixation element 105 to penetrate more deeply into the target tissue.

Transverse plane 1052 can be orthogonal to longitudinal axis 304 (or helix axis 1004) and may extend along a median line of wire face 1009. More particularly, transverse plane 1051 can intersect a center 1053 of wire face 1009. Accordingly, transverse plane can define a longitudinally located separator between a portion of wire face 1009 that is proximalmost (the surface area that is between transverse plane 1051 and housing 102) and a portion of wire face 1009 that is distalmost (the surface area that is on an opposite side of transverse plane 1051 from housing 102). When leading point 1052 is located at a position within the proximalmost portion of wire face 1009, fixation element 205 can penetrate more shallowly, and vice versa. Several different positions are described in more detail below, however, it will be appreciated that leading point 1052 can be located anywhere on wire face 1009 to control penetration depth in accordance with the principles outlined above.

In an embodiment, as shown in FIGS. 10A-10D, tip 1052 may be disposed on the outer perimeter 1006, e.g., distal edge 1007, of the wire coil 1002. For example, the tip 1052 may be disposed in a proximal or "six o'clock" position that reduces penetration depth of the tip 1052 during screwing into cardiac tissue, thereby reducing the likelihood of over-penetration and corresponding trauma. The six o'clock position can be on a longitudinal plane 1059. The longitudinal plane 1059 may intersect transverse plane 1051 at center 1053. More particularly, longitudinal plane 1059 can be orthogonal to transverse plane 1051 and parallel to longitudinal axis 304 such that the intersection of the planes at the center divides wire face 1009 into quadrants when viewed on end. In an embodiment, leading point 1052 is on the longitudinal plane 1059. For example, leading point 1052 can be on longitudinal plane 1059 proximal to transverse plane 1051 (FIG. 10C) or distal to transverse plane 1051

Figure 11B:
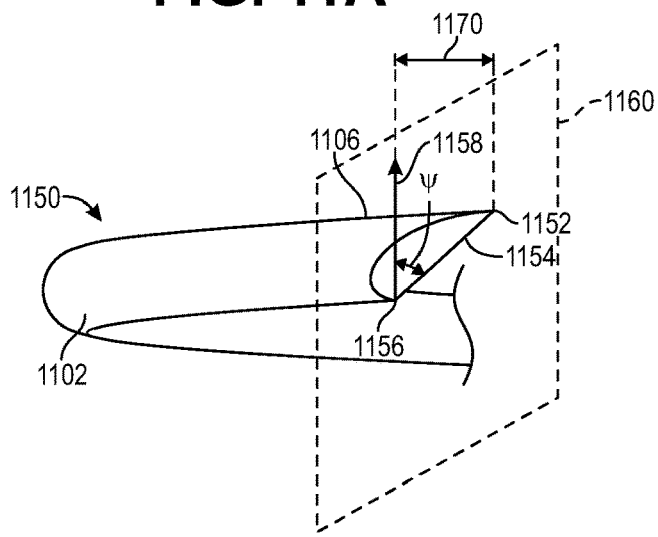
Figure 11C:
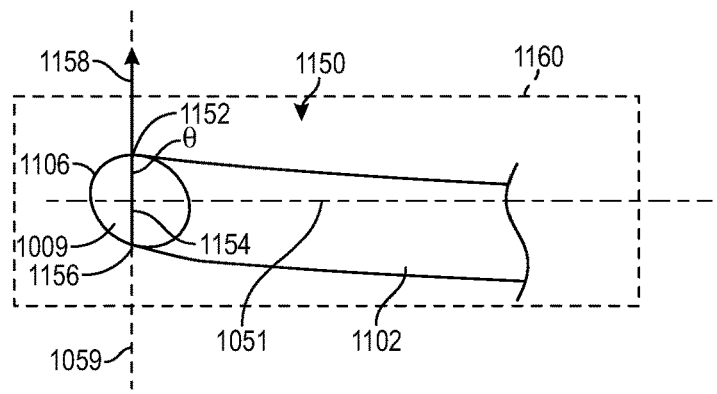

(FIG. 11C). In an embodiment, leading point 1052 is at the six o'clock position, which is on distal edge 1007 at the intersection of distal edge 1007 and longitudinal plane 1059 (FIG. 10C).

In an embodiment, wire face 1009 includes a plurality of bevel faces converging at leading point 1052. For example, referring to FIG. 10C, a first bevel face 1090A and a second bevel face 1090B form separate portions of wire face 1009. Referring to FIG. 10D, the bevel faces can intersect along a leading edge 1092. The leading edge 1092 can be an edge 1054 extending between the tip 1052 and base 1056. More particularly, leading edge 1092 can extend from leading point 1052 to base 1056 on distal edge 1007 along wire face 1009. Base 1056 can be on an opposite side of transverse plane 1051 from housing 102.

The general position and orientation of the tip 1052 may be described in terms of the relative angle of the edge 1054. For example, each of FIGS. 10A-10D include a vector 1058 distally extending from the base 1056 parallel to the helix axis 1004 such that a plane 1060 is defined by the helix axis 1004 and the vector 1058. The orientation of the tip 1052 may then be described in terms of an angle θ (shown in FIG. 10C) corresponding to an angle away from the vector 1058 along the plane 1060. The angle θ may be from and including 0 degrees to and including 180 degrees, the latter of which corresponds to the "six o'clock" position illustrated in FIGS. 10A-10D. A second angle ψ may specify the forward extension of the tip 1052. More specifically, the second angle ψ may correspond to the angle at which the edge extends relative to the plane 1060. In certain implementations, ψ may be from and including 10 degrees to and including 60 degrees. The distal helix tip 1050 may also have a predetermined tip length 1070, which generally corresponds to the longitudinal distance between the base 1060 and the tip 1052. For example, in certain implementations, the tip length 1070 may be from and including 0.002 inches to and including 0.03 inches.

FIGS. 11A-14C illustrate fixation element embodiments having variations of leading point configurations. For example, leading point 1152, 1252, 1352, 1452 is located at different positions or is formed by the convergence of different numbers of bevel faces as compared to FIGS. 10A-10D. It will be appreciated that, even when the reference geometry and terminology used above, e.g., transverse plane 1051, longitudinal plane 1059, etc., is not explicitly used in the description below, the configurations are nonetheless implicitly described with such terms.

FIGS. 11A-11C are schematic illustrations of a primary helix 1100 according to the present disclosure. Primary helix 1100 is a fixation element 1100 having a leading point 1152 on distal edge 1007 distal to transverse plane 1051. More particularly, leading point 1152 is at the twelve o'clock position on longitudinal plane 1059. FIG. 11A is a side view of the primary helix 1100 and FIGS. 11B-11C are detail views of a distal helix end 1150 of the primary helix 1100. The primary helix 1100 may be formed from a wire coil 1102 and extend about a helix axis 1104. The wire coil 1102 forming the primary helix 1100 includes an outer perimeter 1106.

As shown in each of FIGS. 11A-11C, the distal helix tip 1150 may terminate in a sharpened tip 1152 formed by a double-bevel such that the tip 1152 is disposed on the outer perimeter 1106 of the wire coil 1102. In contrast to the primary helix 205 illustrated in FIGS. 10A-D in which the tip 1052 was disposed in a proximal or "six o'clock" position, the tip 1152 of the primary helix 1100 is position at a distal or "twelve o'clock" position. More specifically, the double bevel forming the tip 1152 results in an edge 1154 extending between the tip 1152 and base 1156. A vector 1158 distally extends from the base 1156 parallel to the helix axis 1104 such that a plane 1160 is defined by the helix axis 1104 and the vector 1158. In the "twelve o'clock" position, the angle θ between the vector 1158 and the base 1156 along the plane 1160 is substantially zero. The "twelve o'clock" position of the tip 1152 generally corresponds to a more aggressive tip as compared to the primary helix 205 of FIGS. 10A-10D. Accordingly, such a primary helix is more suitable for implantation in relatively thick cardiac tissue or implantation in locations in which overpenetration will not result in unnecessary trauma, e.g., a ventricle. As shown in FIG. 11B and similar to the tip 1052 of the primary helix 1000, the forward extension of the tip 1152 may be defined by a second angle ψ. More specifically, the second angle ψ may correspond to the angle at which the edge extends relative to the plane 1160. In certain implementations, W may be from and including 10 degrees to and including 60 degrees. The distal helix tip 1150 may also have a predetermined tip length 1170, which generally corresponds to the longitudinal distance between the base 1160 and the tip 1152. For example, in certain implementations, the tip length 1170 may be from and including 0.002 inches to and including 0.02 inches.

Figure 12A:
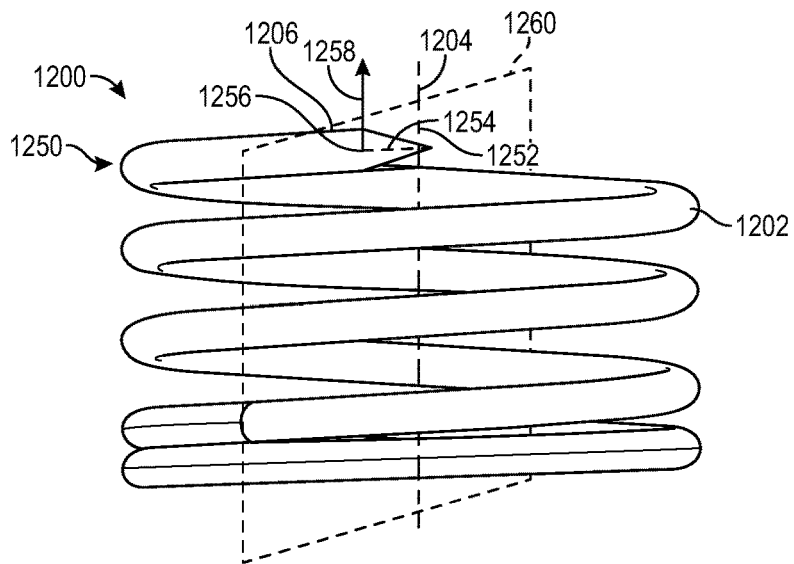
FIGS. 12A-12C are side elevation views of a fixation element in accordance with the present disclosure.
Figure 12B:
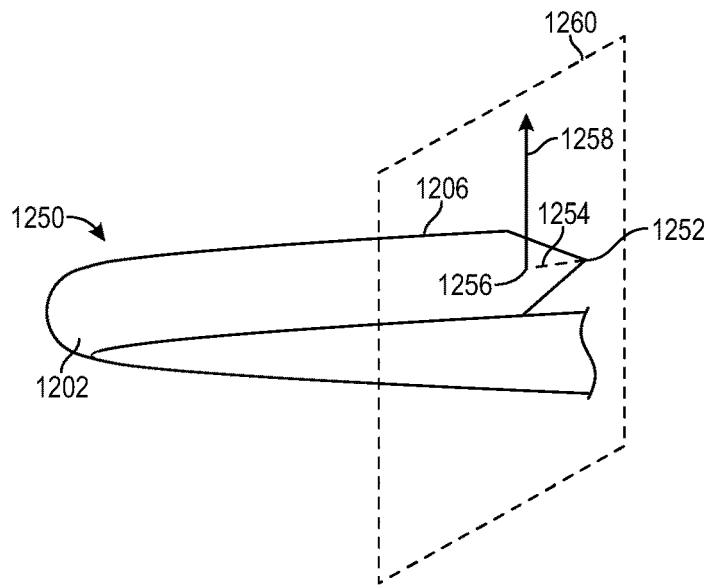
Figure 12C:
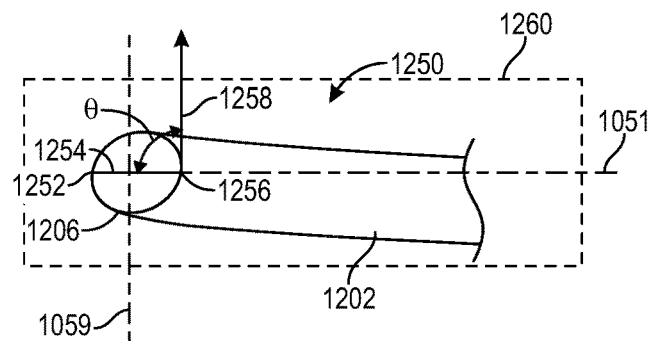

FIGS. 12A-12C are schematic illustrations of a primary helix 1200 according to the present disclosure. Primary helix 1200 is a fixation element 1200 having a leading point 1252 on distal edge 1007 along transverse plane 1051. More particularly, leading point 1252 is at the nine o'clock position on transverse plane 1051. Wire face 1209 has a double-bevel design such that two bevel faces converge at leading point 1252. FIG. 12A is a side view of the primary helix 1200 and FIGS. 12B-12C are detail views of a distal helix end 1250 of the primary helix 1200. The primary helix 1200 may be formed from a wire coil 1202 and extend about a helix axis 1204. The wire coil 1202 forming the primary helix 1205 includes an outer perimeter 1206.

As shown in each of FIGS. 12A-12C, the distal helix tip 1250 may terminate in a sharpened tip 1252 formed by a double-bevel such that the tip 1252 is disposed on the outer perimeter 1206 of the wire coil 1202. In contrast to the primary fixation helix 205 illustrated in FIGS. 10A-D in which the tip 1052 was disposed in a proximal or "six o'clock" position, the tip 1252 of the primary helix 1200 is positioned at an externally lateral or "9 o'clock" position. More specifically, the double bevel forming the tip 1252 results in an edge 1254 extending between the tip 1252 and base 1256. A vector 1258 distally extends from the base 1256 parallel to the helix axis 1204 such that a plane 1260 is defined by the helix axis 1204 and the vector 1258. In the "9 o'clock" position, the angle θ between the vector 1258 and the base 1256 along the plane 1260 is approximately 90 degrees. The "9 o'clock" position of the tip 1252 generally corresponds to a middle ground between the conservative "six o'clock" placement of the tip 1052 illustrated in FIGS. 10A-D and the aggressive "twelve o'clock" placement of the tip 1152 illustrated in FIGS. 11A-C.

As described above, tip positions have unique benefits in terms of device efficacy, e.g., anchoring, and safety. For example, tip position can shield the leading edge of the tip from pericardial pinning to reduce a likelihood of negative effects on long-term pacing performance. Accordingly, biostimulator 100 can be fabricated with a tip position that is specific to an intended implant location. By way of example, biostimulator 100 intended for implantation within a ventricle may be manufactured with a twelve o'clock tip position. By contrast, biostimulator 100 intended for implantation within an atrium may be manufactured with a six o'clock tip position.

As shown in FIGS. 10A-12C, the angle θ is measured away from the helix axis. However, in other implementations, the angle θ may instead be measured towards the helix axis. For example, an implementation in which the angle θ is approximately 90 degrees may correspond to a "3 o'clock" placement of the tip 1052 (i.e., opposite the placement of the tip 1252 illustrated in FIGS. 12A-C). Accordingly, to the extent this disclosure refers to the angle θ and provides ranges of the value of θ, such values may be based on the angle being measured towards or away from the helix axis.

In certain implementations of the present disclosure, the tip of the primary fixation helix may instead be provided with respect to an envelope defined by the primary helix. For example, FIG. 13A is a schematic illustration of a primary helix 1300 including a distal helix end 1350 with a sharpened tip 1352 and FIGS. 13B-13C are side and front views, respectively, of the distal helix end 1350.

Figure 13A:
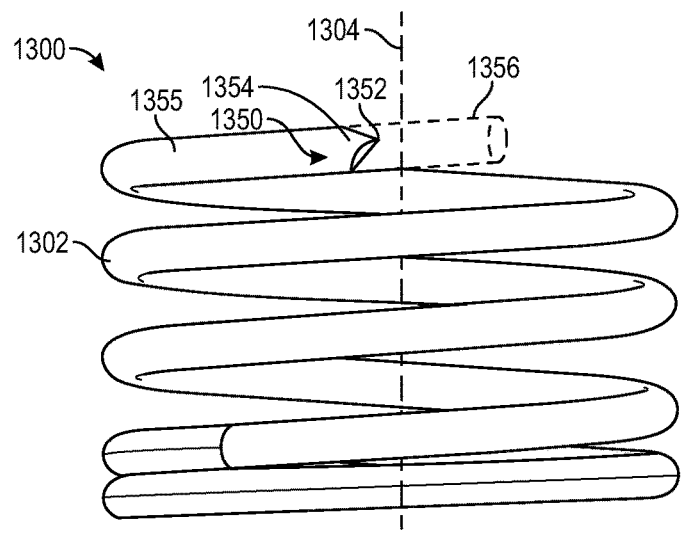
FIG. 13A-13C are side elevation views of a fixation element in accordance with the present disclosure.
Figure 13B:
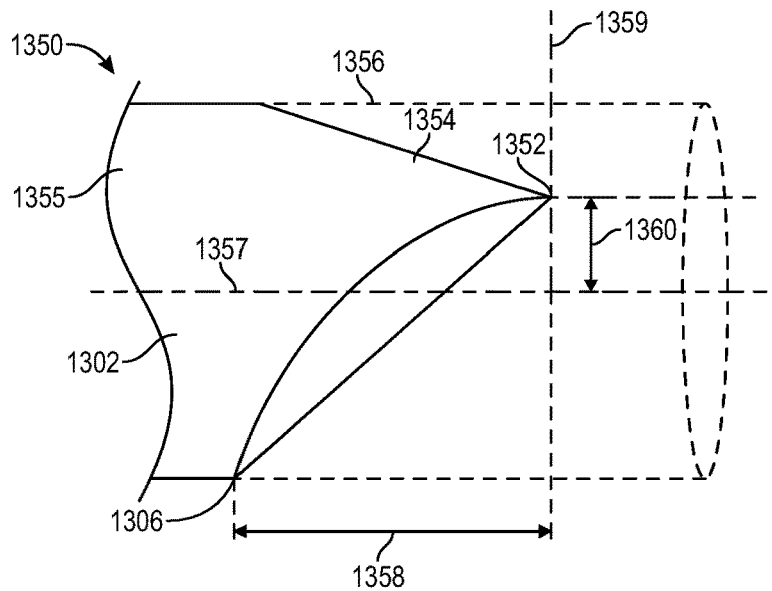
Figure 13C:
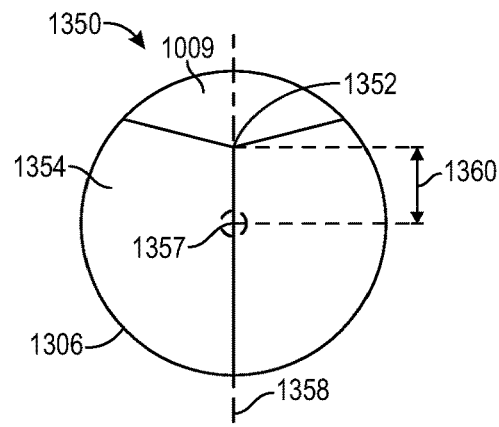

As shown in FIGS. 13A-13C, primary helix 1300 can be a fixation element 1300 having a leading point 1352 on wire face 1009 inward from distal edge 1306 and distal to transverse plane 1051. More particularly, leading point 1152 is along longitudinal plane 1059 in the direction of the twelve o'clock position. Wire face 1009 has a triple-bevel design such that three bevel faces converge at leading point 1252. The distal helix end 1350 is formed from a coil wire 1302 and includes a tapered portion 1354 terminating in the sharpened tip 1352. In contrast to the primary helices of FIGS. 10A-12C in which the respective sharpened tips were disposed about the perimeter, e.g., on the distal edge 1007, of the coil wire, the tip 1352 of the primary helix 1300 is disposed within a projected volume 1356 defined by an untapered portion 1355 of the coil wire 1302. The projected volume 1356 corresponds to a volume that would be occupied by the untapered portion 1355 if the untapered portion 1355 were to be extended beyond the tapered portion 1354. Accordingly, the tapered portion 1354 extends into and terminates at the tip 1352 within the projected volume 1356.

As shown in FIG. 13B, the position of the tip 1352 may be defined by a first distance 1358 from the end of the untapered portion 1354 and a second distance 1360 from a first axis 1357 defined by and extending longitudinally through the coil wire 1302. The second distance 1360 may be defined along a second axis 1359 that perpendicularly intersects a first axis 1357 and that is parallel to helix axis 1304 (shown in FIG. 13A). So, for example, in implementations in which the second distance 1360 is zero, the tip 1352 is disposed along the first axis 1357. In other implementations in which the second distance 1360 is non-zero, the tip 1352 is displaced relative to the first axis 1357. For example, the second distance 1360 of the primary helix 1300 of FIGS. 13A-13C is a non-zero value in the distal direction such that the tip 1352 is distally displaced relative to the first axis 1357. In other implementations, the second distance 1360 may correspond to a distance along the second axis 1359 in a substantially proximal direction.

In certain implementations, the first distance 1358 and the second distance 1360 may fall within predetermined ranges. For example, the first distance 1358 may be from and including 0.002 inches to and including 0.03 inches. Similarly, the second distance 1360 may be from and including 0.001 inches to and including 0.009 inches and, in one implementation, may be 0.004 inches. In one specific implementation, the first distance may be 0.01 inches and the second distance may be 0.004 inches.

Figure 14A:
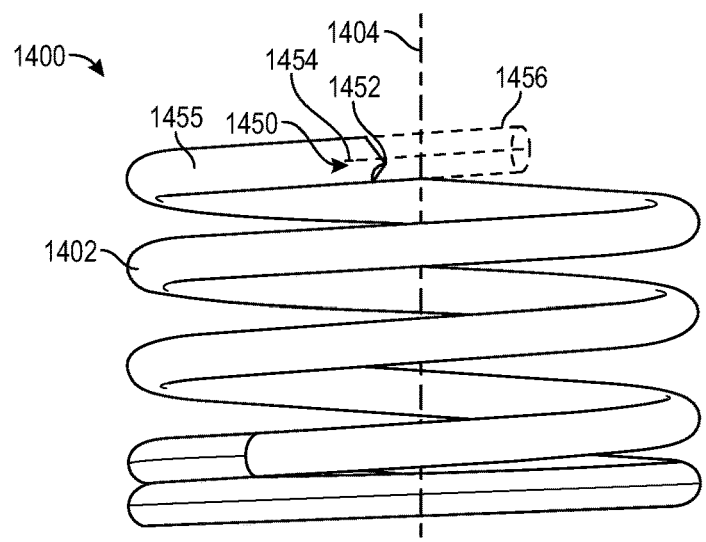
FIGS. 14A-14C are side elevation views of a fixation element in accordance with the present disclosure.
Figure 14B:
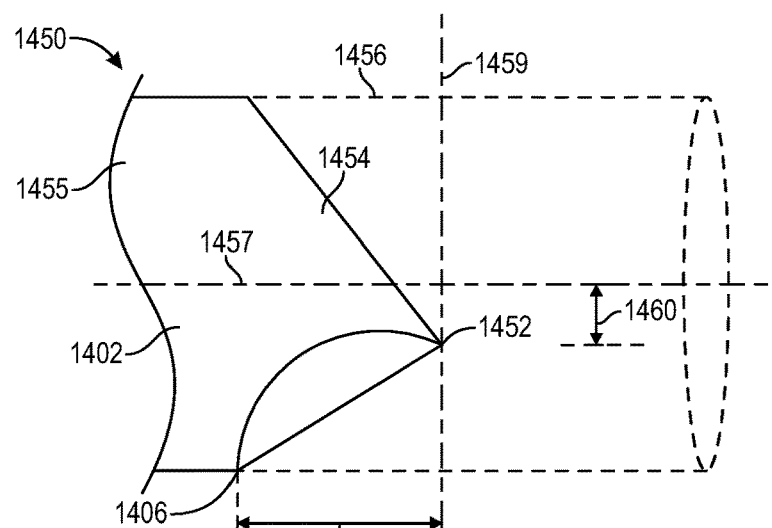
Figure 14C:
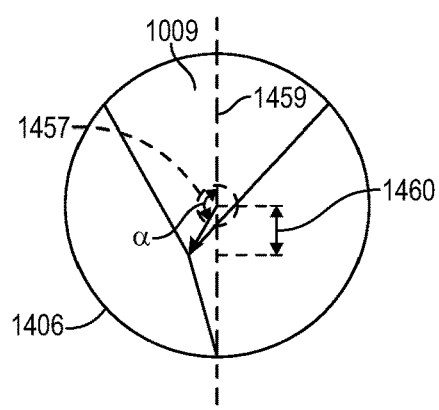

FIG. 14A is a schematic illustration of a primary helix 1400 including a distal helix end 1450 with a sharpened tip 1452 and FIGS. 14B-14C are side and front views, respectively, of the distal helix end 1450.

As shown in FIGS. 14A-14C, primary helix 1400 can be a fixation element 1400 having a leading point 1452 on wire face 1009 inward from distal edge 1406 and proximal to transverse plane 1051. More particularly, leading point 1452 is in a lower-left quadrant defined by the intersection of transverse plane 1051 and longitudinal plane 1059. Wire face 1009 has a triple-bevel design such that three bevel faces converge at leading point 1452. The distal helix end 1450 is formed from a coil wire 1402 and includes a tapered portion 1454 terminating in the sharpened tip 1452. Similar to the primary helix 1300 of FIGS. 13A-13C, the tip 1452 of the primary helix 1400 is disposed within a projected volume 1456 defined by an untapered portion 1455 of the coil wire 1402.

As shown in FIG. 14B, the position of the tip 1452 may be defined by a first distance 1458 from the end of the untapered portion 1454 and a second distance 1460 from a first axis 1457 defined by and extending longitudinally through the coil wire 1402. The second distance 1460 may be defined along a second axis 1459 that perpendicularly intersects the first axis 1456 and that is parallel to a helix axis 1404 (shown in FIG. 14A). In contrast to the primary helix 1300 of FIGS. 13A-13C, the position of the tip 1452 of the primary helix 1400 of FIGS. 14A-14C is further defined by an angle α relative to the second axis 1459. Accordingly, the tip 1452 is offset from each of the first axis 1458 and the second axis 1459.

In certain implementations, the first distance 1458 and the second distance 1460 may fall within predetermined ranges. For example, the first distance 1458 may be from and including 0.002 inches to and including 0.02 inches and the second distance 1460 may be from and including 0 inches to and including 0.01 inches. Similarly, the angle α may be in a range from and including 90 degrees to and including 160 degrees. In one specific implementation, for example, the first distance may be 0.008 inches, the second distance may be 0.002 inches and the angle α may be 120 degrees.

Figure 15:
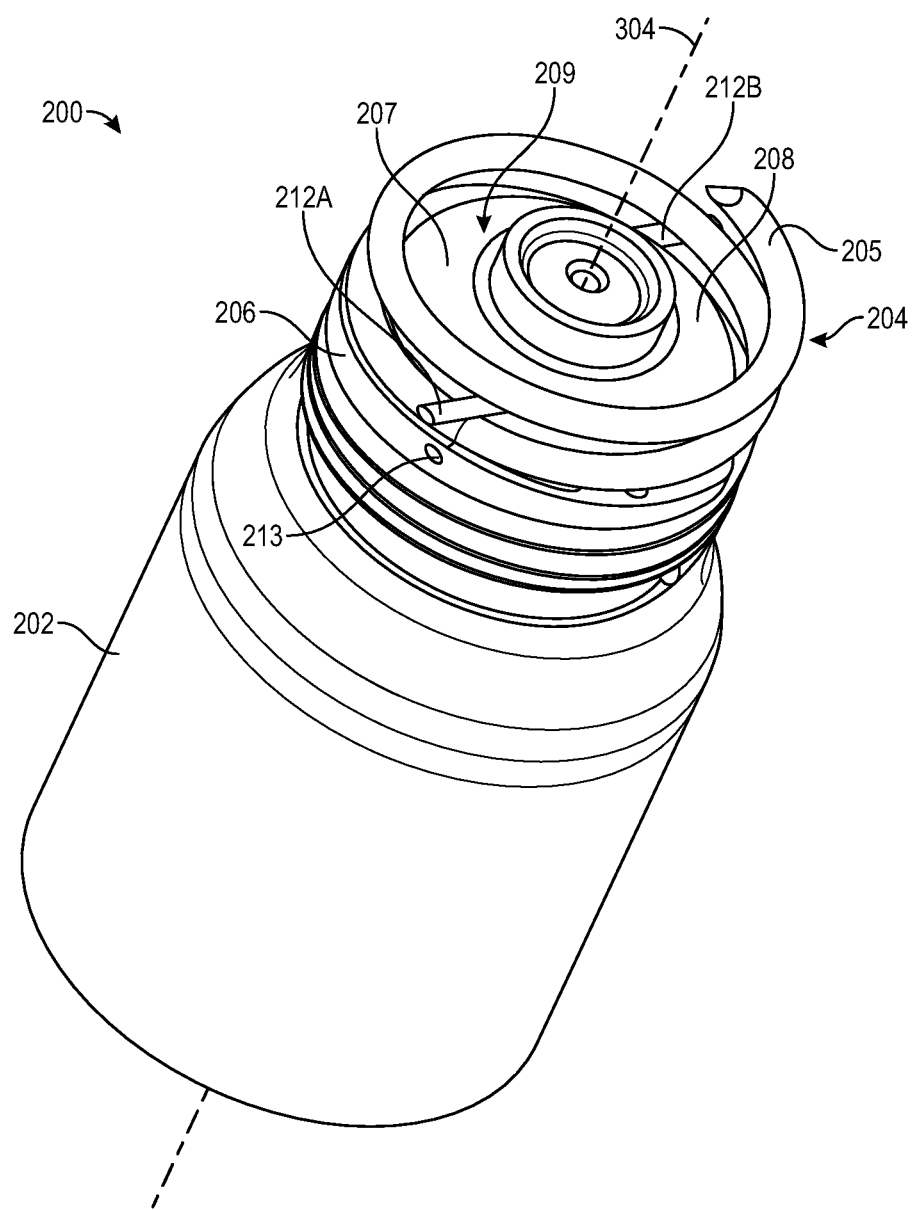
FIG. 15 is an isometric view of a biostimulator in accordance with the present disclosure.

FIG. 15 is an isometric view of the biostimulator 200 of FIG. 2 illustrating a suture arrangement. As previously discussed in the context of FIG. 2, the biostimulator 200 includes a housing 202 and a header assembly 204 coupled thereto. The header assembly 204 generally includes a primary fixation element 205, which in FIG. 15 is a primary helix 205, that extends about a longitudinal axis 304 defined by the biostimulator 200. The primary helix 205 may be formed of similar materials and have similar dimensional characteristics as previously discussed in the context of FIG. 2. As illustrated in FIG. 14, the primary helix 205 is coupled to the header assembly 204 such that the primary helix 205 extends distally beyond a distal face 207 of the header assembly 204. The distal face 207 may correspond to a distal end of the cap 208 of the header assembly 204.

In certain embodiments, the header assembly 204 further includes backstop features 212A, 212B that extend from the distal face 207. The anti-unscrewing features 212A, 212B of FIG. 15, for example, are flexible sutures 212A, 212B that extend from the distal face 207 of the biostimulator 200. In certain implementations, the sutures 212A, 212B may also extend at an angle opposite the direction of the primary helix 205, as discussed below in more detail. As previously discussed in the context of FIG. 2, the sutures 212A, 212B may be formed of various flexible biocompatible materials including, without limitation, one or more of polypropylene, polyethylene, polyester, nylon, polyurethane, silicone, poly (lactic acid) (PLA), poly(glycolic acid) (PGA), polyimide, polyether ether ketone (PEEK), and polycarbonate. Backstop features 212A, 212B can also be formed from the natural materials described above. As illustrated in FIG. 15, the biostimulator 200 may also include lateral cavities, such as lateral cavity 213, within which additional sutures may be disposed. Lateral cavities 213 can be bores in the sidewall of helix mount 206 through which backstop elements 203, e.g., non-metallic filaments, can be inserted and secured. Such sutures are illustrated, for example, as sutures 214A, 214B in FIG. 2.

Figure 16:
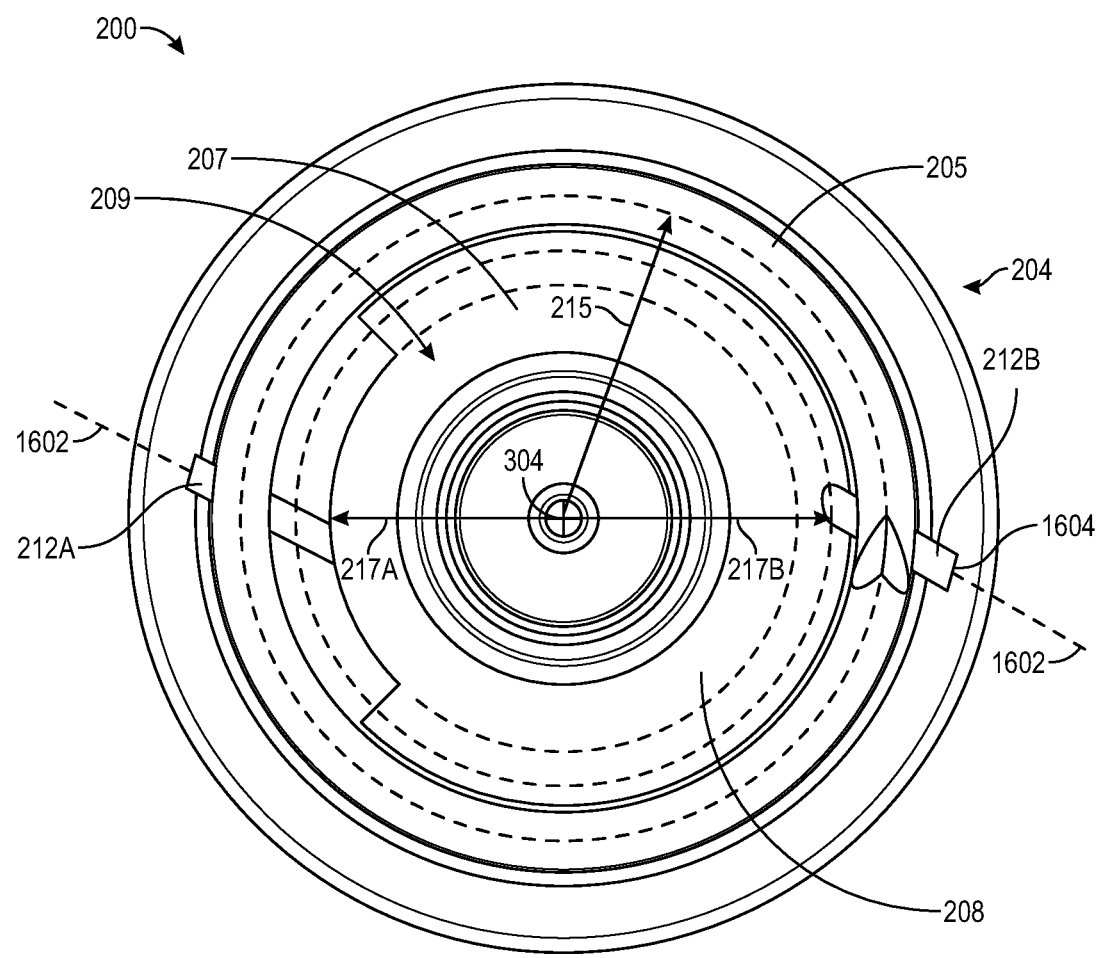
FIG. 16 is a distal view of the biostimulator in accordance with the present disclosure.

FIG. 16 is a distal view of the biostimulator 200 of FIG. 15. As illustrated, the primary helix 205 generally extends about the longitudinal axis 304 at a helix radius 215. The helix radius 215 generally corresponds to the pitch radius of the primary helix 205. In contrast, the sutures 212A, 212B originate from the distal face 207 at a first suture radius 217A and a second suture radius 217B, respectively. As illustrated in FIG. 16, the suture radii 217A, 217B may differ for each suture; however, in general, each suture radius may be less than the helix radius 215 such that the sutures 212A, 212B extend, at least partially, through a volume 209 defined by the primary helix 205. As illustrated in FIG. 16, the sutures 212A, 212B may also extend along respective filament axes 1602 to respective filament tips 1604. The backstop elements 212A, 212B can extend beyond the helix radius 215 such that the sutures 212A, 212B terminate outside of the volume 209. When extending beyond the helix radius 215, each of the sutures 212A, 212B may extend between adjacent turns of the primary helix 205, as discussed below in the context of FIGS. 18-19 in more detail.

Figure 17:
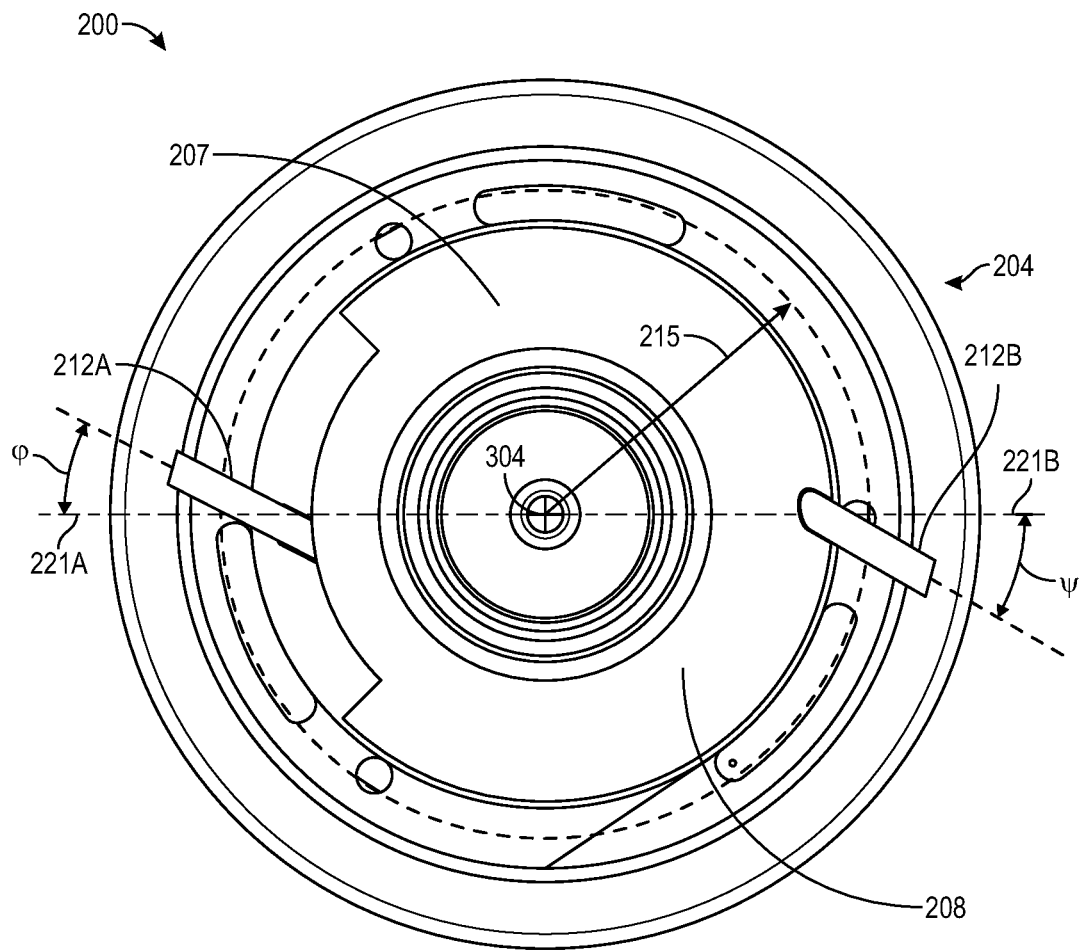
FIG. 17 is a distal view of a biostimulator having a fixation element removed in accordance with the present disclosure.

FIG. 17 is a distal view of the biostimulator 200 of FIG. 15 with the primary helix 205 removed for clarity. As indicated in FIG. 17, each of the sutures 212A, 212B may be "swept" such that they extend, at least in part, in a direction opposite the rotational direction of the primary helix 205. Such counter directional biasing of the sutures 212A, 212B may, in certain implementations, improve the resistance provided by the sutures 212A, 212B to unscrewing of the primary helix 205. In FIG. 17, for example, each of the sutures 212A, 212B extend at an angle β relative to respective lines 221A, 221B extending from the longitudinal axis 304 to their respective origins. In certain implementations, the angle φ may be from and including 15 degrees to and including 75 degrees.

Figure 18:
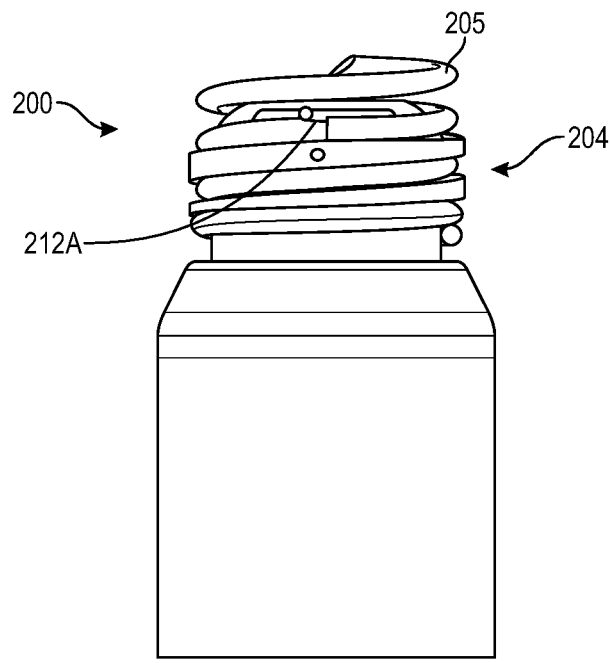
FIG. 18 is a side elevation view of a biostimulator in accordance with the present disclosure.
Figure 19:
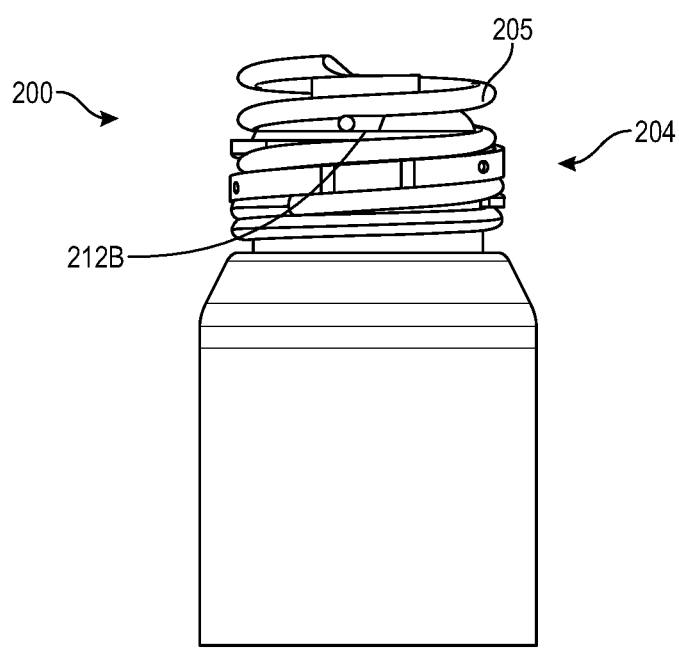
FIG. 19 is a side elevation view of a biostimulator in accordance with the present disclosure.

FIGS. 18-19 are side elevation views of the biostimulator 200 intended to illustrate the relative longitudinal placement of the sutures 212A, 212B and the primary helix 205. As previously noted, in certain implementations, the sutures 212A, 212B may be arranged such that they extend between adjacent turns of the primary helix 205. In other words, the primary helix 205 is configured to distally extend beyond each of the sutures 212A, 212B. In such implementations, the primary helix 205 must be screwed in a predetermined number of turns before the sutures 212A, 212B are able to engage tissue adjacent the implantation location of the primary helix 205. In certain implementations, the primary helix 205 may extend from and including an eighth of a turn to and including two full turns beyond the sutures 212A, 212B. As illustrated in FIG. 18, for example, the primary helix 205 extends approximately one half turn beyond the suture 212A. As illustrated in FIG. 19, the primary helix extends approximately one full turn beyond the suture 212B. As illustrated in the embodiments of FIGS. 18 and 19, if the helix is engaged one to one and a half turns into tissue, then the placement of the sutures will be within the tissue, guaranteeing activation of the backstop elements.

The sutures 212A, 212B are illustrated in FIGS. 15-19 as extending substantially perpendicular to the longitudinal axis 304 of the biostimulator 200. In other implementations, such as discussed in FIGS. 2-9B, biostimulators in accordance with the present disclosure may include sutures that extend distally along filament axes to filament tips, at least in part. The biostimulator 200 of FIG. 2, for example, includes sutures 212A, 212B that extend in a partially distal direction from the cap 208. As discussed in the context of FIG. 3, such sutures may extend from and including 15 degrees to and including 75 degrees relative to a longitudinal axis 304 of the biostimulator 200. Such sutures 212A, 212B may also be "swept" at an angle such that they are directed, in part, counter to the direction of the primary helix 205. Such an angle may, in certain implementations, be from and including 15 degrees to and including 75 degrees. Notably and similar to the implementation of FIGS. 15-19, FIG. 2 illustrates the suture 212B as extending between adjacent turns of the primary helix 205 such that the primary helix 205 extends approximately one eighth of a turn beyond the suture 212B.

Figure 20:
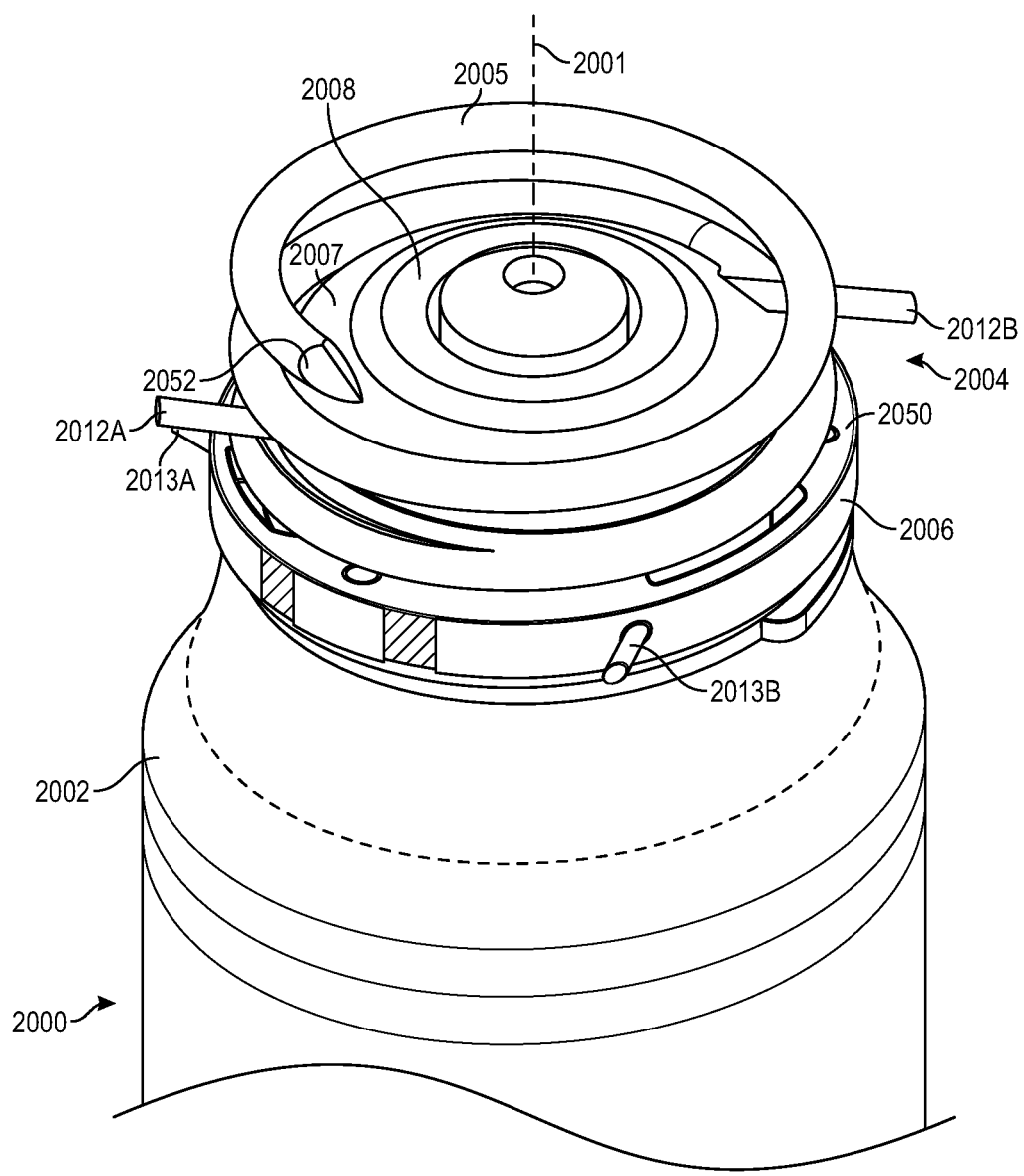
FIG. 20 is an isometric view of a biostimulator in accordance with this disclosure.
Figure 21A:
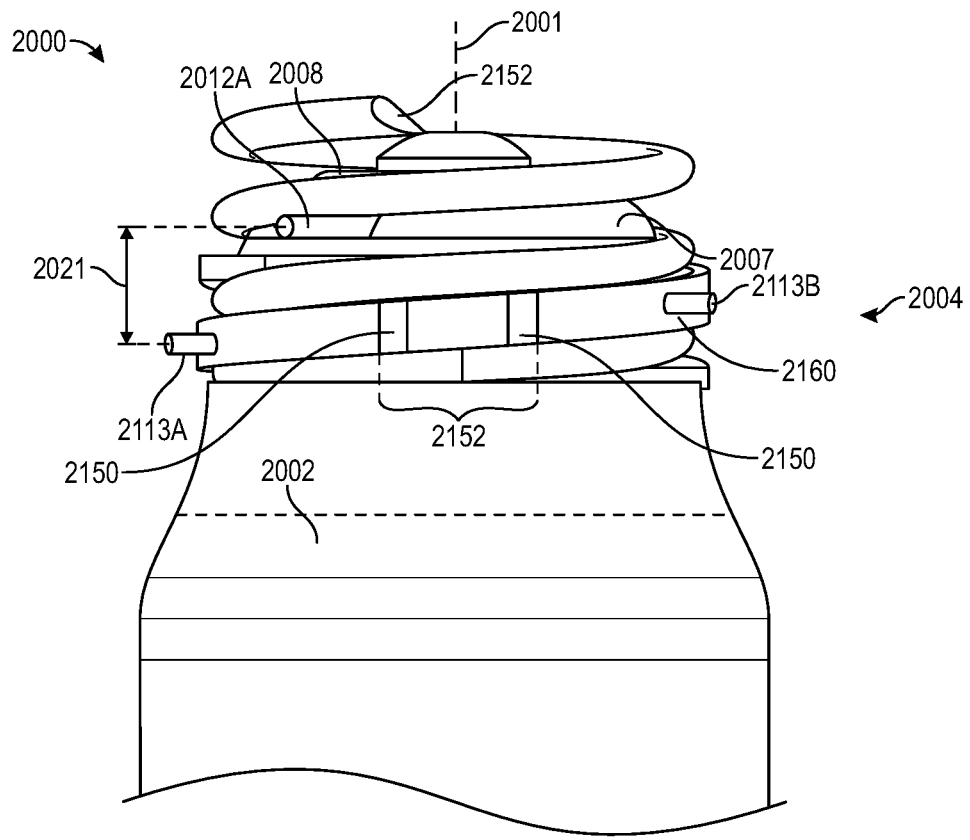
FIGS. 21A and B are lateral side views of a distal portion of a biostimulator in accordance with the present disclosure.
Figure 21B:
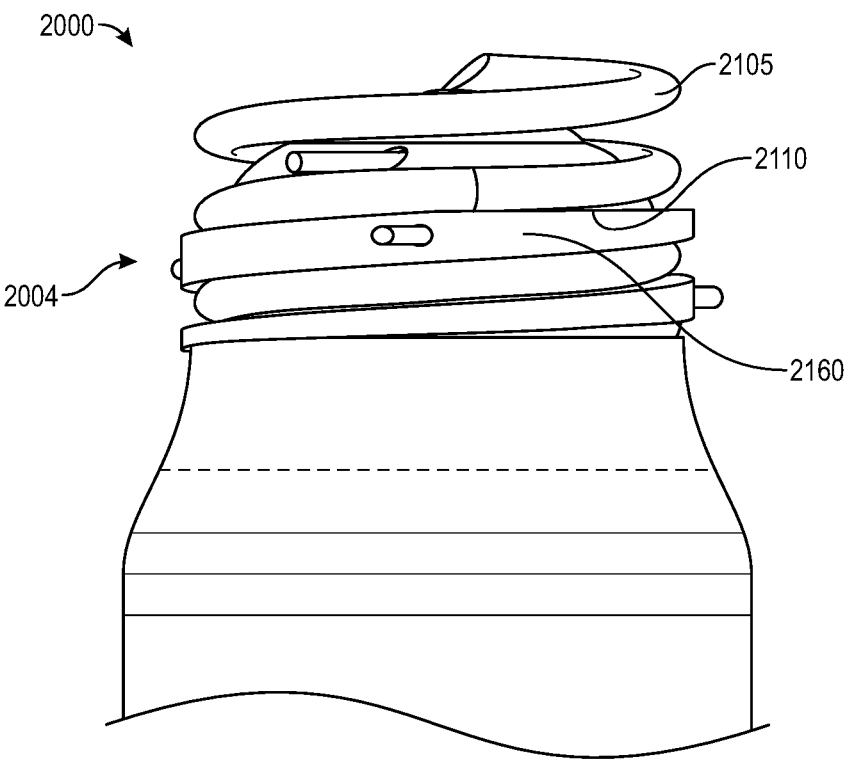
Figure 22:
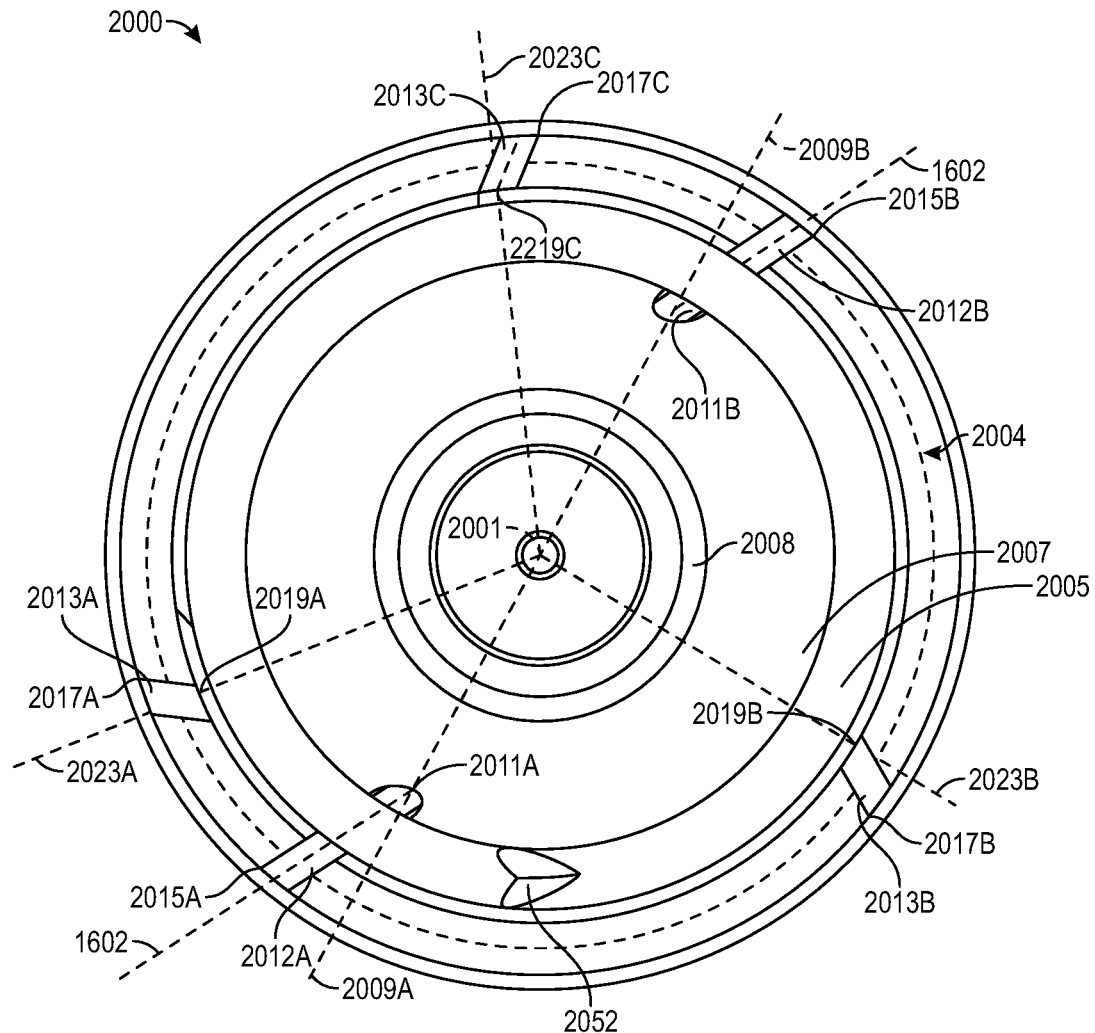
FIG. 22 is a distal end view of a biostimulator in accordance with the present disclosure.

FIGS. 20-22 illustrate an example biostimulator 2000 incorporating various concepts previously described in this disclosure. More specifically, FIG. 20 is a first isometric view of the biostimulator 2000, FIGS. 21A-B are lateral side views of the biostimulator 2000 focusing on a distal end of the biostimulator 2000 and FIG. 22 is a distal view of the biostimulator 2000.

Although other configurations are possible, the biostimulator 2000 illustrates one specific configuration found to have advantageous performance characteristics during testing. Accordingly, to the extent specific characteristics of the biostimulator 2000 and its components are provided below, such discussion is intended to be non-limiting and to provide merely one example of a biostimulator in accordance with this disclosure.

Referring to FIGS. 20-21, the biostimulator 2000 includes a housing 2002 and a header assembly 2004 coupled thereto. The header assembly 2004 generally includes a primary fixation element 2005 in the form of a primary helix 2005, that extends about a longitudinal axis 2001 defined by of the biostimulator 2000. The primary helix 2005 may be formed of similar materials and have similar dimensional characteristics as previously discussed in the context of FIG. 2. As illustrated in FIG. 20, the primary helix 2005 is coupled to the header assembly 2004 such that the primary helix 2005 extends distally beyond a distal face 2007 of the header assembly 2004. The distal face 2007 may correspond to a distal end of the cap 2008 of the header assembly 2004. Distal face 2007 may not be perpendicular to axis 2001, however.

Figure 23:
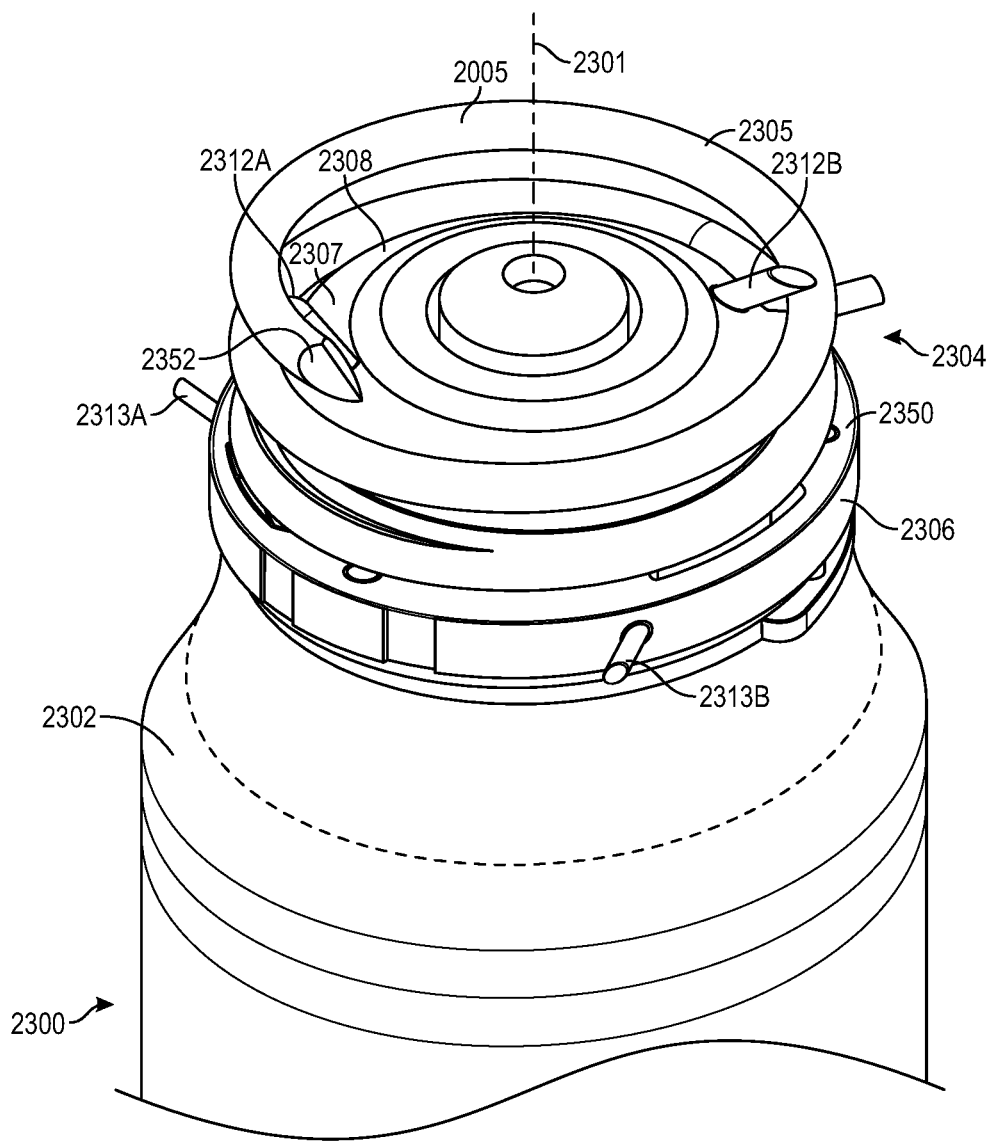
FIG. 23 is an isometric view of a biostimulator in accordance with the present disclosure.

The header assembly 2004 further includes distal lateral sutures 2012A, 2012B that extend laterally from the distal face 2007 and proximal lateral sutures 2013A-2013C that extend laterally from a helix mount 2006 of the header assembly 2004 proximal to the distal lateral sutures 2012A, 2012B. In general, each of the distal lateral sutures 2012A, 2012B and the proximal lateral sutures 2013A-2013C (proximal lateral suture 2013C is shown in FIG. 23) extend laterally at an angle opposite the direction of the primary helix 2005.

The primary helix 2005 includes a single, helically wound wire that is sized to couple the biostimulator 2000 to cardiac tissue while minimizing damage to the cardiac tissue. As most clearly visible in FIGS. 20 and 21, the primary helix 2005 extends approximately 1.5 turns from a distal end 2050 of the helix mount 2006. In general, extending approximately 1.5 turns from the distal end 2050 of the helix mount 2006 provides a balance between the ease with which the primary helix 2005 may be made to engage the wall of the heart and the strength of such engagement. The primary helix 2005 is also formed of a wire having a diameter of approximately 0.016 inches and a pitch of approximately 0.032 inches. Regarding material, the primary helix 2005 is formed of type-302 stainless steel, which has a yield/ultimate tensile strength of approximately 350 kilopound per square inch (ksi). Other biocompatible materials having similar properties may also be used in other implementations. For example, in one implementation, instead of type-302 stainless steel, an alloy such as 35N LT® may be used for the primary helix 2005.

Similar to the primary helix 1200 illustrated in FIGS. 12A-12C, the primary helix 2005 can include a sharpened tip 2052 that may be formed, for example, by a double-bevel and that is disposed on an outer perimeter of the wire forming the primary helix 2005. As shown, the sharpened tip 1252 is disposed at approximately a "9 o'clock" position, however, that position can be different as described above. In other words, the sharpened tip 2052 is disposed on a lateral extent of the primary helix 2005 relative to the longitudinal axis 2001.

As illustrated in each of FIGS. 20-22, the biostimulator 2000 includes a pair of distal lateral sutures 2012A, 2012B that extend laterally from a cap 2008 disposed at a distal end of the biostimulator 2000. It is noted that, although FIGS. 20-22 illustrate fixation element 2005 extending 2 turns beyond helix mount 2006, the helical anchor may extend by another amount, e.g., between 1.5 to 2.5 turns, beyond the helix mount. For example, the fixation element can extend more than 2.5 turns from the helix mount, and thus, the illustration is provided by way of example and not limitation. The distal lateral sutures 2012A, 2012B are distributed about the cap 2008 such that they are disposed approximately 180 degrees apart from each other. The distal lateral sutures 2012A, 2012B are also disposed at locations that are offset approximately 90 degrees and 270 degrees, respectively, from the tip 2052 of the primary helix 2005.

In the specific example of the biostimulator 2000, the distal lateral sutures 2012A, 2012B are #3-0 sutures having a diameter ranging from and including approximately 0.2 millimeters to and including approximately 0.25 millimeters and are formed from polypropylene. As illustrated in FIG. 22, each of the distal lateral sutures 2012A, 2012B extends laterally from the distal cap 2008 such that a filament tip 2015A, 2015B of each suture 2012A, 2012B extends approximately 0.045 inches (+/−0.005 inches) from the cap 2008. In other implementations, the sutures 2012A, 2012B may extend from the distal cap 2008 by a distance from and including 0.020 inches to and including 0.080 inches. The suture 2012A extends at an angle of approximately 30 degrees relative to a first distal radial line 2009A extending from the longitudinal axis 2001 through an origin 2011A of the suture 2012A, the origin 2011A corresponding to a location of the cap 2008 from which the suture 2012A emerges. Similarly, the suture 2012B also extends at an angle of approximately 30 degrees relative to a second distal radial line 2009B extending from the longitudinal axis 2001 through an origin 2011B of the suture 2012B, the origin 2011B corresponding to a location of the cap 2008 from which the suture 2012B emerges. In other implementations, the distal sutures 2012A, 2012B may extend relative to their respective distal radial lines 2009A, 2009B at an angle from and including 15 degrees to and including 75 degrees.

In an embodiment, each filament tip can be shaped to have a filament face along the respective filament axis 1602, which is at an angle to the filament axis. For example, as shown, each tip 2015A, 2015B can be cut or trimmed at approximately a 30 degree angle relative to the respective filament axes.

As previously discussed, in addition to the distal lateral sutures 2012A, 2012B, the leadless biostimulator 2000 further includes a set of proximal lateral sutures 2013A-2013C extending from the helix mount 2006. The proximal lateral sutures 2013A-2013C are evenly distributed about the helix mount 2006 such that they are disposed 120 degrees apart from each other. The proximal lateral sutures 2013A-2013C are also disposed at locations that are offset approximately 60 degrees, 180 degrees, and 300 degrees, respectively, from the tip 2052 of the primary helix 2005. In another example implementation, the proximal lateral sutures 2013A-2013C may instead be disposed at locations that are offset approximately 45 degrees, 165 degrees, and 285 degrees, respectively, from the tip 2052 of the primary helix 2005. In still other implementations, the proximal lateral sutures 2013A-2013C may instead be disposed at locations that are offset from and including 30 degrees to and including 70 degrees, from and including 150 degrees to and including 190 degrees, and from and including 270 degrees to and including 320 degrees, respectively, from the tip 2052 of the primary helix 2005.

In an embodiment, the backstop elements, e.g., the non-metallic filaments 2013A-2013C, can extend through respective bores in the sidewall of helix mount. Furthermore, the bores can be at different longitudinal positions relative to longitudinal axis 304 such that the backstop elements 203 are longitudinally offset from each other. As illustrated in FIG. 21A, the proximal lateral sutures 2013A-2013C may be longitudinally offset from the distal lateral sutures 2012A, 2012B by a distance 2021 of approximately 0.010 inches. In other implementations, the distance 2021 may be from and including 0.005 inches to and including 0.050 inches. Also, as illustrated in FIG. 21, the longitudinal distance between the distal lateral sutures 2012A, 2012B and the proximal lateral sutures 2013A-2013C may vary for each of the proximal lateral sutures 2013A-2013C. For example, the helix mount 2006 may have a helical shape and the proximal lateral sutures 2013A-2013C may extend at various points along the helical shape such that each of the proximal lateral sutures 2013A-2013C is disposed at a different longitudinal location.

In the specific example of the biostimulator 2000, the proximal lateral sutures 2013A-2013C are #4-0 sutures having a diameter ranging between approximately 0.15 mm and 0.2 mm and are formed from nylon. As illustrated in FIG. 22, each of the proximal lateral sutures 2013A-2013C extends laterally from the helix mount 2006 such that a tip 2017A-2017C of each suture 2013A-2013C extends approximately 0.020 inches (+/−0.005 inches) from the helix mount 2006. In other implementations, the sutures 2013A-2013C may extend from the helix mount 2006 by a distance from and including 0.010 inches to and including 0.030 inches. The suture 2013A extends at an angle of approximately 30 degrees relative to a first proximal radial line 2023A extending from the longitudinal axis 2001 through an origin 2019A of the suture 2013A, the origin 2019A corresponding to a location of the helix mount 2006 from which the suture 2013A emerges. The suture 2013B also extends at an angle of approximately 30 degrees relative to a second proximal radial line 2023B extending from the longitudinal axis 2001 through an origin 2019B of the suture 2013B, the origin 2019B corresponding to a location of helix mount 2006 from which the suture 2012B emerges. Finally, the suture 2013C extends at an angle of approximately 30 degrees relative to a third proximal radial line 2023C extending from the longitudinal axis 2001 through an origin 2019C of the suture 2013C, the origin 2019C corresponding to a location of helix mount 2006 from which the suture 2013C emerges. In other implementations, the proximal sutures 2013A-2013C may extend relative to their respective proximal radial lines 2023A-2023C at an angle from and including 15 degrees to and including 75 degrees.

In an embodiment, each filament tip can be shaped to have a filament face along the respective filament axis 1602, which is at an angle to the filament axis. For example, filament tips 2015A, 2015B can be cut or trimmed at approximately a 30 degree angle relative to the respective filament axes 1602.

Referring to FIG. 21B, in an embodiment, the several backstop elements 2113A, B and 2012A of biostimulator 2100 can include a pinch point 2110 between the wire of fixation element 2105 and a surface of the helix mount 2106. For example, fixation element 2105 can spiral proximally from the leading point until the wire abuts helix mount flange 2160. More particularly, an upper surface of helix mount flange 2160 can appose the outer surface of the wire at a pinch point 2110. Pinch point 2110 is between the wire and the distal end of helix mount flange 2160 such that, as fixation element 2005 screws into tissue, the captured tissue will become wedged between the wire and the helix mount flange at the pinch point. When tissue is wedged at the pinch point 2110, the clamping force applied to the tissue causes biostimulator 100 to resist back-out forces applied by the dynamic operating environment. Accordingly, pinch point 2110 acts as another fixation mechanism that resists the backward movement of fixation element 2005.

Figure 26:
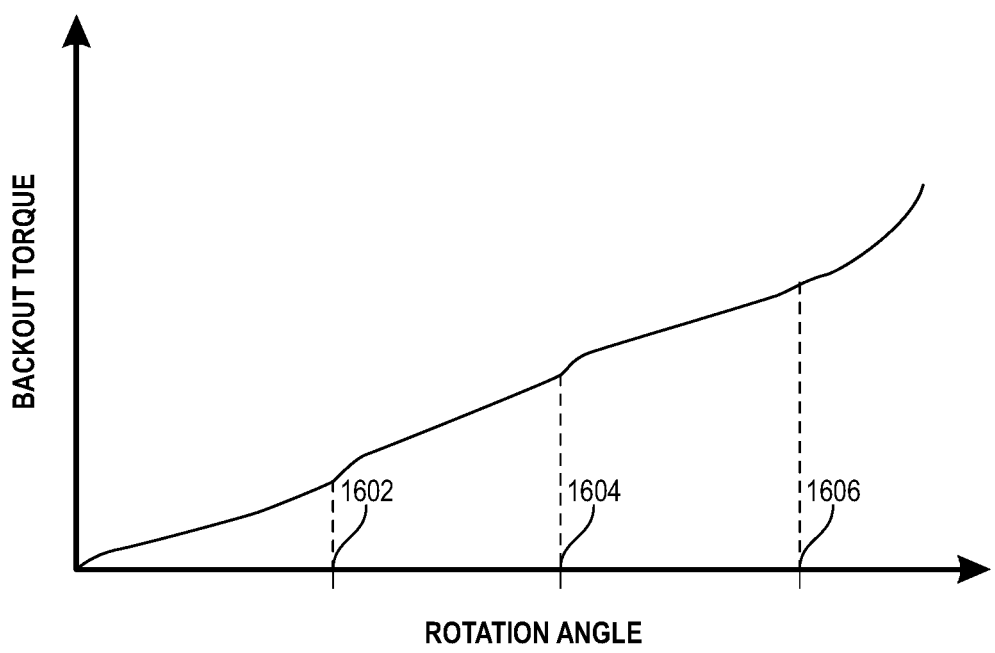
FIG. 26 is a graphical view of a back-out torque of a biostimulator in accordance with the present disclosure.

Referring to FIG. 26, a graphical view of a back-out torque of a biostimulator is shown in accordance with an embodiment. The graph can plot back-out torque against rotation angle, where the rotation angle corresponds to different tissue engagement events. For example, as fixation element 205 engages and screws into tissue, the back-out torque required to dislodge biostimulator can be zero when the leading point initially punctures the target tissue to a first value when a first backstop element 203 engages the target tissue at rotation angle 1602. The required back-out torque can experience a step increase at rotation angle 1602 because dislodgment requires not only overcoming the friction of the wire within the target tissue, but also the resistance torque provided by the first backstop element. As more backstop elements engage the target tissue, the required back-out torque can increase. For example, rotation angle 1602 can correspond to engagement of a forward facing non-metallic filament with the target tissue, and rotation angle 1604 can correspond to engagement of a side facing non-metallic filament with the target tissue. At rotation angle 1604, the back-out torque can experience another step increase because the additional backstop element(s) further resist back-out.

In an embodiment, the removal torque increases further when fixation element 205 engages tissue and the tissue is wedged in the pinch point 2110. For example, when the tissue is at the pinch point, tissue shearing may occur. The tissue shearing can cause localized scarring, which can increase adhesion between the target tissue and the wire of fixation element 205. The increased adhesion can in turn cause a substantial increase in removal torque required to dislodge biostimulator 100. For example, the biostimulator can have a first removal torque when fixation element is engaged in tissue and the tissue is not at the pinch point 2110, and biostimulator 100 can have a second, higher, removal torque when fixation element is engaged in the tissue and the tissue is at the pinch point 2110. The latter case is shown at rotation angle 1606. In an embodiment, a rate of increase in back-out torque ramps upward at position 1606 because more shearing occurs as the pinch point advances over the tissue, and the scarring provides an increase in adhesion that has a relatively higher resistance to back-out. By way of example, the second removal torque when tissue is at pinch point can be at least 10% higher than the first removal torque when tissue is not at pinch point.

During testing, a biostimulator having characteristics of the biostimulator 2000 exhibit significant performance benefits as compared to conventional biostimulator designs. In particular, the design showed significant improvements in tests designed to assess torque-out for the biostimulator. During the test, biostimulators including primary helices and having varying suture designs were equally implanted (1.5 turns) within porcine atrial tissue. A counter-rotational torque was then applied and measured until disengagement of the biostimulator occurred. Notably, biostimulators including a primary helix and distal and proximal lateral sutures in accordance with the foregoing description of the biostimulator 2000 exhibited, on average, a greater than 300% increase in torque-out value as compared to conventional leadless pacemaker designs. Moreover, designs including both proximal and lateral sutures exhibited approximately 50% better torque-out values as compared to designs including distal sutures alone.

The specific configuration of the biostimulator 2000 illustrated in FIGS. 20-22 and described above in more detail exhibited strong performance characteristics during testing. Nevertheless, while the biostimulator 2000 represents one possible arrangement of components, it is provided merely as an example intended to illustrate one specific configuration in accordance with this disclosure. As described throughout this disclosure, other arrangements may be possible and may exhibit other advantages and favorable performance characteristics. Accordingly, the scope of this disclosure should not be limited to the specific implementation of FIGS. 20-22.

Figure 24A:
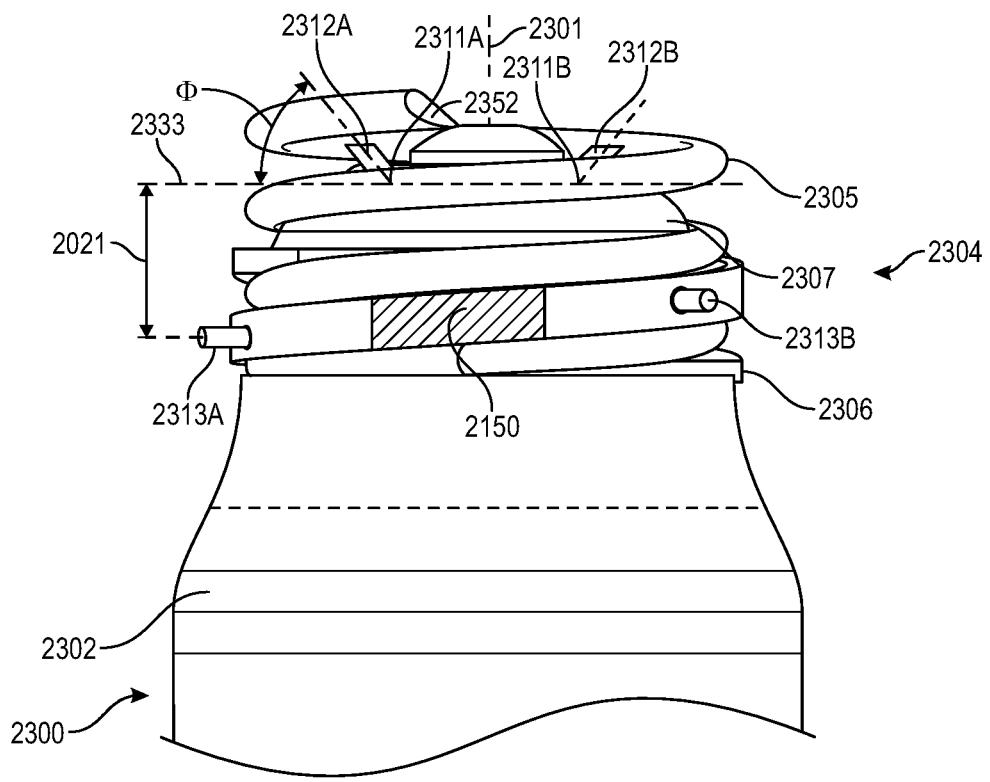
FIGS. 24A and B are lateral side views of a distal portion of the example biostimulator in accordance with the present disclosure.
Figure 24B:
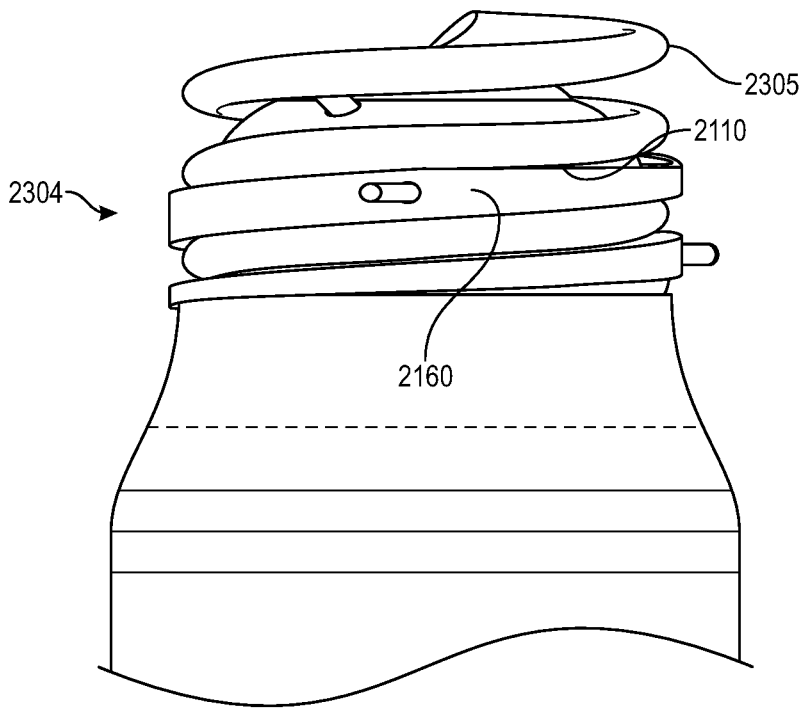
Figure 25:
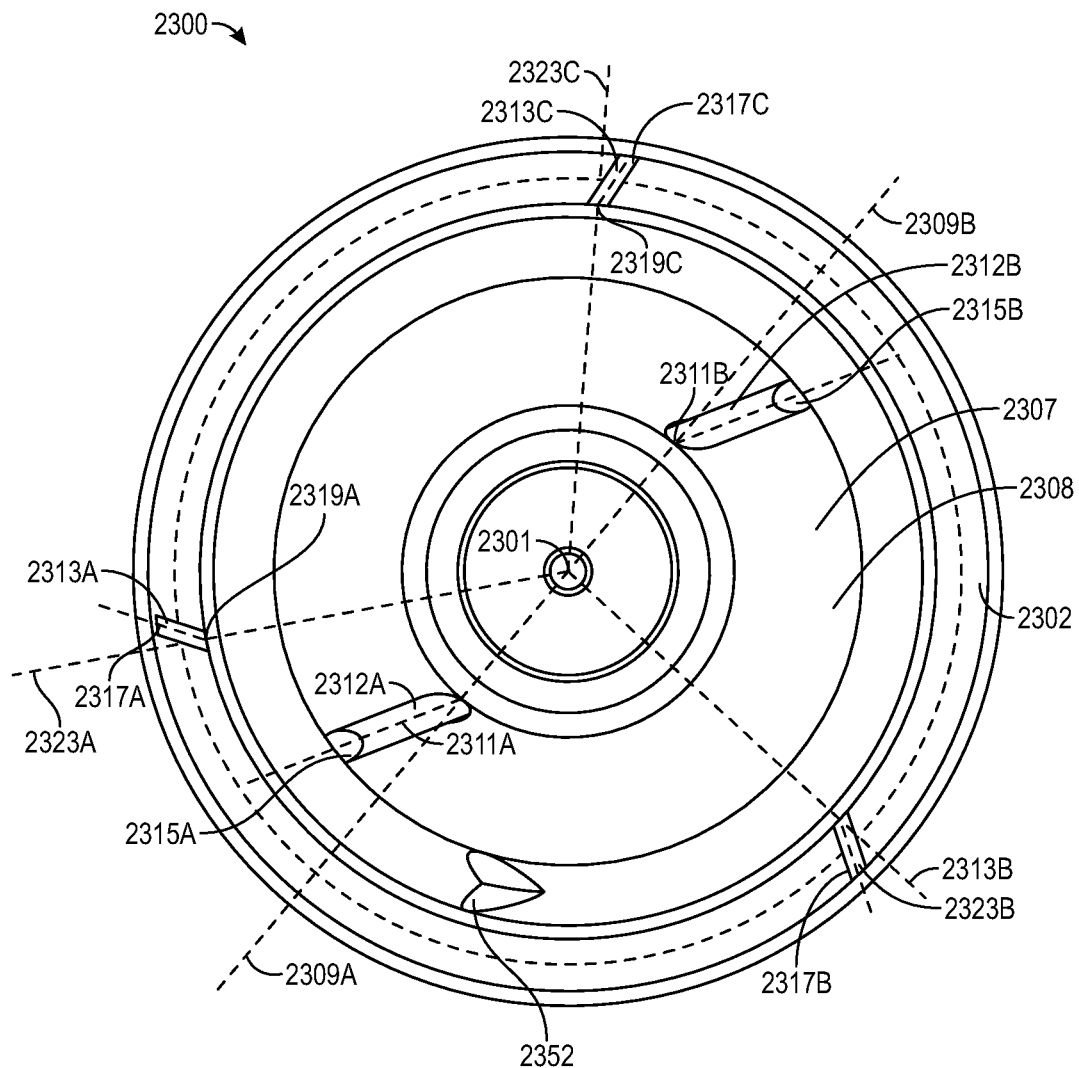
FIG. 25 is a distal end view of a biostimulator in accordance with the present disclosure.

FIGS. 23-25 illustrate another example biostimulator 2300 incorporating various concepts previously described in this disclosure. More specifically, FIG. 23 is a first isometric view of the biostimulator 2300, FIG. 23 is a second isometric view of the biostimulator 2300 focusing on a distal end of the biostimulator 2300. FIG. 25 is a distal view of the biostimulator 2300.

Although other configurations are possible, the biostimulator 2300 illustrates one specific configuration found to have advantageous performance characteristics during testing. Accordingly, to the extent specific characteristics of the biostimulator 2300 and its components are provided below, such discussion is intended to be non-limiting and to provide merely one example of a biostimulator in accordance with this disclosure.

Referring first to FIGS. 23-24, the biostimulator 2300 includes a housing 2302 and a header assembly 2304 coupled thereto. The header assembly 2304 generally includes a primary fixation element 2305 in the form of a primary helix 2305 that extends about a longitudinal axis 2301 of the biostimulator 2300. The primary helix 2305 may be formed of similar materials and have similar dimensional characteristics as previously discussed in the context of FIG. 2. As illustrated in FIG. 23, the primary helix 2305 is coupled to the header assembly 2304 such that the primary helix 2305 extends distally beyond a distal face 2307 of the header assembly 2304. The distal face 2307 may correspond to a distal end of the cap 2308 of the header assembly 2304.

The header assembly 2304 further includes distal sutures 2312A, 2312B that extend from the distal face 2307 in at least a partially distal direction and proximal lateral sutures 2313A-2313C that extend laterally from a helix mount 2306 of the header assembly 2304 proximal the distal lateral sutures 2312A, 2312B. As described below in more detail, each of the distal sutures 2312A, 2312B and the proximal lateral sutures 2313A-2313C extend at an angle opposite the direction of the primary helix 2305.

The primary helix 2305 is substantially similar to the primary helix 2005 described above in the context of the biostimulator 2000. Specifically, the primary helix 2305 extends approximately 1.5 turns from a distal end 2350 of the helix mount 2306 and is formed of a wire having a diameter of approximately 0.016 inches and a pitch of approximately 0.032 inches. The primary helix 2305 may be formed of type-302 stainless steel or similar biocompatible material.

The primary helix 2305 includes a sharpened tip 2352 that may be formed, for example, by a double-bevel and that is disposed on an outer perimeter of the wire forming the primary helix 2305. As shown, the sharpened tip 2352 is disposed at approximately a "9 o'clock" position. In other words, the sharpened tip 2352 is disposed on a lateral extent of the primary helix 2305 relative to the longitudinal axis 2301.

As illustrated in each of FIGS. 23-25, the biostimulator 2300 includes a pair of distal sutures 2312A, 2312B that extend from a cap 2308 disposed at a distal end of the biostimulator 2300. The distal sutures 2312A, 2312B are distributed about the cap 2308 such that they are disposed approximately 180 degrees apart from each other. The distal sutures 2312A, 2012B are also disposed at locations that are offset approximately 90 degrees and 270 degrees, respectively, from the tip 2352 of the primary helix 2305.

In the specific example of the biostimulator 2300, the distal sutures 2312A, 2312B are #3-0 sutures having a diameter ranging between approximately 0.2 mm and 0.3 mm and are formed from polypropylene. As illustrated in FIG. 25, each of the distal sutures 2312A, 2312B extends from the distal face 2307 in a direction that is at least partially in the distal direction. The extent to which each of the distal sutures 2312A, 2312B extend from the distal face 2307 may vary, however, in the illustrated implementation, each of the distal sutures 2312A, 2312B includes a respective tip 2315A, 2315B that extends approximately 0.045 inches (+/−0.005 inches) from the cap 2308. In other implementations, the sutures 2312A, 2312B may extend from the distal cap 2008 by a distance from and including 0.020 inches to and including 0.080 inches.

As previously noted, each of the distal sutures 2312A, 2312B extends at least partially in a distal direction. As illustrated in FIGS. 24A-B and with reference to the distal suture 2312A, the extent to which the distal sutures 2312A, 2312B extend in the distal direction may be defined by an angle ψ relative to a plane 2333 (FIGS. 24A-B) transverse to the longitudinal axis 2301 of the biostimulator 2300. In the specific example of the biostimulator 2300, the angle ψ is approximately 60 degrees. In other implementations, the angle ψ may have any other suitable value such as from and including 15 degrees to and including 75 degrees.

Each of the distal sutures 2312A, 2312B may also be "swept" in a direction counter to that of the primary helix 2305. For example, the suture 2312A extends at an angle of approximately 30 degrees relative to a first distal radial line 2309A extending from the longitudinal axis 2301 through an origin 2311A of the suture 2312A, the origin 2311A corresponding to a location of the cap 2308 from which the suture 2312A emerges. Similarly, the suture 2312B also extends at an angle of approximately 30 degrees relative to a second distal radial line 2309B extending from the longitudinal axis 2301 through an origin 2311B of the suture 2312B, the origin 2311B corresponding to a location of the cap 2308 from which the suture 2312B emerges. In other implementations, the proximal sutures 2313A-2313C may extend relative to their respective proximal radial lines 2323A-2323C at an angle from and including 15 degrees to and including 75 degrees.

In an embodiment, each filament tip can be shaped to have a filament face along the respective filament axis 1602, which is at an angle to the filament axis. For example, as shown, each tip 2317A-2317C can be cut or trimmed at approximately a 30 degree angle.

As previously discussed, in addition to the distal sutures 2312A, 2312B, the leadless biostimulator 2300 further includes a set of proximal lateral sutures 2313A-2313C extending from the helix mount 2306. The proximal lateral sutures 2313A-2313C are evenly distributed about the helix mount 2306 such that they are disposed 120 degrees apart from each other. The proximal lateral sutures 2313A-2313C are also disposed at locations that are offset approximately 60 degrees, 180 degrees, and 300 degrees, respectively, from the tip 2352 of the primary helix 2305.

In another example implementation, the proximal lateral sutures 2313A-2313C are disposed at locations that are offset approximately 45 degrees, 165 degrees, and 285 degrees, respectively, from the tip 2352 of the primary helix 2305. In still other implementations, the proximal lateral sutures 2313A-2313C may instead be disposed at locations that are offset from and including 30 degrees to and including 70 degrees, from and including 150 degrees to and including 190 degrees, and from and including 270 degrees to and including 320 degrees, respectively, from the tip 2352 of the primary helix 2305. As illustrated in FIGS. 24A-B, the proximal lateral sutures 2313A-2313C may be offset from the origins 2311A, 2311B of the distal sutures 2312A, 2312B by a distance 2321 of approximately 0.01 inches. In other implementations, the distance 2321 may be from and including 0.005 inches to and including 0.050 inches. Also, as illustrated in FIGS. 24A-B, the longitudinal distance between the distal sutures 2312A, 2312B and the proximal lateral sutures 2313A-2313C may vary for each of the proximal lateral sutures 2313A-2313C. For example, the helix mount 2306 may have a helical shape and the proximal lateral sutures 2313A-2313C may extend at various points along the helical shape such that each of the proximal lateral sutures 2313A-2313C is disposed at a different longitudinal location.

In the specific example of the biostimulator 2000, the proximal lateral sutures 2313A-2313C are #4-0 sutures having a diameter ranging between approximately 0.15 mm and 0.2 mm and are formed from nylon. As illustrated in FIG. 25, each of the proximal lateral sutures 2313A-2313C extends laterally from the helix mount 2306 such that a tip 2317A-2317C of each suture 2313A-2313C extends approximately 0.020 inches (+/−0.005 inches) from the helix mount 2306.

In other implementations, the sutures 2313A-2313C may extend from the helix mount 2306 by a distance from and including 0.010 inches to and including 0.030 inches. The suture 2313A extends at an angle of approximately 30 degrees relative to a first proximal radial line 2323A extending from the longitudinal axis 2301 through an origin 2317A of the suture 2313A, the origin 2317A corresponding to a location of the helix mount 2306 from which the suture 2313A emerges. The suture 2313B also extends at an angle of approximately 30 degrees relative to a second proximal radial line 2323B extending from the longitudinal axis 2301 through an origin 2317B of the suture 2313B, the origin 2317B corresponding to a location of helix mount 2306 from which the suture 2312B emerges. Finally, the suture 2317C extends at an angle of approximately 30 degrees relative to a third proximal radial line 2323C extending from the longitudinal axis 2305 through an origin 2317C of the suture 2313C, the origin 2319C corresponding to a location of helix mount 2306 from which the suture 2313C emerges. In other implementations, the proximal sutures 2313A-2313C may extend relative to their respective proximal radial lines 2323A-2323C at an angle from and including 15 degrees to and including 75 degrees. As shown, each tip 2317A-2317C is also cut or trimmed at approximately a 30 degree angle relative to the respective radial line 2315A-2315C.

The specific configuration of the biostimulator 2300 illustrated in FIGS. 23-25 and described above in more detail exhibited strong performance characteristics during testing. Nevertheless, while the biostimulator 2300 represents one possible arrangement of components, it is provided merely as an example intended to illustrate one specific configuration in accordance with this disclosure. As described throughout this disclosure, other arrangements may be possible and may exhibit other advantages and favorable performance characteristics. Accordingly, the scope of this disclosure should not be limited to the specific implementation of FIGS. 23-25.

As noted above, screwing fixation element 205 into target tissue until tissue is captured at the pinch point 2110 can increase resistance to torque-out. Furthermore, mounting fixation element 205 on helix mount 206 such that the wire extends approximately 1.5 turns from the distal end of the helix mount 206 provides a balance between the ease with which the primary helix 205 may be made to engage the wall of the heart and the strength of such engagement. More particularly, it has been determined that mounting fixation element 205 on helix mount 206 such that wire extends about 1.5 turns from the pinch point 2110, can improve securement of biostimulator 100 to the target tissue. As described below, methods of manufacture and device features can be implemented to achieve this benefit.

Referring again to FIG. 21A, helix mount 2006 can include a marking to define a range within which leading point 2052 can be aligned to set a predefined clocking of fixation element 2005 on biostimulator 2000. For example, helix mount flange 2160 can include one or more marks 2150 that define an alignment range 2152. Alignment range 2152 may be a circumferential range, measured along the circumference or outer surface of helix mount flange 2160. The circumferential range can be between a leftward boundary and a rightward boundary of the marks 2150. For example, mark(s) 2150 may include two marks, e.g., a leftward mark that is laser marked on helix mount flange 2160 and a rightward mark that is laser marked on helix mount flange 2160 (FIG. 21A). The leftward mark would have a leftward edge defining the leftward boundary and the rightward mark would have a rightward edge defining the rightward boundary. Alternatively, mark(s) 2150 may include a single mark, e.g., laser marked on helix mount flange 2160, having a leftward edge defining the leftward boundary and a rightward edge defining the rightward boundary. (FIG. 24A).

In an embodiment, mark(s) 2150 provide a manufacturing aid to ensure that leading point 1052 (2052) is the correct number of turns from the distal end of the helix mount. For example, during manufacturing the helix mount 2006 having mark(s) 2150 can be mounted on housing 102. The mark(s) define an alignment range 2152. In an operation, the fixation element 2005 can be screwed onto the helix mount 2006. For example, the coiled wire can be threaded into the groove of helix mount flange 2160 until the leading point 2052 of the wire is aligned with the alignment range 2152.

As shown in FIGS. 21B and 24B, in the aligned state, the wire of fixation element 205 can extend over 1.4 to 1.6 turns, e.g., 1.455 to 1.555 turns of the helical axis 1001 from pinch point 2110 to the leading point. For example, when the leading point is vertically aligned with alignment range 2152, the wire can extend over 1.4 to 1.6 turns, e.g., between 1.455 to 1.555 turns, e.g., 1.5 turns, of the helical axis from the distal end of helix mount flange 2160. Vertical alignment can refer to the leading point being within an arc volume located between a first vertical plane radiating from the longitudinal axis and extending through the leftward boundary of mark(s) 2150 and a second vertical plane radiating from the longitudinal axis and extending through the rightward boundary of mark(s) 2150. When the leading point is aligned within such an arc volume, biostimulator 2300 can be configured such that screwing fixation element 2305 into target tissue more than 1.5 turns will cause tissue to be sheared and clamped at pinch point 2110. The pinch point 2110 is located 1800 away from the tip of the helix 2052.

In addition to their use as manufacturing aids, mark(s) 2150 may also be used to promote accurate implantation of biostimulator 100 in a clinical setting. In an embodiment, mark(s) 2150 are radiopaque. For example, mark 2150 can be printed or painted on helix mount 206 using a radiopaque ink. Alternatively, mark 2150 can be a radiopaque inlay, such as a tantalum or platinum post or plate, which can be bonded or press fit into helix mount 206. In any case, the radiopaque mark 2150 can be imaged under fluoroscopy and/or using another imaging modality to allow an operator to view a position of mark 2150 when biostimulator 100 is implanted within a target anatomy.

In an embodiment, a method of using biostimulator 100 includes implanting the biostimulator as shown and described with respect to FIGS. 6A-6B. When the biostimulator is advanced to the target tissue and contact is made between the tissue and fixation element 105, the operator can take note of the location of the radiopaque mark 2150. To secure biostimulator 100 to the tissue, the operator can effect rotation of the biostimulator such that the fixation element engages and screws into the target tissue. During rotation of the biostimulator, the operator can monitor the number of rotations of mark 2150 under fluoroscopy. When an intended number of rotations of the mark is observed, the operator can cease turning of biostimulator 100 and disengage the biostimulator to leave it implanted in the target tissue.

It is noted that the number of turns of biostimulator 100, as controlled by the number of rotations of mark 2150, may be a degree of rotation between the leading point and the pinch point of the biostimulator, e.g., 1.5 turns. The operator may, however, turn the biostimulator to a more or lesser degree depending on the particular patient. For example, when the patient has friable tissue, the operator may choose to rotate the biostimulator by 1.25 turns instead of 1.5 turns. The visibility of mark 2150 under clinical imaging modalities allows such accurate control of implantation to occur.

Figure 31:
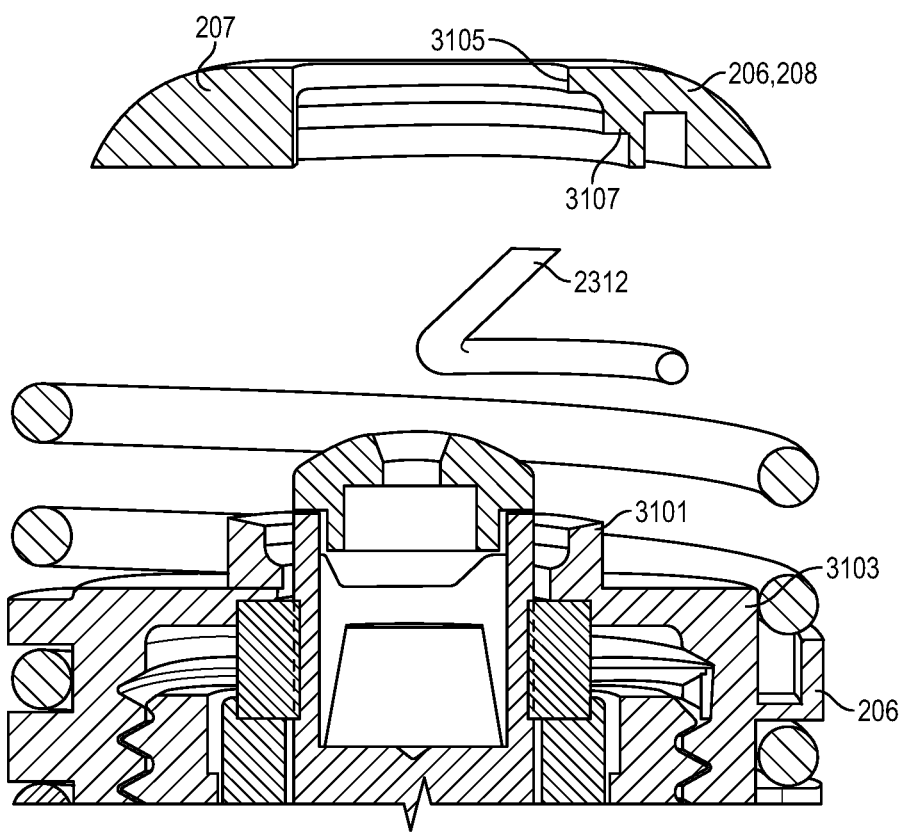
FIG. 31 is an exploded cross-sectional view of a distal end of the biostimulator, in accordance with the present disclosure.

Referring to FIG. 31, an exploded cross-sectional view of a distal end of the biostimulator is shown in accordance with the present disclosure. Helix mount 206 can include cap 208 and helix mount flange 2160. The cap 208 can have a distal face 207, which can be a forward facing surface of cap 208. In an aspect, the distal face 207 can be smooth. For example, the entire surface of distal face 207 can be without an edge, a burr, or a discontinuity. The smoothness of the distal face 207 may result from the structure described below.

In an embodiment, mounting flange 2160 includes an energy director 3101 that extends distally from a flange base 3103. The flange base 3103 can include internal threads to mount to threaded section 704.

In an embodiment, cap 208 includes a boss 3107, which may be a consumptive or deformable area for creating a weld between cap 208 and energy director 3101. Cap 208 may have a rounded distal face 207, and a through-hole extending longitudinally through the face. The through-hole can have an inner diameter 3105 that is slightly larger than electrode 211. By contrast, the inner diameter 3105 may be smaller than an inner dimension of energy director 3101. Accordingly, an end view of distal face 207 may reveal electrode 211 and not energy director 3101. More particularly, boss 3107 can be ultrasonically welded to energy director 3101 by pressing cap 208 against an upper edge of the energy director and applying ultrasonic energy to the components until the material of the components fuse together. The fused material forms a weld that bonds cap 208 to helix mount flange 2160, thus forming a two-component helix mount 206.

In an aspect, the weld that bonds the several mount components is hidden from view by cap 208. More particularly, the weld and flowed material is proximal of cap 208 and does not flow through inner diameter 3105. As a result, distal face 207 is continuously smooth and no weld edge is present on the smooth surface that could rub against the target tissue over time. Thus, a two-part helix mount 206 having a weld or other bond between cap 208 and flange 2160 (and visually hidden by distal face 207) may reduce a likelihood of trauma to tissue over time.

Several embodiments are described by way of summary, and not by way of limitation, in the following paragraphs.

In an embodiment, a leadless biostimulator for implantation within a heart of a patient, the heart including a wall, is provided. The leadless biostimulator includes a housing sized and configured to be implanted within the heart. The housing includes a distal face and defines a longitudinal axis. The leadless biostimulator includes a primary fixation helix attached to the housing and configured to affix the housing to the wall of the heart by rotating in a screwing direction. The primary fixation helix extends distally beyond the distal face and defines a helix radius relative to the longitudinal axis. The leadless biostimulator includes one or more secondary fixation elements extending from the distal face. Each of the one or more secondary fixation elements originate from a respective secondary fixation element origin disposed at a respective radius relative to the longitudinal axis. The respective radius is less than the helix radius.

In the embodiment, the one or more secondary fixation elements are composed of a flexible biocompatible material.

In the embodiment, the flexible biocompatible material is chosen from a group consisting of polypropylene, polyethylene, polyester, polyurethane, silicone, poly(lactic acid), poly(glycolic acid), polyimide, polyether ether ketone, and polycarbonate.

In the embodiment, the flexible biocompatible material is a natural material.

In the embodiment, the flexible biocompatible material is chosen from a group consisting of, hair, horse hair, nail, hide, horn, sharkskin, and plant fiber.

In the embodiment, the one or more secondary fixation elements includes from one to eight secondary fixation elements.

In the embodiment, the one or more secondary fixation elements extend beyond the helix radius.

In the embodiment, the one or more secondary fixation elements extend between adjacent turns of the primary fixation helix.

In the embodiment, the primary fixation helix extends from and includes an eighth of a turn to and including two turns beyond the one or more secondary fixation elements.

In the embodiment, the one or more secondary fixation elements point in a direction substantially opposite the primary fixation helix such that rotation of the housing in an unscrewing direction causes the one or more secondary fixation elements to engage the wall of the heart so as to prevent the primary fixation helix from disengaging the wall of the heart.

In an embodiment, a leadless biostimulator for implantation within a heart of a patient, the heart including a wall, is provided. The leadless biostimulator includes a housing sized and configured to be implanted within the heart. The housing includes a distal face and defines a longitudinal axis. The leadless biostimulator includes a primary fixation helix attached to the housing and configured to affix the housing to the wall of the heart by rotating in a screwing direction. The primary fixation helix extends distally beyond the distal face and defines a helix radius relative to the longitudinal axis. The leadless biostimulator includes one or more secondary fixation elements extending from the distal face. Each of the one or more facing secondary fixation elements originates from a respective secondary fixation element origin disposed at a respective secondary fixation element radius relative to the longitudinal axis. The respective secondary fixation element radius is less than the helix radius. The one or more secondary fixation elements extend along a secondary fixation element plane perpendicular to the longitudinal axis.

In the embodiment, each of the one or more secondary fixation elements extends at an angle relative to a line extending between the longitudinal axis and its respective secondary fixation element origin. The angle is from and including 15 degrees to and including 75 degrees.

In the embodiment, the one or more secondary fixation elements extend beyond the helix radius.

In the embodiment, the one or more secondary fixation elements extend between adjacent turns of the primary fixation helix.

In the embodiment, the one or more secondary fixation elements are composed of a flexible biocompatible material.

In the embodiment, the flexible biocompatible material is chosen from a group consisting of polypropylene, polyethylene, polyester, polyurethane, silicone, poly(lactic acid), poly(glycolic acid), polyimide, polyether ether ketone, and polycarbonate.

In the embodiment, the flexible biocompatible material is chosen from a group consisting of hair, horse hair, nail, hide, horn, sharkskin, and plant fiber.

In an embodiment, a leadless biostimulator for implantation within a heart of a patient, the heart including a wall, is provided. The leadless biostimulator includes a housing sized and configured to be implanted within the heart. The housing includes a distal face and defines a longitudinal axis. The leadless biostimulator includes a primary fixation helix attached to the housing and configured to affix the housing to the wall of the heart by rotating in a screwing direction. The primary fixation helix extends distally beyond the distal face and defines a helix radius relative to the longitudinal axis. The leadless biostimulator includes one or more secondary fixation elements extending from the distal face. Each of the one or more secondary fixation elements originates from a respective secondary fixation element origin disposed at a respective secondary fixation element radius relative to the longitudinal axis. The respective secondary fixation element radius is less than the helix radius. The one or more secondary fixation elements extend distally, at least in part, from the distal face.

In the embodiment, each of the one or more secondary fixation elements extends at an angle relative to a line extending between the longitudinal axis and its respective secondary fixation element origin. The angle is from and including 15 degrees to and including 75 degrees.

In the embodiment, each of the one or more secondary fixation elements extends in the distal direction at an angle from and including 15 degrees to and including 75 degrees.

In the embodiment, the one or more secondary fixation elements extend beyond the helix radius.

In the embodiment, the one or more secondary fixation elements extend between adjacent turns of the primary fixation helix.

In the embodiment, the one or more secondary fixation elements are composed of a flexible biocompatible material chosen from a group consisting of polypropylene, polyethylene, polyester, polyurethane, silicone, poly(lactic acid), poly(glycolic acid), polyimide, polyether ether ketone, and polycarbonate.

In the embodiment, the flexible biocompatible material is chosen from a group consisting of, hair, horse hair, nail, hide, horn, sharkskin, and plant fiber.

In an embodiment, a leadless biostimulator for implantation within a heart of a patient, the heart including a wall, is provided. The leadless biostimulator includes a housing sized and configured to be implanted within the heart. The leadless biostimulator includes a primary fixation helix attached to the housing and configured to affix the housing to the wall of the heart by rotating in a screwing direction. The leadless biostimulator includes one or more side or forward facing secondary fixation elements extending distally from the housing. The one or more side or forward facing secondary fixation elements are configured to point in a direction substantially opposite the primary fixation helix such that rotation of the housing in an unscrewing direction causes the one or more side or forward facing secondary fixation elements to engage the wall of the heart so as to prevent the primary fixation helix from disengaging the wall of the heart.

In the embodiment, the one or more secondary fixation elements are composed of a flexible biocompatible material.

In the embodiment, the flexible biocompatible material is chosen from a group consisting of polypropylene, polyethylene, polyester, polyurethane, silicone, poly(lactic acid), poly(glycolic acid), polyimide, polyether ether ketone, polycarbonate, hair, horse hair, nail, hide, horn, sharkskin, and plant fiber.

In the embodiment, the one or more secondary fixation elements have a diameter from and including 0.003 inches to and including 0.03 inches.

In the embodiment, the one or more side or forward facing secondary fixation elements includes from one to eight secondary fixation elements.

In the embodiment, the housing defines a longitudinal axis, and each secondary fixation element of the one or more secondary fixation elements further defines: a first axis parallel to the longitudinal axis extending through an origin of the secondary fixation element, a second axis perpendicular to the first axis, the second axis extending from the origin to the longitudinal axis, and a third axis perpendicular to each of the longitudinal axis and the second axis. The secondary fixation element extends from the origin at an angle $\alpha$ with respect to the first axis and an angle $\beta$ with respect to the third axis, $\alpha$ being from and including 10 degrees to and including 50 degrees and $\beta$ being from and including 15 degrees to and including 75 degrees.

In the embodiment, each secondary fixation element of the one or more secondary fixation elements extends from and including 0.01 inches to and including 0.3 inches from its respective origin.

In the embodiment, the primary fixation helix extends from and includes 0.25 turns to and including 3 turns from the housing and has a wire diameter from and including 0.003 inches to and including 0.03 inches, a pitch diameter from and including 0.06 inches to and including 0.3 inches, and a pitch from and including 0.01 inches to and including 0.05 inches.

In the embodiment, the leadless biostimulator further includes one or more lateral secondary fixation elements extending laterally relative to a longitudinal axis defined by the housing. The one or more forward lateral secondary fixation elements configured to point in a direction substantially opposite the primary fixation helix such that rotation of the housing in the unscrewing direction causes the lateral secondary fixation elements to engage the wall of the heart so as to prevent the primary fixation helix from disengaging the wall of the heart.

In the embodiment, each of the one or more lateral secondary fixation elements includes a lateral secondary fixation element origin and a respective normal extends from the longitudinal axis to each of the one or more lateral secondary fixation elements. Each of the one or more lateral secondary fixation elements extends at an angle from and including 15 degrees to and including 75 degrees relative to the normal.

In the embodiment, the one or more lateral secondary fixation elements are disposed in a body coupled to the housing. Each of the one or more lateral secondary fixation elements extends from and includes 0.003 inches to and including 0.05 inches from the body.

In the embodiment, the primary fixation helix defines an inner diameter and at least one of the one or more side or forward facing secondary fixation elements extends beyond the inner diameter such that during unscrewing of the primary fixation helix after fixation of the primary fixation helix to the wall of the heart, the at least one secondary fixation element interferes with the primary fixation helix.

In the embodiment, each of the one or more secondary fixation elements has a Young's Modulus from and including 0.5 gigapascals to and including 10 gigapascals.

In an embodiment, a leadless biostimulator for implantation within a heart of a patient, the heart having a wall, is provided. The leadless biostimulator includes a housing sized and configured to be implanted within the heart. The leadless biostimulator includes a header assembly coupled to the housing. The header assembly includes a helix mount having a primary fixation helix configured to affix the housing to the wall of the heart by rotating in a screwing direction. The header assembly includes a flange coupled to the housing and the helix mount, the flange extending through the primary fixation helix. The header assembly includes a cap including one or more side or forward facing secondary fixation elements extending laterally or distally from the header assembly, the one or more side or forward facing secondary fixation elements configured to point in a direction substantially opposite the primary fixation helix such that rotation of the housing in an unscrewing direction causes the side or forward facing secondary fixation elements to engage the wall of the heart so as to prevent the primary fixation helix from disengaging the wall of the heart.

In the embodiment, the one or more secondary fixation elements are composed of a flexible biocompatible material.

In the embodiment, the housing defines a longitudinal axis, and each secondary fixation element of the one or more secondary fixation elements further defines: a first axis parallel to the longitudinal axis extending through an origin of the secondary fixation element; a second axis perpendicular to the first axis, the second axis extending from the origin to the longitudinal axis; and a third axis perpendicular to each of the longitudinal axis and the second axis. The secondary fixation element extends from the origin at an angle α with respect to the first axis and an angle β with respect to the third axis, a being from and including 10 degrees to and including 50 degrees and p being from and including 15 degrees to and including 75 degrees.

In the embodiment, the leadless biostimulator further includes one or more lateral secondary fixation elements coupled to the helix mount. The one or more lateral secondary fixation elements extend laterally from the helix mount and point in a direction substantially opposite the primary fixation helix such that rotation of the housing in the unscrewing direction causes the lateral secondary fixation elements to engage the wall of the heart so as to prevent the primary fixation helix from disengaging the wall of the heart.

In the embodiment, the helix mount includes a first orientation feature and the cap includes a second orientation. The first orientation feature mates with the second orientation feature to maintain the one or more secondary fixation elements in a predetermined position relative to the primary fixation helix.

In the embodiment, the one or more secondary fixation elements includes at least a first secondary fixation element and a second secondary fixation element and the cap defines each of a first secondary fixation element bore through which the first secondary fixation element extends, a second secondary fixation element bore through which the second secondary fixation element extends, and a secondary fixation element groove extending between the first secondary fixation element bore and the second secondary fixation element bore. The first secondary fixation element and the second secondary fixation element are formed from a shared length of secondary fixation element material extending between the first secondary fixation element bore and the second secondary fixation element bore through the secondary fixation element grove.

In an embodiment, a leadless biostimulator for implantation within a heart of a patient, the heart including a wall, is provided. The leadless biostimulator includes a housing sized and configured to be implanted within the heart and defines a longitudinal axis. The leadless biostimulator includes a primary fixation helix attached to the housing and configured to affix the housing to the wall of the heart by rotating in a screwing direction. The leadless biostimulator includes two side or forward facing secondary fixation elements extending distally from the housing. The one or more side or forward facing secondary fixation elements are configured to point in a direction substantially opposite the primary fixation helix such that rotation of the housing in an unscrewing direction causes the side or forward facing secondary fixation elements to engage the wall of the heart so as to prevent the primary fixation helix from disengaging the wall of the heart. Each of the side or forward facing secondary fixation elements is composed of polypropylene, has a diameter from and including 0.003 inches to and including 0.03 inches, has a Young's Modulus from and including 0.5 gigapascals to and including 10 gigapascals, defines a first axis parallel to the longitudinal axis extending through an origin of the secondary fixation element, defines a second axis perpendicular to the first axis, the second axis extending from the origin to the longitudinal axis, and defines a third axis perpendicular to each of the longitudinal axis and the second axis. The secondary fixation element extends from the origin from and including 0.01 inches to and including 0.3 inches at an angle α with respect to the first axis and an angle β with respect to the third axis, a being from and including 10 degrees to and including 50 degrees and p being from and including 15 degrees to and including 75 degrees.

In an embodiment, a leadless biostimulator for implantation within a heart of a patient, the heart including a wall, is provided. The leadless biostimulator includes a housing sized and configured to be implanted within the heart. The leadless biostimulator includes a fixation helix formed from a coiled wire. The fixation helix is attached to a distal end of the housing and is configured to affix the housing to the wall of the heart by rotating in a screwing direction. The fixation helix includes a tip formed by three or more bevels. The tip is disposed about an outer perimeter of the coiled wire.

In the embodiment, the fixation helix defines a helix axis, the three or more bevels form an edge extending between the tip and an edge base disposed on the outer perimeter opposite the tip, and the edge extends at an angle θ away from a vector extending distally from the edge base parallel to the helix axis, the angle θ being along a plane defined by both of the helix axis and the vector and measuring from and including 0 degrees to and including 180 degrees.

In the embodiment, the angle θ is from and including 90 degrees to and including 180 degrees.

In the embodiment, the edge extends at an angle ψ away from the plane, the angle ψ being from and including 10 degrees to and including 60 degrees.

In the embodiment, the coiled wire is one of round wire, flattened wire, hypodermic tubing, and plastic wire.

In the embodiment, the fixation helix has a pitch from and including 0.007 inches to and including 0.060 inches.

In the embodiment, the fixation helix has a pitch angle from and including 2.5 degrees to and including 20 degrees.

In the embodiment, the leadless biostimulator further includes at least one contact surface that interacts with the wall of the heart when the leadless biostimulator is implanted within the heart. The at least one contact surface has at least one surface modification treatment applied thereto. The surface modification treatment modifies at least one of a surface energy, a surface charge, a surface chemistry, or a surface morphology of the portion of the fixation helix relative to a substrate material to which the surface modification treatment is applied.

In an embodiment, a leadless biostimulator for implantation within a heart of a patient, the heart including a wall, is provided. The leadless biostimulator includes a housing sized and configured to be implanted within the heart. The leadless biostimulator includes a fixation helix formed from a coiled wire. The fixation helix is attached to a distal end of the housing and configured to affix the housing to the wall of the heart by rotating in a screwing direction. The fixation helix includes a helical untapered portion terminating in a tapered tip. The tapered tip terminates within a projected volume extending from the helical untapered portion. The projected volume has a helical shape conforming to the helical untapered portion.

In the embodiment, the tapered tip is formed by several bevels.

In the embodiment, the several bevels consists of two bevels and the tapered tip terminates along an outer extent of the projected volume.

In the embodiment, the tapered tip terminates from and including 0.002 inches to and including 0.02 inches from the untapered portion.

In the embodiment, the tapered tip terminates from and including 0.001 inches to and including 0.009 inches from a longitudinal axis defined by the coiled wire.

In the embodiment, the fixation helix has a pitch from and including 0.007 inches to and including 0.060 inches.

In the embodiment, the fixation helix has a pitch angle from and including 2.5 degrees to and including 20 degrees.

In the embodiment, the several bevels includes at least three bevels, and the tapered tip terminates: (i) from and including 0.002 inches to and including 0.02 inches from the untapered portion, (ii) from and including 0.001 inches to and including 0.009 inches from a longitudinal axis defined by the coiled wire, and (iii) from and including 90 degrees to and including 160 degrees relative to a tip axis, the tip axis extending perpendicular to the longitudinal axis and parallel to a helix axis of the fixation helix.

In an embodiment, a leadless biostimulator for implantation within a heart of a patient, the heart including a wall, is provided. The leadless biostimulator includes a housing sized and configured to be implanted within the heart. The leadless biostimulator includes a fixation helix formed from a coiled wire, coupled to a distal end of the housing, and extending along a helix axis. The fixation helix is configured to affix the housing to the wall of the heart by rotating in a screwing direction. The fixation helix includes a tip disposed on an outer perimeter of the coiled wire and formed by three or more bevels. The three or more bevels form an edge extending between the tip and an edge base disposed on the outer perimeter opposite the tip. The edge extends at an angle θ away from a vector distally extending from the edge base parallel to the helix axis. The angle θ being along a plane defined by the helix axis and the vector and being from and including 90 degrees to and including 180 degrees.

In the embodiment, the angle θ is 90 degrees.

In the embodiment, the angle θ is 180 degrees.

In the embodiment, the edge extends at an angle ψ away from the plane, the angle ψ being from and including 10 degrees to and including 60 degrees, and the tip has a length from and including 0.002 inches to and including 0.02 inches.

In an embodiment, a leadless biostimulator for implantation within a heart of a patient, the heart including a wall, is provided. The leadless biostimulator includes a housing sized and configured to be implanted within the heart and defining a longitudinal axis. The leadless biostimulator includes a header assembly coupled to a distal end of the housing and having a distal face. The header assembly includes a helix mount. The header assembly includes a fixation helix coupled to the helix mount and extending distally from the helix mount. The fixation helix is configured to affix the housing to the wall of the heart by rotating in a screwing direction. The header assembly includes several distal secondary fixation elements extending laterally from the distal face and at least partially in a direction opposite the screwing direction. The header assembly includes several proximal secondary fixation elements proximal the distal secondary fixation elements. The proximal secondary fixation elements extend laterally from the helix mount and at least partially in a direction opposite the screwing direction.

In the embodiment, the fixation helix includes a sharpened tip disposed on a lateral extent of the primary helix relative to the longitudinal axis.

In the embodiment, the fixation helix extends approximately 1.5 turns beyond the distal face of the header assembly.

In the embodiment, the several distal secondary fixation elements consists of a first distal secondary fixation element and a second distal secondary fixation element. The first distal secondary fixation element is disposed at a first offset of approximately 90 degrees relative to a tip of the fixation helix and the second distal secondary fixation element is disposed at a second offset of approximately 270 degrees relative to the tip of the fixation helix.

In the embodiment, each distal secondary fixation element of the several distal secondary fixation elements extends at an angle from and including 15 degrees to and including 75 degrees relative to a respective radial line extending from the longitudinal axis to a respective origin of the distal secondary fixation element.

In the embodiment, each distal secondary fixation element extends at an angle of approximately 30 degrees relative to the respective radial line.

In the embodiment, each distal secondary fixation element of the several distal secondary fixation elements extends from and including 0.020 inches to and including 0.080 inches from the distal face.

In the embodiment, each distal secondary fixation element of the several distal secondary fixation elements extends approximately 0.045 inches from the distal face.

In the embodiment, each distal secondary fixation element is a #3-0 suture.

In the embodiment, the several proximal secondary fixation elements consists of a first proximal secondary fixation element, a second proximal secondary fixation element, and a third proximal secondary fixation element. The first proximal secondary fixation element is disposed at a first offset from and including 30 degrees to and including 70 degrees relative to a tip of the fixation helix. The second proximal secondary fixation element is disposed at a second offset of from and including 150 degrees to and including 190 degrees relative to the tip of the fixation helix. The third proximal secondary fixation element is disposed at a third offset of from and including 270 degrees to and including 320 degrees relative to the tip of the fixation helix.

In the embodiment, each proximal secondary fixation element of the several proximal secondary fixation elements extends at an angle from and including 15 degrees to and including 75 degrees relative to a respective radial line extending from the longitudinal axis to a respective origin of the proximal secondary fixation element.

In the embodiment, each proximal secondary fixation element extends at an angle of approximately 30 degrees relative to the respective radial line.

In the embodiment, each proximal secondary fixation element of the several proximal secondary fixation elements extends from and including 0.010 inches to and including 0.030 inches from the helix mount.

In the embodiment, each proximal secondary fixation element extends approximately 0.020 inches from the distal face.

In the embodiment, each proximal secondary fixation element is a #4-0 suture.

In the embodiment, the several distal secondary fixation elements is longitudinally offset from the several proximal secondary fixation elements by a distance from and including 0.005 inches to and including 0.050 inches.

In the embodiment, the distance is approximately 0.01 inches.

In an embodiment, a leadless biostimulator for implantation within a heart of a patient, the heart including a wall, is provided. The leadless biostimulator includes a housing sized and configured to be implanted within the heart, and defining a longitudinal axis. The leadless biostimulator includes a distal fixation assembly coupled to a distal end of the housing. The distal fixation assembly includes a helix mount including a distal face. The distal fixation assembly includes a fixation helix attached to the helix mount and extending distally from the helix mount. The fixation helix is configured to affix the housing to the wall of the heart by rotating in a screwing direction. The distal fixation assembly includes several distal secondary fixation elements extending from the distal face. The distal fixation assembly includes several proximal secondary fixation elements proximal the distal secondary fixation elements and extending laterally from the helix mount in a direction opposite the screwing direction. Each distal secondary fixation element of the several distal secondary fixation elements extends in a distal direction at a first angle relative to a plane transverse to the longitudinal axis and opposite the screwing direction at a second angle relative to a respective radial line extending from the longitudinal axis to a respective origin of the distal secondary fixation element. Each of the first angle and the second angle being from and including 15 degrees to and including 75 degrees.

In the embodiment, each of the distal secondary fixation elements is a #3-0 suture and extends from and including 0.020 to and including 0.080 inches from the distal face.

In the embodiment, each proximal secondary fixation element of the several proximal secondary fixation elements is a #4-0 suture extending from and including 0.010 inches to and including 0.030 inches from the helix mount at an angle from and including 15 degrees to and including 75 degrees relative to a respective radial line extending from the longitudinal axis to a respective origin of the proximal secondary fixation element.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A biostimulator, comprising:
   a fixation element including an outer surface extending along a helical axis about a longitudinal axis to a distal edge, wherein the outer surface peripherally surrounds the helical axis and the distal edge extends peripherally about the helical axis, wherein a wire face having three or more helix faces tapers distally and radially inward from the distal edge to converge at a leading point within a projected volume of the outer surface and radially between the helical axis and the distal edge.

2. The biostimulator of claim 1, wherein the three or more helix faces includes a plurality of bevel faces converging at the leading point.

3. The biostimulator of claim 1, wherein the outer surface includes an ellipsoidal outer surface, and wherein the distal edge is defined by an intersection between the ellipsoidal outer surface extending around the helical axis and the plurality of helix faces.

4. The biostimulator of claim 1, wherein the leading point is radially inward from the distal edge.

5. The biostimulator of claim 4, wherein a transverse plane extends orthogonal to the longitudinal axis and intersects the helical axis, and wherein the leading point is distal to the transverse plane.

6. The biostimulator of claim 5, wherein a longitudinal plane extends orthogonal to the transverse plane and parallel to the longitudinal axis such that the longitudinal plane and the transverse plane intersect at a center of the wire face, and wherein the leading point is along the longitudinal plane distal to the transverse plane.

7. The biostimulator of claim 4, wherein a transverse plane extends orthogonal to the longitudinal axis and intersects the helical axis, and wherein the leading point is proximal to the transverse plane.

8. The biostimulator of claim 7, wherein a longitudinal plane extends orthogonal to the transverse plane and parallel to the longitudinal axis such that the longitudinal plane and the transverse plane intersect at a center of the wire face, and wherein the leading point is along the longitudinal plane proximal to the transverse plane.

9. The biostimulator of claim 1, wherein the wire face has a plurality of quadrants, and wherein the leading point is within a quadrant of the plurality of quadrants.

10. The biostimulator of claim 9, wherein the quadrant is a left quadrant.

11. The biostimulator of claim 9, wherein the quadrant is a right quadrant.

12. A biostimulator system, comprising:
    a torqueable catheter; and
    a biostimulator coupled to the torqueable catheter, wherein the biostimulator includes
       a housing having a longitudinal axis and containing an electronics compartment, and
       a fixation element mounted on the housing, wherein the fixation element includes an outer surface extending along a helical axis about a longitudinal axis to a distal edge, wherein the outer surface peripherally surrounds the helical axis and the distal edge extends peripherally about the helical axis, wherein a wire face having three or more helix faces tapers distally and radially inward from the distal edge to converge at a leading point within a projected volume of the outer surface and radially between the helical axis and the distal edge.

13. The biostimulator system of claim 12, wherein the three or more helix faces includes a plurality of bevel faces converging at the leading point.

14. The biostimulator system of claim 12, wherein the outer surface includes an ellipsoidal outer surface, and wherein the distal edge is defined by an intersection between the ellipsoidal outer surface extending around the helical axis and the plurality of helix faces.

15. The biostimulator system of claim 12, wherein the leading point is radially inward from the distal edge.

16. The biostimulator system of claim 12, wherein the wire face has a plurality of quadrants, and wherein the leading point is within a quadrant of the plurality of quadrants.

17. The biostimulator system of claim 16, wherein the quadrant is a left quadrant.

18. The biostimulator system of claim 16, wherein the quadrant is a right quadrant.

19. A method, comprising:
   advancing a catheter to a target anatomy, wherein a biostimulator is coupled to the catheter, wherein the biostimulator includes a housing having a longitudinal axis and containing an electronics compartment, and a fixation element mounted on the housing, wherein the fixation element includes an outer surface extending along a helical axis about a longitudinal axis to a distal edge, wherein the outer surface peripherally surrounds the helical axis and the distal edge extends peripherally about the helical axis, wherein a wire face having three or more helix faces tapers distally and radially inward from the distal edge to converge at a leading point within a projected volume of the outer surface and radially between the helical axis and the distal edge; and
   torqueing the catheter to rotate the housing and force the fixation element into the target anatomy.

* * * * *